(12) United States Patent
Irlapati et al.

(10) Patent No.: US 9,409,898 B2
(45) Date of Patent: Aug. 9, 2016

(54) SUBSTITUTED PYRAZOLE COMPOUNDS AS CRAC MODULATORS

(71) Applicant: LUPIN LIMITED, Mumbai, Maharashtra (IN)

(72) Inventors: Nageswara Rao Irlapati, Maharashtra (IN); Gokul Keruji Deshmukh, Maharashtra (IN); Nilesh Raghunath Khedkar, Maharashtra (IN); Kiran Chandrashekhar Kulkarni, Maharashtra (IN); Zubair Abdul Wajid Shaikh, Maharashtra (IN); Neelima Sinha, Maharashtra (IN); Venkata P. Palle, Maharashtra (IN); Rajender Kumar Kamboj, Maharashtra (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 0 days.

(21) Appl. No.: 14/398,161

(22) PCT Filed: May 1, 2013

(86) PCT No.: PCT/IB2013/053446
§ 371 (c)(1),
(2) Date: Oct. 31, 2014

(87) PCT Pub. No.: WO2013/164773
PCT Pub. Date: Nov. 7, 2013

(65) Prior Publication Data
US 2015/0111925 A1   Apr. 23, 2015

(30) Foreign Application Priority Data

May 2, 2012  (IN) .................................. 6/KOL/2012
Dec. 28, 2012  (IN) ............................ 1474/KOL/2012

(51) Int. Cl.
*C07D 413/14* (2006.01)
*C07D 401/14* (2006.01)

(52) U.S. Cl.
CPC ............ *C07D 413/14* (2013.01); *C07D 401/14* (2013.01)

(58) Field of Classification Search
CPC .................................................... C07D 413/14
USPC ....................................... 546/269.4; 514/340
See application file for complete search history.

(56) References Cited

U.S. PATENT DOCUMENTS

2010/0152241 A1   6/2010  Whitten
2012/0115903 A1   5/2012  Frank et al.

FOREIGN PATENT DOCUMENTS

| | | |
|---|---|---|
| EP | 1 024 138 A1 | 8/2000 |
| WO | WO 99/51580 A1 | 10/1999 |
| WO | WO 99/62885 A1 | 12/1999 |
| WO | WO2005/009539 A2 | 2/2005 |
| WO | WO 2005/009954 A2 | 2/2005 |
| WO | WO 2006/034402 A2 | 3/2006 |
| WO | WO 2006/081389 A1 | 8/2006 |
| WO | WO 2006/081391 A2 | 8/2006 |
| WO | WO 2006/083477 A2 | 8/2006 |
| WO | WO 2007/087429 A2 | 8/2007 |
| WO | WO 2007/087441 A2 | 8/2007 |
| WO | WO 2007/087442 A2 | 8/2007 |
| WO | WO 2007/089904 A2 | 8/2007 |
| WO | WO 2009/017819 A1 | 2/2009 |
| WO | WO 2009/035818 A1 | 3/2009 |
| WO | WO 2009/076454 A2 | 6/2009 |
| WO | WO 2010/025295 A2 | 3/2010 |
| WO | WO 2010/027875 A2 | 3/2010 |
| WO | WO 2010/039238 A1 | 4/2010 |
| WO | WO 2011/034962 A2 | 3/2011 |
| WO | WO 2011/042797 A1 | 4/2011 |
| WO | WO 2012/022487 A1 | 2/2012 |
| WO | WO 2012/056478 A1 | 5/2012 |
| WO | WO 2012/151355 A1 | 11/2012 |
| WO | WO 2013/059666 A1 | 4/2013 |
| WO | WO 2013/059677 A1 | 4/2013 |

OTHER PUBLICATIONS

International Search Report for corresponding International Patent Application No. PCT/IB2013/053446 mailed Sep. 18, 2013.
Di Sabatino, A. et al., "Targeting Gut T Cell $Ca^{2+}$ Release-Activated $Ca^{2+}$ Channels Inhibits T Cell Cytokine Production and T-Box Transcription Factor T-Bet in Inflammatory Bowel Disease", *J. Immunol.*, 183: 3454-3462 (2009).
Parakh, A. et al., "Store-Operated Calcium Channels", *Physiol. Rev.*, 85: 757-810 (2005).

(Continued)

*Primary Examiner* — Patricia L Morris
(74) *Attorney, Agent, or Firm* — Merchant & Gould P.C.

(57) ABSTRACT

The present invention relates to compounds described herein Formula (I) and pharmaceutical acceptable salts thereof, which modulate the activity of calcium release-activated calcium (CRAC) channel. The invention also describes the compounds of Formula (I) and pharmaceutical compositions containing such compounds thereof for treating, managing, and/or lessening the severity of diseases, disorders, syndromes or conditions associated with the modulation of calcium release-activated calcium (CRAC) channel.

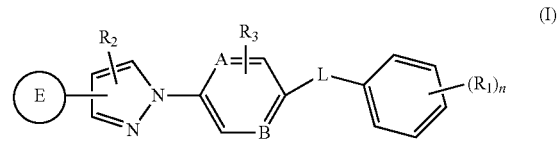

(I)

11 Claims, No Drawings

(56) References Cited

OTHER PUBLICATIONS

Fahrner, M. et al., "Mechanistic view on domains mediating STIM1-Orai coupling", *Immuno. Rev.*, 231: 99-112 (2009).
Parekh, A., "Store-operated CRAC channels: function in health and disease", *Nat. Rev.*, 9: 399-410 (2010).
Yang, S. et al., "Orai1 and STIM1 Are Critical for Breast Tumor Cell Migration and Metastasis", *Cancer Cell*, 15: 124-134 (2009).
Abeele, F. et al., "Bcl-2-dependent modulation of $Ca^{2+}$ homeostasis and store-operated channels in prostate cancer cells", *Cancer Cell*, 1: 169-179 (2002).
Motiani, R. et al., "A Novel Native Store-operated Calcium Channel Encoded by Orai3", *J. Biol. Chem.*, 285(25): 19173-19183 (2010).
Varga-Szabo, D. et al., "The calcium sensor STIM1 is an essential mediator of arterial thrombosis and ischemic brain infarction", *J. Exp. Med.*, 205(7): 1583-1591 (2008).
Braun, A. et al., "Orai 1 (CRACM1) is the platelet SOC channel and essential for pathological thrombus formation", *Blood*, 113(9): 2056-2063 (2009).
Gillo, K. et al., "Roles of Platelet STIM1 and Orai1 in Glycoprotein VI- and Thrombin-dependent Procoagulant Activity and Thrombus Formation", *J. Bio. Chem.*, 285 (31): 23629-23638 (2010).
Flores, A. et al., "Haloacetylated Enol Ethers, 19: Synthesis of 3-(2-Thienyl)-and 3-(2-Furyl)-5-trihalomethyl Substituted Azoles", *Synthesis*, 16: 2744-2750 (2005).
Flores, A. et al., "1,1,1-trihalo-4-methoxy-4-[2-heteroaryl]-3-buten-2-ones, the corresponding butan-1,3-dione and azole derivatives", *Tetrahedron Letters*, 43: 8701-8705 (2002).
Wuts, P. et al., Ed., "Greene's Protective Groups in Organic Synthesis", $4^{th}$ Ed., John Wiley & Sons, NY (2007).

SUBSTITUTED PYRAZOLE COMPOUNDS AS CRAC MODULATORS

RELATED APPLICATIONS

The present application is a National Stage Application of PCT/IB2013/053446, filed May 1, 2013, which claims the benefit of priority to Indian Provisional Patent Application No. 0006/KOL/2012, filed on May 2, 2012 and 1474/KOL/2012, filed on Dec. 28, 2012, filed in India and which applications are incorporated herein by reference. To the extent appropriate, a claim of priority is made to each of the above disclosed applications.

TECHNICAL FIELD OF THE INVENTION

The invention relates to substituted pyrazole compounds, pharmaceutically acceptable salts thereof and pharmaceutical compositions for the treatment, management, and/or lessening of severity of diseases, disorders, syndromes or conditions associated with the modulation of calcium release-activated calcium (CRAC) channel. The invention also relates to methods of treating, managing and/or lessening the severity of the diseases disorders, syndromes or conditions associated with the modulation of CRAC. The invention also relates to processes for the preparation of the compounds of the invention.

BACKGROUND OF THE INVENTION

Inflammation is the response by the body to infection, irritation or injury; wherein the immune cells of the body are activated in response to any of these stimuli. Inflammation plays a key role in many diseases not only of the immune cells such as allergy, asthma, arthritis, dermatitis, multiple sclerosis, systemic lupus but also organ transplant, diabetes, cardiovascular disease, Alzheimer's disease, Parkinson's disease, inflammatory and/or irritable bowel syndrome (Di Sabatino et. al., J. Immunol., 183, 3454-3462, 2009), psoriasis, and cancer. An initial inflammatory response to pathogens or injury is necessary and required to fight infection or heal the wound, but sustained or persistent inflammation can lead to any of the chronic disorders; characterized by the production of inflammatory cytokines as, specified above.

Inflammation is characterized by the production of different cytokines such as IL-2, IL-4, IL-10. IL-13, IL-17, IL-21, IL-23, IL-28, IFN-γ, TNF-α, etc., that have been implicated in playing a role in different diseases. Any drug which can modulate the production of these cytokines would help alleviate the disease symptoms and may also cure it.

$Ca^{+2}$ signals have been shown to be essential for diverse cellular functions in different cell types including differentiation, effector functions, and gene transcription in cells of the immune system as well as regulating the cytokine signaling pathway through calcineurin and nuclear factor of activated T cells (NFAT).

In immune cells, sustained $Ca^{+2}$ influx has been shown to be necessary for complete and long-lasting activation of calcineurin-NFAT pathways, essential for cytokine production. Engagement of receptors such as T-cell antigen receptor (TCR), the B-cell antigen receptor (BCR), and the Fc receptors (FcR) on mast cells, macrophages, and NK cells, leads to the tyrosine phosphorylation and activation of phospholipase C-γ (PLC-γ). PLC-γ hydrolyzes phosphatidylinositol-3,4-bi-phosphate ($PIP_2$) to the second messengers, inositol-1,4,5-triphosphate ($IP_3$) and diacylglycerol (DAG). $IP_3$ binds to $IP_3$ receptors ($IP_3R$) in the membrane of the endoplasmic reticulum (ER) and induces the release of ER $Ca^{+2}$ stores into the cytoplasma. The decrease in the $Ca^{+2}$ concentration in the ER induces store-operated $Ca^{+2}$ entry (SOCE) through plasma membrane $Ca^{+2}$ channels. SOCE through highly $Ca^{+2}$-selective $Ca^{+2}$ release-activated $Ca^{+2}$ (hereinafter, CRAC) channels constitutes the major pathway of intracellular $Ca^{+2}$ entry in T cells, B cells, macrophages, mast cells, and other cell types (Parekh and Putney, Physiol. Rev., 85, 757-810, 2005).

The CRAC channel is comprised of two family proteins, one which functions in sensing $Ca^{+2}$ levels in the ER—the stromal interacting molecules (STIM)-1 and -2 and the other which is a pore-forming protein—Orai1, 2 and 3. The STIM proteins are single transmembrane proteins localized on the ER membrane with their N-termini oriented toward the lumen and containing an EF-hand $Ca^{+2}$ binding motif. Depletion of $Ca^{+2}$ from the ER causes $Ca^{+2}$ to dissociate from STIM, which causes a conformational change that promotes oligomerization and migration of STIM molecules to closely apposed ER-plasma membrane junctions. At the junctions, the STIM oligomers interact with the Orai proteins. In resting cells, Orai channels are dispersed across the plasma membrane and on depletion of $Ca^{+2}$ from the stores, they aggregate in the vicinity of the STIM punctae. The eventual increase in intracellular $Ca^{+2}$ concentration activates the calcineurin-NFAT pathway. NFAT activates transcription of several genes including cytokine genes such as IL-2, etc along with other transcription factors such as AP-1, NFκB and Foxp3 (Fahmer et. al., Immuno. Rev., 231, 99-112, 2009).

The role of CRAC channel in different diseases such as allergy, inflammatory bowel disease, thrombosis and breast cancer has been reported in literature (Parekh, Nat. Rev., 9, 399-410, 2010). It has been reported in the art that STIM1 and Orai1 are essential in in vitro tumor cell migration and in vivo tumor metastasis. Thus the involvement of store operated $Ca^{2+}$ entry in tumor metastasis renders STIM1 and Orai1 proteins potential targets for cancer therapy (Yang et.al., Cancer Cell, 15, 124-134, 2009). Additional literature available on the involvement of CRAC channel in cancer are Abeele et. al., Cancer Cell, 1, 169-179, 2002, Motiani et al., J. Biol. Chem., 285; 25, 19173-19183, 2010.

Recent literature reports the role of STIM1 and Orai1 in collagen dependent arterial thrombosis in mice in vivo and that deficiency in either protects against collagen dependent arterial thrombus formation as well as brain infarction (Varga-Szabo et. al., J. Exp. Med., 205, 1583-1591, 2008; Braun et. al., Blood, 113, 2056-2063, 2009). The role of STIM1-Orai1 mediated SOCE in thrombus formation makes Orai1 a potential target for treatment of thrombosis and related conditions (Gillo et. al., JBC, 285; 31, 23629-23638, 2010).

As the Orai pore channel proteins have been shown to be essential for transmitting the signal induced by the binding of antigens to the cellular receptors on the immune cells, a potential Orai channel interacting drug would be able to modulate the signaling thereby impacting the secretion of the cytokines involved in, as mentioned hereinbefore, inflammatory conditions, cancer, allergic disorders, immune disorders, rheumatoid arthritis, cardiovascular diseases, thrombocytopathies, arterial and/or venous thrombosis and associated or related conditions which can be benefitted by the CRAC channel modulatory properties of the compounds described herein.

Several compounds have been reported in the art as CRAC channel modulators. For example, patent application publications WO2005009539, WO2005009954, WO2006081391, WO2006081389, WO2006034402, WO2006083477, WO2007087441, WO2007087442, WO2007087429, WO2007089904, WO2009017819, WO2009076454, WO2009035818, US20100152241, WO2010039238, WO2010025295, WO2010027875, WO2011034962, WO2012151355, WO2013059666, WO2013059677 disclose the compounds for modulating CRAC channels.

SUMMARY OF THE INVENTION

In accordance with one aspect, the invention provides the compounds of Formula (I):

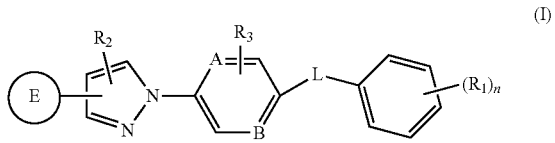

wherein, one of A and B is N and the other is $CR_3$;

L is selected from $-C(O)NR_{11}-$, $-NR_{11}C(O)-$, $-CR_aR_bNR_{11}-$ and $-NR_{11}CR_aR_b-$;

at each occurrence, $R_a$ and $R_b$ are independently hydrogen, substituted or unsubstituted alkyl or halogen;

ring E is 5 membered non aromatic heterocyclic ring selected from Formula (a) to (c)

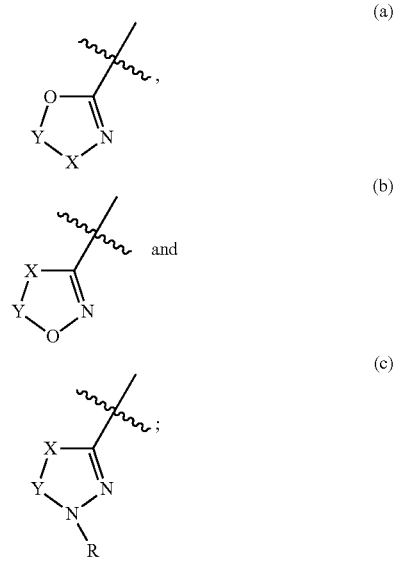

at each occurrence, X is selected from $-C(O)-$, $-CR_4R_5-$ and $-NR-$;

at each occurrence, Y is $-C(O)-$ or $-CR_4R_5-$;

provided that both of X and Y are not simultaneously $-C(O)-$;

R is selected from substituted or unsubstituted alkyl, substituted or unsubstituted haloalkyl, substituted or unsubstituted cycloalkyl, substituted or unsubstituted cycloalkenyl, substituted or unsubstituted aryl, substituted or unsubstituted heteroaryl, substituted or unsubstituted heterocyclyl, $-C(O)NR_6R_7$, $-C(O)OR_9$ and $-C(O)R_8$;

$R_1$, which may be same or different at each occurrence, is independently selected from halogen, cyano, nitro, hydroxyl, substituted or unsubstituted alkyl, substituted or unsubstituted haloalkyl, substituted or unsubstituted alkoxy, substituted or unsubstituted haloalkoxy, substituted or unsubstituted cycloalkyl, substituted or unsubstituted cycloalkoxy, $-NR_6R_7$, $-NHC(O)R_8$, and $-C(O)OR_9$; or any two of adjacent $R_1$ groups together with the phenyl to which they are attached form substituted or unsubstituted naphthalene ring;

$R_2$ is selected from halogen, cyano, nitro, hydroxyl, substituted or unsubstituted alkyl, substituted or unsubstituted haloalkyl, substituted or unsubstituted alkoxy, substituted or unsubstituted haloalkoxy, substituted or unsubstituted cycloalkyl, substituted or unsubstituted cycloalkoxy, $-NR_6R_7$, $-NHC(O)R_8$, and $-C(O)OR_9$;

$R_3$ is selected from hydrogen, halogen, cyano, nitro, hydroxyl, substituted or unsubstituted alkyl, substituted or unsubstituted haloalkyl, substituted or unsubstituted alkoxy, substituted or unsubstituted haloalkoxy, substituted or unsubstituted cycloalkyl, substituted or unsubstituted cycloalkoxy, $-NR_6R_7$, $-NHC(O)R_8$, and $-C(O)OR_9$;

$R_4$ and $R_5$, which may be same or different at each occurrence, are independently selected from hydrogen, halogen, $-OR_{10}$, substituted or unsubstituted alkyl, substituted or unsubstituted haloalkyl, substituted or unsubstituted hydroxyalkyl, $-C(O)OR_9$, $-C(O)-NR_6R_7$, substituted or unsubstituted cycloalkyl, substituted or unsubstituted aryl, substituted or unsubstituted heteroaryl and substituted or unsubstituted heterocyclyl; provided that, when any of $R_4$ or $R_5$ in Y is $-OR_{10}$ then $R_{10}$ is not hydrogen;

$R_6$ and $R_7$, which may be same or different at each occurrence, are independently selected from hydrogen, substituted or unsubstituted alkyl and substituted or unsubstituted cycloalkyl; or $R_6$ and $R_7$, together with the nitrogen atom to which they are attached, may form a substituted or unsubstituted, saturated or unsaturated 3 to 12 membered cyclic ring, wherein the unsaturated cyclic ring may have one or two double bonds;

$R_8$, which may be same or different at each occurrence, is independently selected from substituted or unsubstituted alkyl, substituted or unsubstituted alkenyl, substituted or unsubstituted cycloalkyl, and substituted or unsubstituted aryl;

$R_9$, which may be same or different at each occurrence, is independently selected from hydrogen, substituted or unsubstituted alkyl and substituted or unsubstituted aryl;

$R_{10}$ is selected from hydrogen, substituted or unsubstituted alkyl, substituted or unsubstituted cycloalkyl, substituted or unsubstituted aryl, substituted or unsubstituted heteroaryl and substituted or unsubstituted heterocyclyl;

at each occurrence, $R_{11}$ is independently hydrogen or substituted or unsubstituted alkyl; and n is an integer ranging from 0 to 4, both inclusive;

or a pharmaceutically acceptable salt thereof.

According to one embodiment, there are provided compounds having the Formula (II):

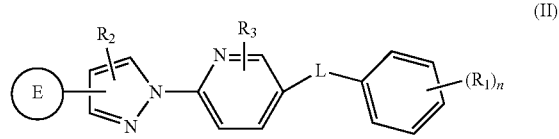

or a pharmaceutically acceptable salt thereof;

wherein ring E, $R_1$, $R_2$, $R_3$, L and 'n' are as defined herein above.

According to another embodiment, there are provided compounds having Formula (III):

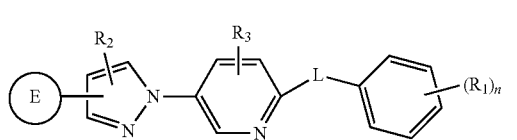
(III)

or a pharmaceutically acceptable salt thereof;

wherein ring E, $R_1$, $R_2$, $R_3$, L and 'n' are as defined herein above.

It should be understood that the Formula (I), Formula (II) and Formula (III) structurally encompasses all tautomers, stereoisomers, enantiomers and diastereomers, including isotopes wherever applicable and pharmaceutically acceptable salts that may be contemplated from the chemical structure of the genera described herein.

The details of one or more embodiments of the invention set forth in the below are illustrative in nature only and not intended to limit to the scope of the invention. Other features, objects and advantages of the inventions will be apparent from the description and claims.

According to one embodiment there are provided a compound of Formula (I) wherein ring

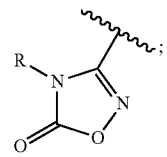

is selected from Formula (i) to (iv)

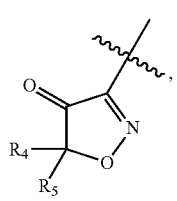
(i)

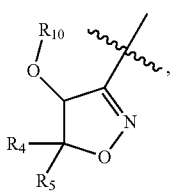
(ii)

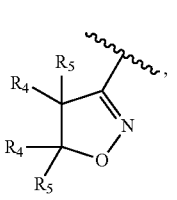
(iii)

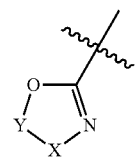
(iv)

where R, $R_4$, $R_5$ and $R_{10}$ are as defined herein above.

According to another embodiment there are provided a compound of Formula (I) wherein ring

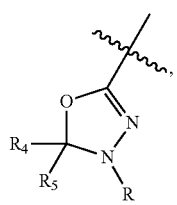

is selected from Formula (v) to (vii)

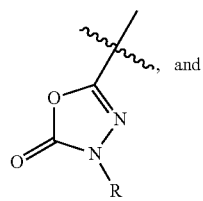
(v)

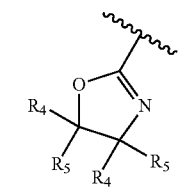
, and (vi)

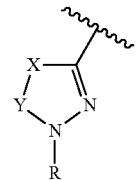
(vii)

where R, $R_4$, and $R_5$ are as defined herein above.

According to one embodiment there are provided a compound of Formula (I) wherein ring is selected from Formula (viii) to (x)

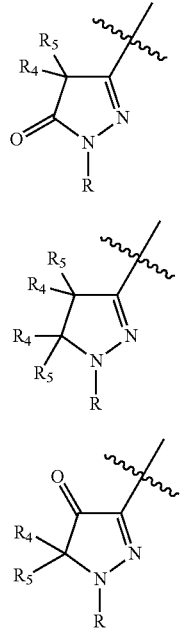

where R, $R_4$, and $R_5$ are as defined herein above.

According to another embodiment are provided compounds of Formula (I), (II) and/or (III) in which L is selected from —C(O)NR$_{11}$-, —NR$_{11}$C(O)— and —NR$_{11}$CR$_a$R$_b$— wherein R$_{11}$, R$_a$ and R$_b$ are independently a hydrogen or substituted or unsubstituted alkyl.

According to another embodiment are provided compounds of Formula (I), (II) and/or (III) in which R$_1$ is same or different and are independently selected from halogen, cyano, nitro, hydroxyl, substituted or unsubstituted alkyl, substituted or unsubstituted haloalkyl, substituted or unsubstituted alkoxy, substituted or unsubstituted haloalkoxy and substituted or unsubstituted cycloalkyl; and 'n' is 0, 1, 2, or 3.

According to another embodiment are provided compounds of Formula (I), (II) and/or (III) in which R$_2$ is selected from halogen, hydroxyl, cyano, nitro, substituted or unsubstituted alkyl, substituted or unsubstituted haloalkyl, substituted or unsubstituted alkoxy, substituted or unsubstituted haloalkoxy and substituted or unsubstituted cycloalkyl.

According to another embodiment are provided compounds of Formula (I), (II) and/or (III) in which R$_3$ is selected from hydrogen, halogen, cyano, nitro, hydroxyl, substituted or unsubstituted alkyl, substituted or unsubstituted haloalkyl, substituted or unsubstituted alkoxy and substituted or unsubstituted cycloalkyl.

According to another embodiment are provided compounds of Formula (I) in which one of A and B is N and the other is CH; L is —C(O)NH—, —NHC(O)— or —NHCH$_2$—; R$_1$ is same or different and are independently selected from halogen, substituted or unsubstituted alkyl, substituted or unsubstituted haloalkyl and substituted or unsubstituted cycloalkyl; 'n' is 0, 1, 2, or 3; R$_2$ is halogen, substituted or unsubstituted alkyl, substituted or unsubstituted haloalkyl or substituted or unsubstituted cycloalkyl; R$_3$ is selected from hydrogen, halogen or substituted or unsubstituted alkyl; and ring E is selected from

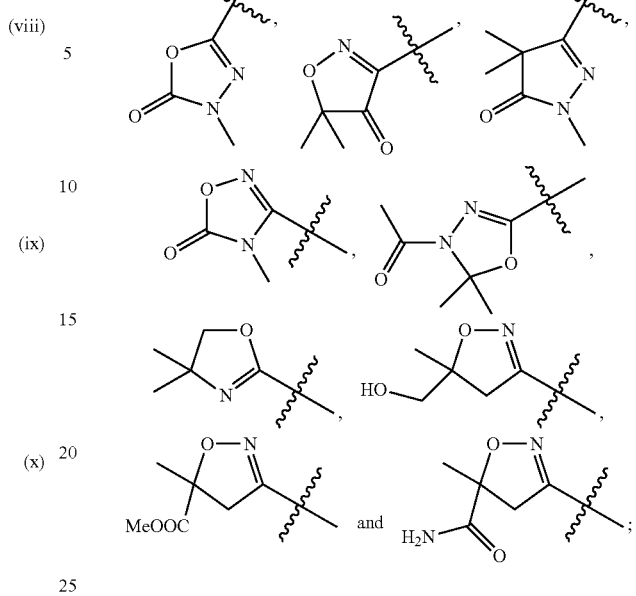

In another aspect, the invention provides a pharmaceutical composition comprising at least one compound of Formula (I) and at least one pharmaceutically acceptable excipient.

In another aspect of the invention, there is provided a compound of Formula (I) useful in treating, managing and/or lessening the severity of the diseases, disorders, syndromes or conditions associated with the modulation of CRAC channel.

In another aspect, the invention provides a pharmaceutical composition of a compound of Formula (I) useful in treating, managing and/or lessening the severity of the diseases disorders, syndromes or conditions associated with the modulation of CRAC channel in a subject in need thereof by administering to the subject, one or more compounds described herein in an amount.

In another aspect, the invention provides a method of modulating ion channel activity, for example, CRAC channel, by administering effective amount of a compound of Formula (I) and/or pharmaceutically acceptable salts.

In another aspect, the invention provides a method of modulating the secretion of cytokines, for example IL-2, IL-4, IL-10, IL-13, IL-17, IL-21, IL-23, IL-28, IFN-γ and TNF-α and the like, by regulating the cytokine signalling pathway through calcineurin and NFAT cells.

In another aspect, there are provided processes for the preparation of compounds of Formula (IIa):

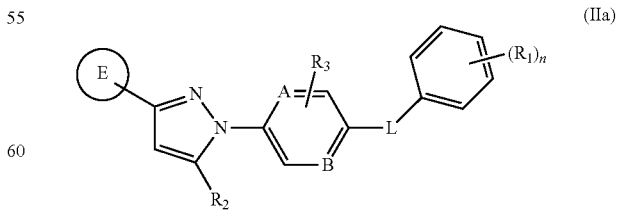

wherein L is —NR$_{11}$C(O)— or NR$_{11}$CR$_a$R$_b$;

ring E, A, B, R$_a$, R$_b$, R$_1$, R$_2$, R$_3$, R$_{11}$ and 'n' are as described herein above;

the process comprising the steps:

a) oxidizing a compound of Formula (10) where X' is halogen, NO$_2$, COOR' where R' is H, alkyl etc., by using suitable oxidation agents to give compound of Formula (11) in suitable solvent(s);

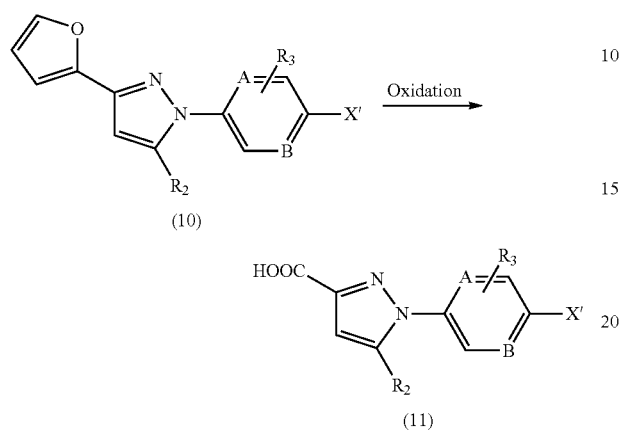

b) converting a acid compound of Formula (11) to cyclized compound of compound of Formula (12) by following acid ester formation then heterocyclic ring formation using hydrazine hydrate followed by triphosgene

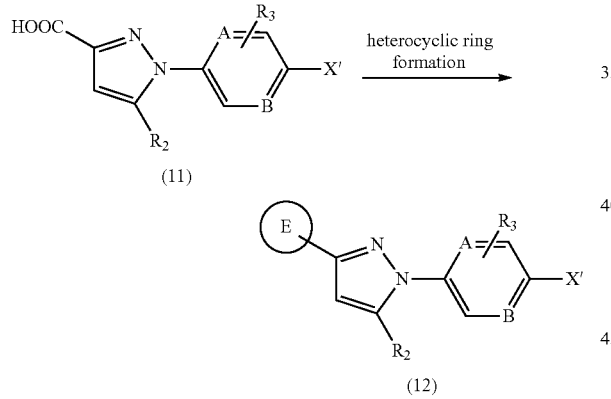

c) coupling of compound Formula (12) where X' is halogen, with compound of Formula (6) where L' is C(O) or CR$_a$R$_b$ where R$_a$, R$_b$ and R$_{11}$ are hydrogen or alkyl, to give compound of Formula (IIa) by using suitable reagents and suitable solvent.

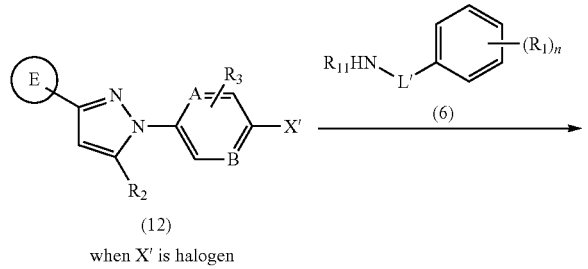

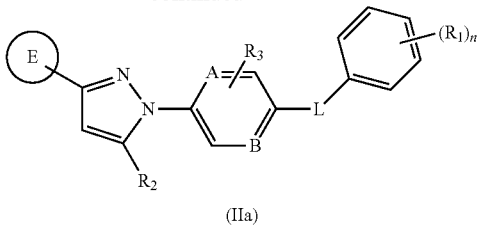

In another aspect, there are provided processes for the preparation of compounds of Formula (IIb):

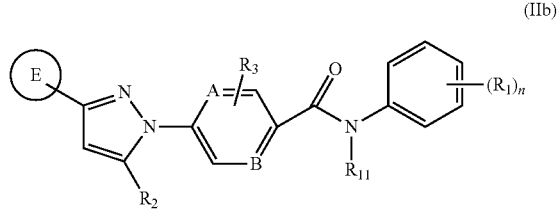

wherein ring E, A, B, R$_1$, R$_2$, R$_3$, R$_{11}$ and 'n' are as described herein above; amide coupling of compound Formula (12) where X' is COOR' where R' is H, alkyl etc., with compound of Formula (5a) to give compound of Formula (IIb) by using suitable amide coupling methods

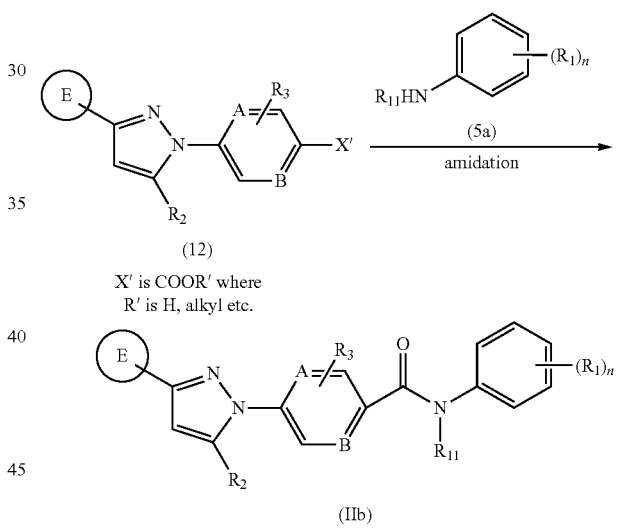

In another aspect, there are provided processes for the preparation of compounds of Formula (IIa):

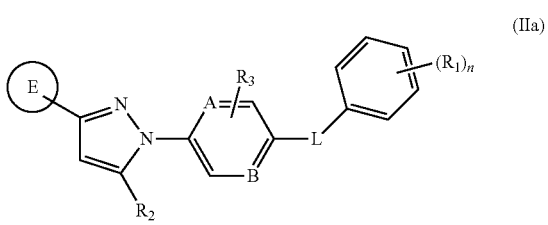

wherein L is —NR$_{11}$C(O)— or NR$_{11}$CR$_a$R$_b$;
ring E, A, B, R$_a$, R$_b$, R$_1$, R$_2$, R$_3$, R$_{11}$ and 'n' are as described herein above;
the process comprising the steps:

a) reducing a nitro group in compound of Formula (12) where X' is NO$_2$, by using suitable reducing agent to give amino compound of Formula (13) where R$_{11}$ is hydrogen, in suitable solvent

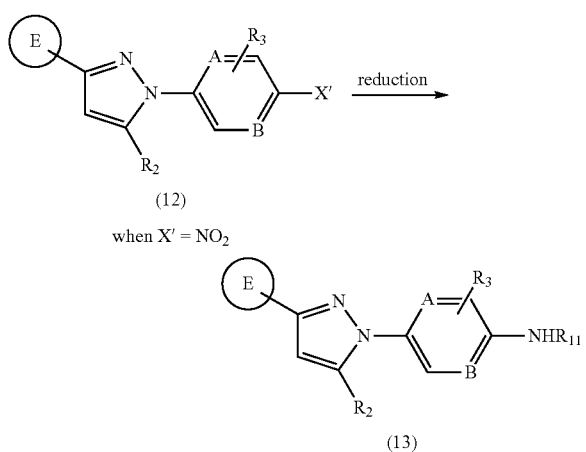

when X' = NO₂ b) coupling of compound of Formula (13) with compound of Formula (8) by using suitable amide coupling reagents or suitable reductive amidation reagents to give compound of Formula (IIa)

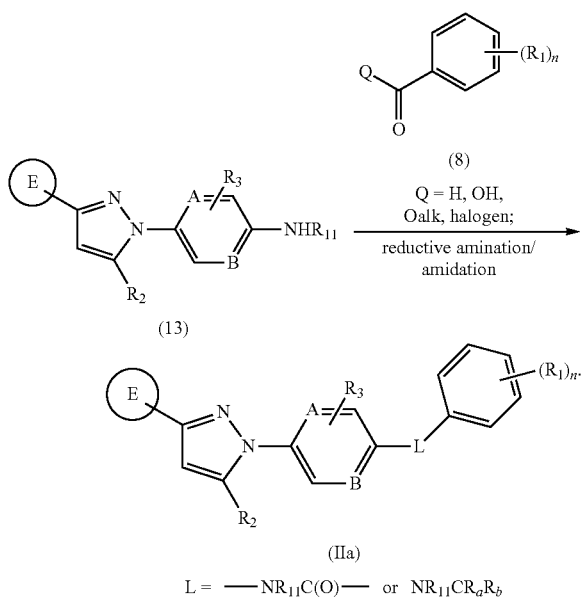

L = —NR₁₁C(O)— or NR₁₁CR$_a$R$_b$

DETAILED DESCRIPTION OF THE INVENTION

Definitions and Abbreviations:

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

Unless otherwise stated, in the present application "oxo" means C(=O) group. Such an oxo group may be a part of either a cycle or a chain in the compounds of the present invention.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched, substituted or unsubstituted.

The term "alkenyl" refers to a hydrocarbon radical containing from 2 to 10 carbon atoms and including at least one carbon-carbon double bond. Non-limiting examples of alkenyl groups include ethenyl, 1-propenyl, 2-propenyl (allyl), iso-propenyl, 2-methyl-1-propenyl, 1-butenyl, 2-butenyl and the like. Unless set forth or recited to the contrary, all alkenyl groups described or claimed herein may be straight chain or branched, substituted or unsubstituted.

The term "alkynyl" refers to a hydrocarbon radical containing 2 to 10 carbon atoms and including at least one carbon-carbon triple bond. Non- limiting examples of alkynyl groups include ethynyl, propynyl, butynyl and the like. Unless set forth or recited to the contrary, all alkynyl groups described or claimed herein may be straight chain or branched, substituted or unsubstituted.

The term "alkoxy" refers to an alkyl group attached via an oxygen linkage. Non- limiting examples of such groups are methoxy, ethoxy and propoxy and the like. Unless set forth or recited to the contrary, all alkoxy groups described or claimed herein may be straight chain or branched, substituted or unsubstituted.

The term "alkenyloxy" refers to an alkenyl group attached via an oxygen linkage. Non-limiting examples of such groups are vinyloxy, allyloxy, 1-butenyloxy, 2-butenyloxy, isobutenyloxy, 1-pentenyloxy, 2-pentenyloxy, 3-methyl-1-butenyloxy, 1-methyl-2-butenyloxy, 2,3-dimethylbutenyloxy, 1-hexenyloxy and the like. Unless set forth or recited to the contrary, all alkenyloxy groups described or claimed herein may be straight chain or branched, substituted or unsubstituted.

The term "alkynyloxy" refers to an alkynyl group attached via an oxygen linkage. Non-limiting examples of such groups are acetylenyloxy, propynyloxy, 1-butynyloxy, 2-butynyloxy, 1-pentynyloxy, 2-pentynyloxy, 3-methyl-1-butynyloxy, 1-hexynyloxy, 2-hexynyloxy, and the like. Unless set forth or recited to the contrary, all alkynyloxy groups described or claimed herein may be straight chain or branched, substituted or unsubstituted.

The term "cycloalkyl" refers to a non-aromatic mono or multicyclic ring system having 3 to 12 carbon atoms, such as cyclopropyl, cyclobutyl, cyclopentyl, cyclohexyl and the like. Examples of multicyclic cycloalkyl groups include, but are not limited to, perhydronapththyl, adamantyl and norbornyl groups, bridged cyclic groups or spirobicyclic groups, e.g., spiro(4,4)non-2-yl and the like. Unless set forth or recited to the contrary, all cycloalkyl groups described or claimed herein may be substituted or unsubstituted.

The term "cycloalkoxy" refers to an cycloalkyl, defined herein, group attached via an oxygen linkage. Non-limiting examples of such groups are cyclopropoxy, cyclobutoxy, cyclopentoxy, cyclohexyloxy and the like. Unless set forth or recited to the contrary, all alkoxy groups described or claimed herein may be straight chain or branched, substituted or unsubstituted.

The term "cycloalkenyl" refers to a non-aromatic mono or multicyclic ring system having 3 to 12 carbon atoms and including at least one carbon-carbon double bond, such as cyclopentenyl, cyclohexenyl, cycloheptenyl and the like. Unless set forth or recited to the contrary, all cycloalkenyl groups described or claimed herein may be substituted or unsubstituted.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl, etc. Unless set forth or recited to the contrary, all cycloalkylalkyl groups described or claimed herein may be substituted or unsubstituted.

The term "haloalkyl" refers to an alkyl group as defined above that is substituted by one or more halogen atoms as defined above. Preferably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Preferably, a polyhaloalkyl is substituted with up to 12 halogen atoms. Non-limiting examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms.

The term "haloalkoxy" refers to an haloalkyl, defined herein, group attached via an oxygen linkage. Non-limiting examples of such groups are monohaloalkoxy, dihaloalkoxy or polyhaloalkoxy including perhaloalkoxy. Unless set forth or recited to the contrary, all haloalkoxy groups described or claimed herein may be straight chain or branched, substituted or unsubstituted.

The term "hydroxyalkyl" refers to an alkyl group, as defined above that is substituted by one or more hydroxy groups. Preferably, the hydroxyalkyl is monohydroxyalkyl or dihydroxyalkyl. Non-limiting examples of a hydroxyalkyl include 2-hydroxyethyl, 3-hydroxypropyl, 2-hydroxypropyl, and the like.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like. Unless set forth or recited to the contrary, all aryl groups described or claimed herein may be substituted or unsubstituted.

The term "arylalkyl" refers to an aryl group as defined above directly bonded to an alkyl group as defined above, e.g., —$CH_2C_6H_5$ and —$C_2H_4C_6H_5$. Unless set forth or recited to the contrary, all arylalkyl groups described or claimed herein may be substituted or unsubstituted.

A "3-12 membered cyclic ring" as used herein refers to a monocyclic, bicyclic, polycyclic heteroaryl or heterocyclic ring systems. Thease heteroaryl or heterocyclic ring as described herein.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s), and one or two carbon atoms(s) in the heterocyclic ring or heterocyclyl may be interrupted with —$CF_2$—, —C(O)—, —S(O)—, $S(O)_2$, —C(=N-alkyl)-, or —C(=N-cycloalkyl), etc. In addition heterocyclic ring may also be fused with aromatic ring. Non-limiting examples of heterocyclic rings include azetidinyl, benzopyranyl, chromanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl, tetrahydropyranyl, thiazolinyl, thiazolidinyl, thiamorpholinyl, thiamorpholinyl sulfoxide, thiamorpholinyl sulfone indoline, benzodioxole, tetrahydroquinoline, tetrahydrobenzopyran and the like. The heterocyclic ring may be attached by any atom of the heterocyclic ring that results in the creation of a stable structure. Unless set forth or recited to the contrary, all heterocyclyl groups described or claimed herein may be substituted or unsubstituted; substituents may be on same or different ring atom.

The term "heteroaryl" unless otherwise specified, refers to a substituted or unsubstituted 5- to 14-membered aromatic heterocyclic ring with one or more heteroatom(s) independently selected from N, O or S. The heteroaryl may be a mono-, bi- or tricyclic ring system. The heteroaryl ring may be attached by any atom of the heteroaryl ring that results in the creation of a stable structure. Non-limiting examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like. Unless set forth or recited to the contrary, all heteroaryl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more substituents attached to the structural skeleton of the group or moiety. Such substituents include, but are not limited to hydroxy, halogen, carboxyl, cyano, nitro, oxo (=O), thio (=S), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, —$C(O)OR^x$, —$C(O)R^x$, —$C(S)R^x$, —$C(O)NR^xR^y$, —$NR^xC(O)NR^yR^z$, —$N(R^x)S(O)R^y$, —$N(R^x)S(O)_2R^y$, —$NR^xRY$, —$NR^xC(O)R^y$, —$NR^xC(S)R^y$, —$NR^xC(S)NR^yR^z$, —$S(O)_2NR^xR^y$, —$OR^x$, —$OC(O)R^x$, —$OC(O)NR^xR^y$, —$R^xC(O)OR^y$, —$R^xC(O)NR^yR^z$, —$R^xC(O)R^y$, —$SR^x$, and —$S(O)_2R^x$; wherein each occurrence of $R^x$, $R^y$ and $R^z$ are independently selected from hydrogen, halogen, alkyl, haloalkyl, alkenyl, alkynyl, aryl, arylalkyl, cycloalkyl, cycloalkenyl, heteroaryl, heterocyclic ring, heterocyclylalkyl and heteroarylalkyl. The aforementioned "substituted" groups cannot be further substituted. For example, when the substituent on "substituted alkyl" is "aryl" or "alkenyl", the aryl or alkenyl cannot be substituted aryl or substituted alkenyl, respectively.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable minor images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

A "Tautomer" refers to a compound that undergo rapid proton shifts from one atom of the compound to another atom of the compound. Some of the compounds described herein may exist as tautomers with different points of attachment of hydrogen. The individual tautomers as well as mixture thereof are encompassed with compounds of Formula (I).

The term "treating" or "treatment" of a state, disease, disorder, condition or syndrome includes: (a) delaying the appearance of clinical symptoms of the state, disease, disorder, condition or syndrome developing in a subject that may be afflicted with or predisposed to the state, disease, disorder, condition or syndrome but does not yet experience or display clinical or subclinical symptoms of the state, disease, disorder, condition or syndrome; (b) inhibiting the state, disease, disorder, condition or syndrome, i.e., arresting or reducing the development of the disease or at least one clinical or subclinical symptom thereof; c) lessening the severity of a disease disorder or condition or at least one of its clinical or subclinical symptoms thereof; and/or (d) relieving the disease, i.e., causing regression of the state, disorder or condition or at least one of its clinical or subclinical symptoms.

The term "modulate" or "modulating" or "modulation" refers to a decrease or inhibition in the amount, quality, or effect of a particular activity, function or molecule; by way of illustration that block or inhibit calcium release-activated calcium (CRAC) channel. Any such modulation, whether it be partial or complete inhibition is sometimes referred to herein as "blocking" and corresponding compounds as "blockers". For example, the compounds of the invention are useful as modulators of the CRAC channel.

The term "subject" includes mammals, preferably humans and other animals, such as domestic animals; e.g., household pets including cats and dogs.

A "therapeutically effective amount" means the amount of a compound that, when administered to a subject for treating a disease, disorder, syndrome or condition, is sufficient to cause the effect in the subject which is the purpose of the administration. The "therapeutically effective amount" will vary depending on the compound, the disease and its severity and the age, weight, physical condition and responsiveness of the subject to be treated.

Unless otherwise stated, in the present application "protecting group" refers to the groups intended to protect an otherwise labile group, e.g., an amino group, a carboxy group and the like, under specific reaction conditions. Various protecting groups alongwith the methods of protection and deprotection are generally known to a person of ordinary skilled in the art. Incorporated herein in this regard as reference is *Greene's Protective Groups in Organic Synthesis*, 4th Edition, John Wiley & Sons, New York. In the present invention, preferred amino protecting groups are t-butoxycarbonyl, benzyloxycarbonyl, acetyl and the like; while preferred carboxy protecting groups are esters, amides and the like.

Pharmaceutically Acceptable Salts:

The compounds of the invention may form salts with acid or base. The compounds of invention may be sufficiently basic or acidic to form stable nontoxic acid or base salts, administration of the compound as a pharmaceutically acceptable salt may be appropriate. Non-limiting examples of pharmaceutically acceptable salts are inorganic, organic acid addition salts formed by addition of acids including hydrochloride salts. Non-limiting examples of pharmaceutically acceptable salts are inorganic, organic base addition salts formed by addition of bases. The compounds of the invention may also form salts with amino acids. Pharmaceutically acceptable salts may be obtained using standard procedures well known in the art, for example by reacting a sufficiently basic compound such as an amine with a suitable acid affording a physiologically acceptable anion.

With respect to the overall compounds described by the Formula (I), the invention extends to these stereoisomeric forms and to mixtures thereof. To the extent prior art teaches synthesis or separation of particular stereoisomers, the different stereoisomeric forms of the invention may be separated from one another by a method known in the art, or a given isomer may be obtained by stereospecific or asymmetric synthesis or chiral HPLC (high performance liquid chromatography. Tautomeric forms and mixtures of compounds described herein are also contemplated.

Pharmaceutical Compositions:

The invention relates to pharmaceutical compositions containing the compound of Formula (I). In particular, the pharmaceutical compositions contain a therapeutically effective amount of at least one compound of Formula (I) and at least one pharmaceutically acceptable excipient (such as a carrier or diluent). Preferably, the pharmaceutical compositions include the compound(s) described herein in an amount sufficient to modulate the calcium release-activated calcium (CRAC) channel to treat CRAC channel mediated diseases such as inflammatory diseases, autoimmune diseases, allergic disorders, organ transplant, cancer and cardiovascular disorders when administered to a subject.

The compound of the invention may be incorporated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes a pharmaceutical agent that does not itself induce the production of antibodies harmful to the individual receiving the composition, and which may be administered without undue toxicity.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be Formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be administered in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral Formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid Formulations include, but are not limited to, syrups, emulsions, suspensions, solutions, soft gelatin and sterile injectable liquids, such as aqueous or non- aqueous liquid suspensions or solutions. For parenteral application, particularly suitable are injectable solutions or suspensions, preferably aqueous solutions with the active compound dissolved in polyhydroxylated castor oil.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

For administration to human patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 10000 mg, more typically 1.0 mg to 1000 mg, and most typically 10 mg to 500 mg, according to the potency of the active component or mode of administration.

Suitable doses of the compounds for use in treating the diseases disorders, syndromes and conditions described herein can be determined by those skilled in the relevant art.

Therapeutic doses are generally identified through a dose ranging study in humans based on preliminary evidence derived from the animal studies. Doses must be sufficient to result in a desired therapeutic benefit without causing unwanted side effects for the patient. For example, the daily dosage of the CRAC channel modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Method of Treatment

In a further embodiment, the invention is directed to the treatment or prophylaxis of inflammatory conditions by administering an effective amount of a compound of the present invention.

Inflammation is part of the normal host response to infection and injury or exposure to certain substances prone to cause it. Inflammation begins with the immunologic process of elimination of invading pathogens and toxins to repair damaged tissue. Hence, these responses are extremely ordered and controlled. However, excessive or inappropriate inflammation contributes to a range of acute and chronic human diseases and is characterized by the production of inflammatory cytokines, arachidonic acid—derived eicosanoids (prostaglandins, thromboxanes, leukotrienes, and other oxidized derivatives), other inflammatory agents (e.g., reactive oxygen species), and adhesion molecules. As used herein, the term "inflammatory conditions" is defined as a disease or disorder or abnormality characterized by involvement of inflammatory pathways leading to inflammation, and which may result from, or be triggered by, a dysregulation of the normal immune response.

The compound(s) of the present invention are useful in treatment of inflammatory conditions including, but not limited to, diseases of many body systems such as (musculoskeletal) arthritis, myositis, rheumatoid arthritis, osteoarthritis, gout, gouty arthritis, acute pseudogout, Reiter's syndrome, ankylosing spondylitis, psoriatic arthritis, dermatomyositis; (pulmonary) pleuritis, pulmonary fibrosis or nodules, restrictive lung disease, chronic obstructive pulmonary disease (COPD), acute respiratory distress syndrome (ARDS), (cardiovascular) aortic valve stenosis, restenosis, arrhythmias, coronary arteritis, myocarditis, pericarditis, Raynaud's phenomenon, systemic vasculitis, angiogenesis, atherosclerosis, ischaemic heart disease, thrombosis, myocardial infarction; (gastrointestinal) dysmotility, dysphagia, inflammatory bowel diseases, pancreatitis, (genitourinary) interstitial cystitis, renal tubular acidosis, urosepsis, (skin) purpura, vasculitis scleroderma, eczema, psoriasis, (neurologic) central nervous system disorders, cranial and peripheral neuropathies, peripheral neuropathy, radiculopathy, spinal cord or cauda equina compression with sensory and motor loss, multiple sclerosis (MS) (mental) cognitive dysfunction, Alzheimer's disease, (neoplastic) lymphoma, inflammation associated with cancer, (ophthalmologic) iridocyclitis, keratoconjunctivitis sicca, uveitis, (hematologic) chronic anemia, thrombocytopenia, (renal) amyloidosis of the kidney, glomerulonephritis, kidney failure and other diseases such as tuberculosis, leprosy, sarcoidosis, syphilis, Sjogren's syndrome, cystitis, fibromyalgia, fibrosis, septic shock, endotoxic shock, surgical complications, systemic lupus erthymotosus (SLE), transplantation associated arteriopathy, graft vs. host reaction, allograft rejection, chronic transplant rejection.

The inflammatory bowel diseases also include Crohn's disease, ulcerative colitis, indeterminate colitis, necrotizing enterocolitis, and infectious colitis.

"Allergic disorders" is defined as disorders/diseases that are caused by a combination of genetic and environmental factors resulting in a hypersensitivity disorder of the immune system. Allergic diseases are characterized by excessive immunoglobulin E (IgE) production, mast cell degranulation, tissue eosinophilia and mucus hypersecretion, resulting in an extreme inflammatory response. These responses also take place during infection with multicellular parasites, and are linked to the production of a characteristic set of cytokines by T helper (Th) 2 cells. For example asthma is a chronic inflammatory condition of the lungs, characterized by excessive responsiveness of the lungs to stimuli, in the form of infections, allergens, and environmental irritants. Allergic reactions can also result from food, insect stings, and reactions to medications like aspirin and antibiotics such as penicillin. Symptoms of food allergy include abdominal pain, bloating, vomiting, diarrhea, itchy skin, and swelling of the skin during hives. Food allergies rarely cause respiratory (asthmatic) reactions, or rhinitis. Insect stings, antibiotics, and certain medicines produce a systemic allergic response that is also called anaphylaxis. The main therapeutic interest around CRAC in allergic disorders, originates from its role in lymphocytes and mast cells, CRAC activation being a requirement for lymphocyte activation.

The compound(s) of the present invention are useful in treatment of allergic disorders including, but not limited to, atopic dermatitis, atopic eczema, Hay fever, asthma, urticaria (including chronic idiopathic urticaria), vernal conjunctivitis, allergic rhinoconjunctivitis, allergic rhinitis (seasonal and perennial), sinusitis, otitis media, allergic bronchitis, allergic cough, allergic bronchopulmonary aspergillosis, anaphylaxis, drug reaction, food allergies and reactions to the venom of stinging insects.

In yet another embodiment, the invention is directed to the treatment of "immune disorders" by administering an effective amount of a compound of the present invention.

The compounds of this invention can be used to treat subjects with immune disorders. As used herein, the term "immune disorder" and like terms mean a disease, disorder or condition caused by dysfunction or malfunction of the immune system as a whole or any of its components including autoimmune disorders. Such disorders can be congenital or acquired and may be characterized by the component(s) of the immune system getting affected or by the immune system or its components getting overactive Immune disorders include those diseases, disorders or conditions seen in animals (including humans) that have an immune component and those that arise substantially or entirely due to immune system-mediated mechanisms. In addition, other immune system mediated diseases, such as graft-versus-host disease and allergic disorders, will be included in the definition of immune disorders herein. Because a number of immune disorders are caused by inflammation or lead to inflammation, there is some overlap between disorders that are considered immune disorders and inflammatory disorders. For the purpose of this invention, in the case of such an overlapping disorder, it may be considered either an immune disorder or an inflammatory disorder. An autoimmune disorder is a condition that occurs when the immune system mistakenly attacks and destroys its own body cells, tissues and/or organs. This may result in temporary or permanent destruction of one or more types of body tissue, abnormal growth of an organ, changes in organ function, etc. For example, there is destruction of insulin producing cells of the pancreas in Type 1 diabetes mellitus. Different autoimmune disorders can target different tissues, organs or systems in an animal while some autoimmune disorders target different tissues, organs or systems in different animals. For example, the autoimmune reaction is directed against the gastrointestinal tract in Ulcerative colitis and the nervous system in multiple sclerosis whereas in systemic lupus erythematosus (lupus), affected tissues and organs may vary among individuals with the same disease. For example, one person with lupus may have affected skin and joints whereas another may have affected kidney, skin and lungs.

Specific autoimmune disorders that may be ameliorated using the compounds and methods of this invention include without limitation, autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland), autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome), autoimmune disorders of the nervous system (e.g., multiple sclerosis, myasthenia gravis, autoimmune neuropathies such as Guillain-Barre, and autoimmune uveitis), autoimmune disorders of the blood (e.g., autoimmune hemolytic anemia, pernicious anemia, and autoimmune thrombocytopenia) and autoimmune disorders of the blood vessels (e.g., temporal arteritis, anti-phospholipid syndrome, vasculitides such as Wegener's granulomatosis, and Behcet' s disease).

"Treatment of an immune disorder" herein refers to administering a compound or a composition of the invention alone or in combination with other agents to a subject, who has an immune disorder, a sign or symptom of such a disease or a risk factor towards such a disease, with a purpose to cure, relieve, alter, affect, or prevent such disorder or sign or symptom of such a disease, or the predisposition towards it.

In another embodiment, the invention is directed to the treatment of cancer by administering an effective amount of a compound of the present invention.

It has been reported in the art that STIM1 and Orai1 are essential in in vitro tumor cell migration and in vivo tumor metastasis. Thus the involvement of store operated $Ca^{2+}$ entry in tumor metastasis renders STIM1 and Orai 1 proteins potential targets for cancer therapy (Yang et.al., Cancer Cell, 15, 124-134, 2009). Additional literature available on the involvement of CRAC channel in cancer are Abeele et. al., Cancer Cell, 1, 169-179, 2002, Motiani et al., J. Biol. Chem., 285; 25, 19173-19183, 2010.

The compound(s) of the present invention may be useful in treatment of cancers and/or its metastasis including, but not limited to, breast cancer, lung cancer, pancreatic cancer, ovarian cancer, colon cancer, neck cancer, kidney cancer, bladder cancer, thyroid, blood cancer, skin cancer and the like. In yet another embodiment, the invention is directed to the treatment or prophylaxis of allergic disorders by administering an effective amount of a compound of the present invention.

In yet another embodiment, the invention is directed to the treatment or prophylaxis of cardiovascular diseases or disorders by administering an effective amount of a compound of the present invention.

The compounds of this invention can be used to treat subjects with cardiovascular disorders. "Cardiovascular disorder" refers to a structural and functional abnormality of the heart and blood vessels, comprised of diseases including but not limited to, atherosclerosis, coronary artery disease, arrhythmia, heart failure, hypertension, diseases of the aorta and its branches, disorders of the peripheral vascular system, aneurysm, endocarditis, pericarditis, heart valve disease. It may be congenital or acquired. One of the main pathological feature of all these diseases is clogged and hardened arteries, obstructing the blood flow to the heart. The effects differ depending upon which vessels are clogged with plaque. The arteries carrying oxygen rich blood, if clogged, result in coronary artery disease, chest pain or heart attack. If the arteries reaching the brain are affected, it leads to transient ischemic attack or stroke. If the vessels in arms or legs are affected, leads to peripheral vascular disease. Because a number of cardiovascular diseases may also be related to or arise as a consequence of thrombocytopathies, there is some overlap between disorders that are considered under heading cardiovascular disorders and thrmobocytopathies. For the purpose of this invention, in the case of such an overlapping disorder, it may be considered either a cardiovascular disorder or a thrombocytopathy.

STIM1 is located on the endoplasmic reticulum (ER) and functions as a calcium sensor. Orai1 is a pore forming subunit of calcium channel located on the plasma membrane, the depletion of calcium in the endoplasmic reticulum is sensed by STIM1, and calcium enters via Orai1 to refill the endoplasmic reticulum. This pathway of filling the calcium is called store operated calcium entry (SOCE), which plays an important role in calcium homeostasis, cellular dysfunction and has a significant importance in cardiovascular diseases. In cardiomyocytes, calcium is not only involved in excitation-contraction coupling but also acts as a signalling molecule promoting cardiac hypertrophy. Hypertrophic hearts are susceptible to abnormalities of cardiac rhythm and have impaired relaxation. Vascular smooth muscle cells (VSMCs) are responsible for the maintenance of vascular tone. VSMCs disorders, usually manifested as a phenotype change, are involved in the pathogenesis of major vascular diseases such as atherosclerosis, hypertension and restenosis. SOCE was also found increased in metabolic syndrome (MetS) swine coronary smooth muscle cells. The compound of this invention can be used to treat neointimal hyperplasia, occlusive vascular diseases, MetS—which is a combination of medical disorders including coronary artery disease, stroke and type 2 diabetes, abdominal aortic aneurysm, angina, transient ischemic attack, stroke, peripheral artery occlusive disease which includes inflammation, complement activation, fibrinolysis, angiogenesis and/or diseases related to FXII-induced kinin formation such as hereditary angioedema, bacterial infection of the lung, trypanosome infection, hypotensive shock, pancreatitis, chagas disease, thrombocytopenia or articular gout, myocardial infarction, portal vein thrombosis which leads to hypertension, pulmonary hypertension, deep vein thrombosis, jugular vein thrombosis, systemic sepsis, pulmonary embolism, and papilledema, Budd-Chiari syndrome, Paget-Schroetter disease, cerebral venous sinus thrombosis ischemic cardiomyopathy, hypertrophic cardiomyopathy, arrhythmogenic right ventricular cardiomyopathy, Prinzmetal angina, angina pectoris, chronic venous insufficiency, acute coronary syndrome, endocarditis, conceptual apraxia, pulmonary valve stenosis, thrombophlebitis, ventricular tachycardia, temporal arteritis, tachycardia, paroxysmal atrial fibrillation, persistent atrial fibrillation, permanent atrial fibrillation, respiratory sinus arrhythmia, carotid artery dissection, cerebrovascular diseases include, hemorrhagic stroke and ischemic stroke (where the thrombo-inflammatory cascade results in infarct growth), cardiomegaly, endocarditis, pericarditis, pericardial effusion. Valvular heart disease, vascular diseases or vascular inflammation is the result of ruptured atherosclerotic plaque which initiates thrombus formation. Platelet activation play an important role in vascular inflammation leading to myocardial infarction and ischaemic stroke, the compound of this invention will prevent platelet activation and plaque formation and would also be useful to treat all peripheral vascular diseases (PVD), pulmonary thromboembolism, and venous thrombosis.

"Treatment of cardiovascular disorders" herein refers to administering a compound or a composition of the invention alone or in combination with other agents to a subject, who has a cardiovascular disease, a sign or symptom of such a disease or a risk factor towards such a disease, with a purpose to cure, relieve, alter, affect, or prevent such disorder or sign or symptom of such a disease, or the predisposition towards it.

In yet another embodiment, the invention is directed to the treatment of "thrombocytopathies" by administering an effective amount of a compound of the present invention.

Thrombocytopathies: The compounds of this invention can be used to treat subjects with thrombocytopathies. Thrombocytopathy is an abnormality of platelets or its functions. It may be congenital or acquired. It may cause a thrombotic or a bleeding tendency or may be part of a wider disorder such as myelodysplasia. Thrombocytopathies include such vascular disorders that arise due to dysfunction of platelets or coagulation system or diseases or complications that arise as a result of partial or complete restriction of blood flow to different organs or systems due to such thrombocytopathies. Thrombocytopathies will thus include without limitation; diseases due to superficial vein thrombosis, diseases due to deep vein thrombosis, diseases due to arterial thrombosis, peripheral vascular diseases, thrombophilia, thrombophlebitis, embolisms, thromboembolism, ischemic cardiovascular diseases including but not limited to myocardial ischemia, angina, ischemic cerebrovascular diseases including but not limited to stroke, transient ischemia attack, cerebral venous sinus thrombosis (CYST) and complications arising due to thrmobocytopathies. Besides this, the disorder related to venous or arterial thrombus formation can be inflammation, complement activation, fibrinolysis, angiogenesis and/or diseases related to FXII-induced kinin formation such as hereditary angioedema, bacterial infection of the lung, trypanosome infection, hypotensive shock, pancreatitis, chagas disease, thrombocytopenia or articular gout.

Under normal circumstances, when the endothelial cells lining blood vessels are breached, platelets interact with von Willebrand factor (vWF) via the membrane glycoprotein Ib complex to help seal the breach. Glycoprotein IIb/Ia complex attracts other platelets, which combine to form aggregates. The platelets contain granules which break down to release fibrinogen, vWF, platelet-derived growth factor adenosine 5'-diphosphate (ADP), calcium and 5-hydroxytryptamine (5-HT)—serotonin. All this helps to promote the formation of a haemostatic plug (primary haemostasis). Activated platelets also synthesise thromboxane A2 from arachidonic acid as well as presenting negatively charged phospholipids on the outer leaflet of the platelet membrane bilayer. This negative surface provides binding sites for enzymes and cofactors of the coagulation system. The total effect is therefore to stimulate the coagulation system to form a clot (secondary haemostasis).

Thus physiological platelet activation and thrombus formation are essential to stop bleeding in case of vascular injury, whereas under pathological conditions this may lead to vessel occlusion due to inadequate triggering of the same process in diseased vessels leading to thrombosis, thromboembolism or tissue ischemia of vital organs. A central step in platelet activation is agonist-induced elevation of the intracellular Ca(2+) concentration. This happens on the one hand through the release of Ca(2+) from intracellular stores and on the other hand through Ca(2+) influx from the extracellular space. In platelets, the major Ca(2+) influx pathway is through store operated Ca(2+) entry (SOCE), induced by store depletion. STIM1 is the the Ca(2+) sensor in the endoplasmic reticulum (ER) membrane, whereas Orai1 is the major store operated Ca(2+) (SOC) channel in the plasma membrane, which play a key role in platelet SOCE.

"Treatment of thrombocytopathy" herein refers to administering a compound or a composition of the invention alone or in combination with other agents to a subject, who has a thrombocytopathy, a sign or symptom or complication of such a disease or a risk factor towards such a disease, with the purpose to cure, relieve, alter, affect, or prevent such a disorder or sign or symptom, or the predisposition towards it.

General Methods of Preparation

The compounds of the present invention, including compounds of general Formula (I) and specific examples are prepared through the reaction sequences illustrated in synthetic Schemes 1 to 4 wherein A, B, L, $R_1$, $R_2$, $R_3$, ring E and 'n' are as defined herein above. Starting materials are commercially available or may be prepared by the procedures described herein or by the procedures known in the art. Furthermore, in the following synthetic schemes, where specific acids, bases, reagents, coupling agents, solvents, etc., are mentioned, it is understood that other bases, acids, reagents, coupling agents, solvents etc., known in the art may also be used and are therefore included within the scope of the present invention. Variations in reaction conditions and parameters like temperature, pressure, duration of reaction, etc., which may be used as known in the art are also within the scope of the present invention. All the isomers of the compounds described in these schemes, unless otherwise specified, are also encompassed within the scope of this invention.

The compounds obtained by using the general reaction sequences may be of insufficient purity. These compounds can be purified by using any of the methods for purification of organic compounds known in the art, for example, crystallization or silica gel or alumina column chromatography using different solvents in suitable ratios. Unless mentioned otherwise, room temperature (RT) refers to a temperature in the range of 22 to 27° C.

$^1$H-NMR spectra of the compounds of the present invention were recorded using a BRUCKNER instrument (model: Avance-III), 400 MHz. Liquid chromatography—mass spectra (LCMS) of the compounds of the present invention were recorded using Agilent ion trap model 6320 and Thermo Scientific Single Quad model MSQ plus instruments. IUPAC nomenclature for the compounds of the present invention was used according to ChemBioDraw Ultra 12.0 software.

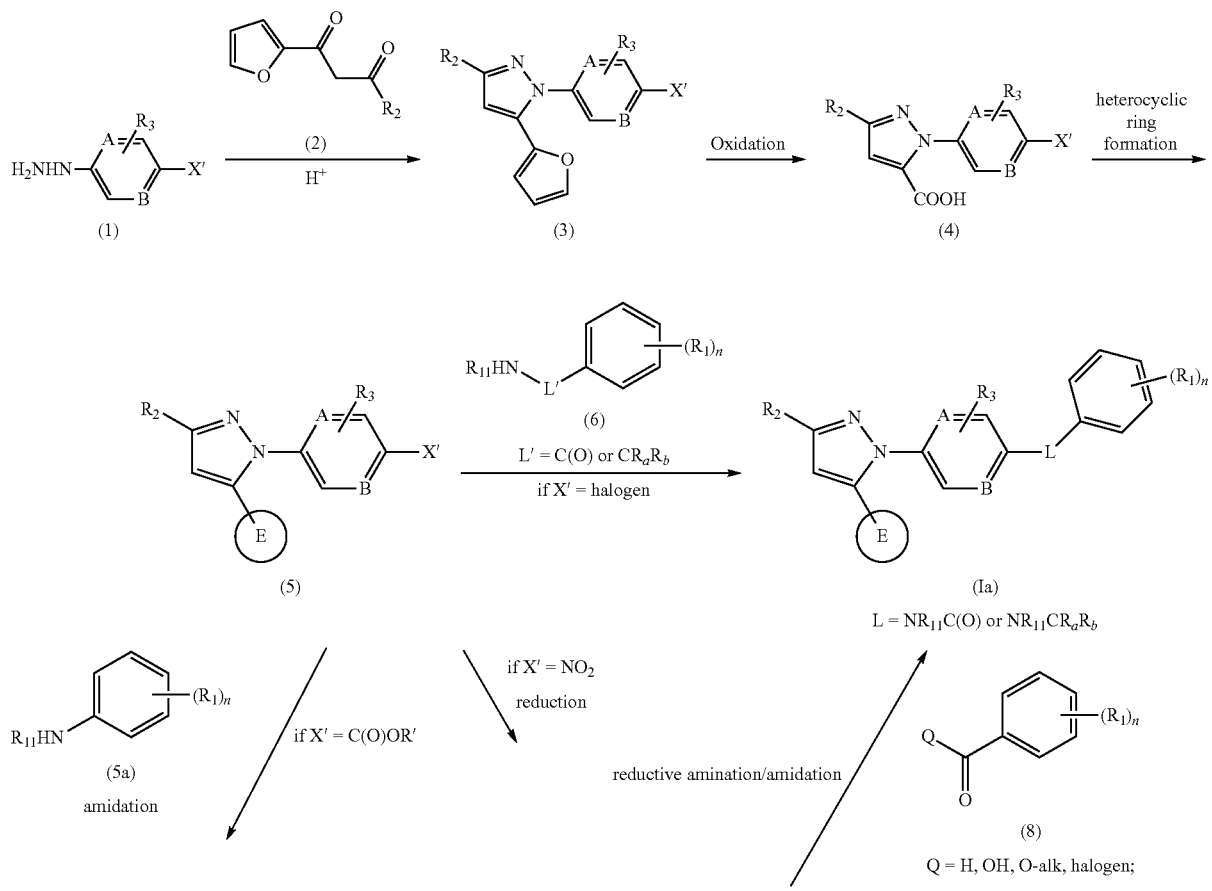

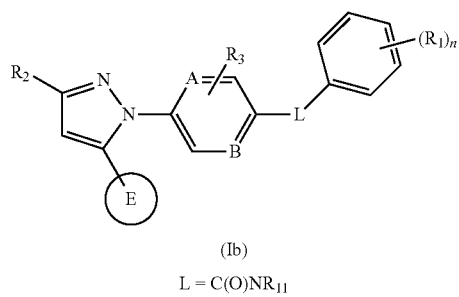

(Ib)

L = C(O)NR$_{11}$

X' = halogen, NO$_2$, COOR'
R' is H or alkyl etc.,;

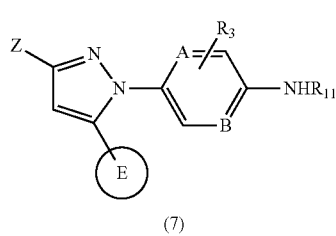

(7)

As depicted in synthetic Scheme-1, the synthesis of compounds of the Formula (5), that served as precursor(s) of the compounds of the invention (Ia) wherein A, B, R$_1$, R$_2$, R$_3$, ring E and 'n' are as defined herein above, began with cyclocondensation of hydrazine derivative(s) of the Formula (1) with appropriately substituted 2,4-diones of the Formula (2) to provide the pyrazole compounds of the Formula (3). Condensations of this type typically afford compounds of the Formula (3) in a regioselective manner as known in the art by using an acid catalyst such as p-toluenesulfonic acid, hydrochloric acid, sulfuric acid etc., and in suitable solvent. Compounds of the Formula (3) undergoes oxidation reaction with suitable oxidants such as potassium permanganate, ozone, sodium metaperiodate, ruthenium chloride and the like; afforded compounds of the Formula (4). This compound of the Formula (4) is further transformed to compounds of the Formula (5) by following the procedure known in the art.

Compounds of the Formula (Ia) prepared by coupling of halogen derivatives of the Formula (5) with amide/amine derivatives of the Formula (6) in presence of suitable reagent and solvent.

Alternatively, nitro derivatives of the Formula (5) where X' is nitro group; are transformed to amine derivatives of the Formula (7) with hydrogen gas in the presence of metal catalysts known in the art such as palladium on carbon, palladium hydroxide and the like; Finally, compound of the Formula (7) is coupled with compound of Formula (8) by reductive amination as per the methods known in the art to obtain amino compound of Formula (Ia) where L is NR$_{11}$CR$_a$R$_b$. Compound of Formula (7) can also converted to compound of Formula (Ia) where L is an amide linker, by following suitable amide coupling reaction with compound of Formula (8).

Alternatively, carboxylate derivatives of the Formula (5) is coupled with amino compound of Formula (5a) to give compounds of the Formula (Ib) where L is C(O)NR$_{11}$.

Scheme-2

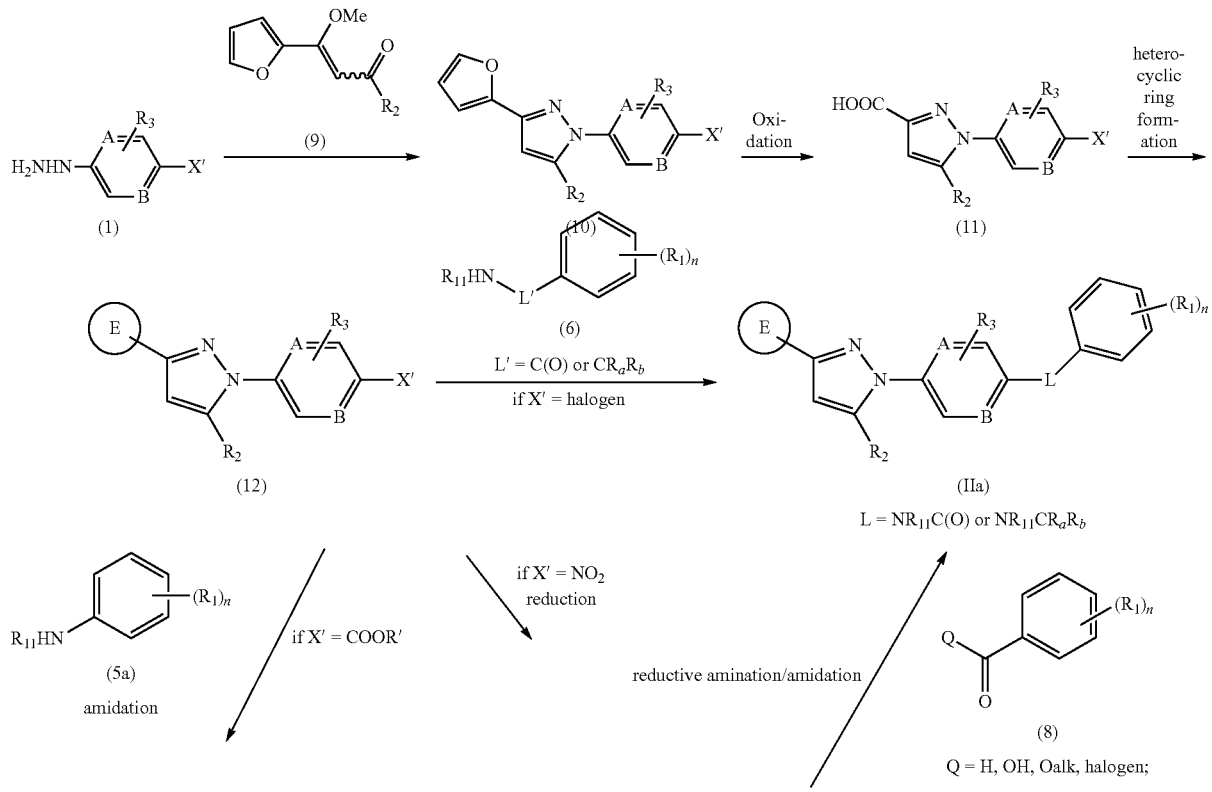

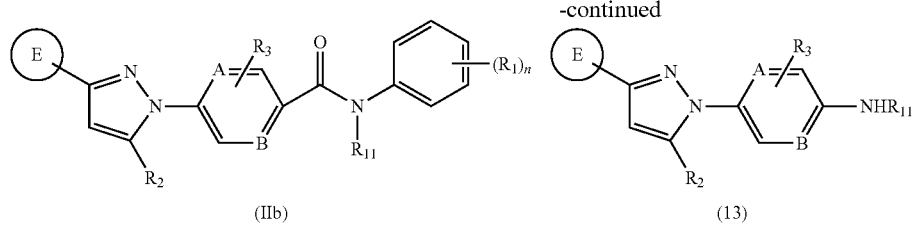

X' = halogen, NO$_2$, COOR';
R' is H, alkyl etc.,;

As described in synthetic Scheme-2, cyclocondensation of hydrazine compound of the Formula (1) with appropriately substituted enol ether(s) of the Formula (9) to provide the pyrazole compound of the Formula (10) regioselectively (*Synthesis*, 2005, 16, 2744). The pyrazole compound of the Formula (10) is converted to acid compound which further converted to compound of Formula (12) by following the methods as described in the synthetic Scheme-1. Finally compound of the Formula (IIa) where L is —NR$_{11}$C(O)— or —NR$_{11}$CR$_a$R$_b$— or Formula (IIb) where L is C(O)NR$_{11}$, obtained from compound of formula (11) by following the suitable reaction step(s) as described in the synthetic Scheme-1.

In another approach as described in the synthetic Scheme 3, the halogen compound of Formula (10) undergoes carboxylation to give acid or ester compound of the Formula (14). Alternatively, compound of the Formula (10) is reacted with metal cyanides such as zinc cyanide, copper cyanide, sodium cyanide, potassium ferrocyanide or mixture(s) thereof; in presence of metal catalysts like Pd$_2$(dba)$_3$, Pd(PPh$_3$)$_4$; in presence of ligands such as bis(diphenylphosphino)ferrocene, dibenzylideneacetone, xantphos or mixture(s) thereof. The said transformation may also be carried out by other methods known in the art. Compounds of the Formula (15) are converted to the compounds of the Formula (16) and in turn to the compounds of the invention of the Formula (IIb) wherein A, B, R$_1$, R$_2$, R$_3$, ring E and 'n' are as defined herein above, by following the methods known in the art or as described in synthetic Scheme 1.

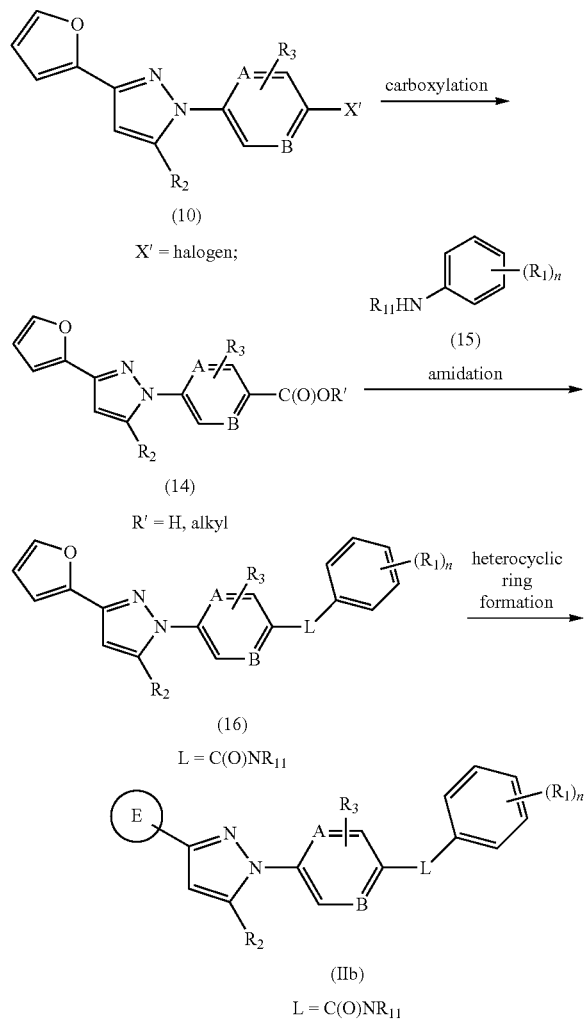

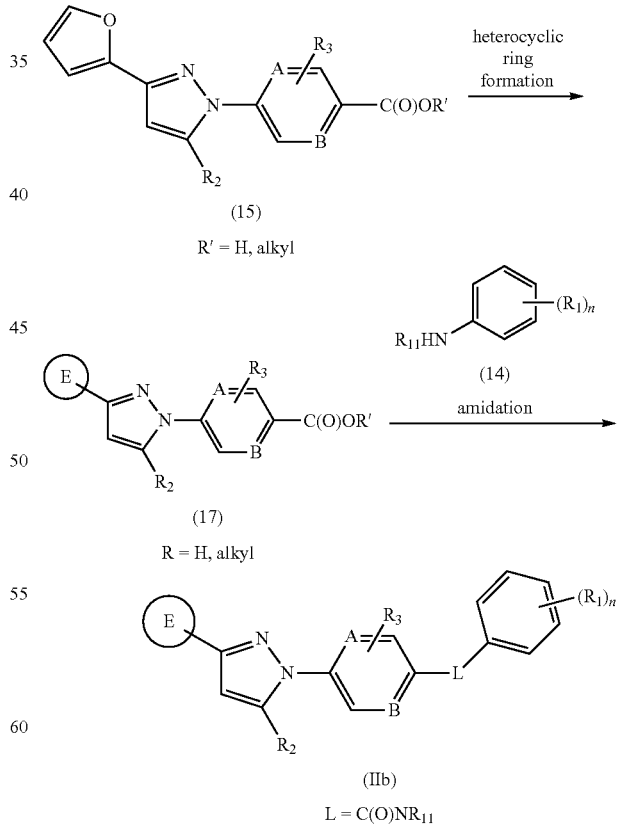

Alternatively, as depicted in synthetic Scheme 4, compound of the Formula (15) is converted to compound of the Formula (17) by following the methods known in the art. Compound of the Formula (17) is transformed to compound of the invention of the Formula (IIb) wherein A, B, R$_1$, R$_2$, R$_3$, ring E and 'n' are as defined herein above, by reacting with compounds of the Formula (14) by amidation by following the methods described in the synthetic Scheme 1 or as known in the art.

Experimental

The invention is further illustrated by the following examples which are provided merely to be exemplary of the invention and do not limit the scope of the invention. The examples set forth below demonstrate the synthetic procedures for the preparation of the representative compounds. Certain modifications and equivalents will be apparent to those skilled in the art and are intended to be included within the scope of the invention. The aforementioned patents and patent applications are incorporated herein by reference.

Unless otherwise stated, work-up implies the following operations: distribution of the reaction mixture between the organic and aqueous phase, separation of layers, drying the organic layer over sodium sulfate, filtration and evaporation of the organic solvent. Purification, unless otherwise mentioned, implies purification by silica gel chromatographic techniques, generally using ethyl acetate/petroleum ether mixture of a suitable polarity as the mobile phase.

Intermediates

Intermediate-1: 5-(1-(5-Bromopyridin-2-yl)-3-(trifluoromethyl)-1H-pyrazol-5-yl)-3-methyl-1,3,4-oxadiazol-2(3H)-one

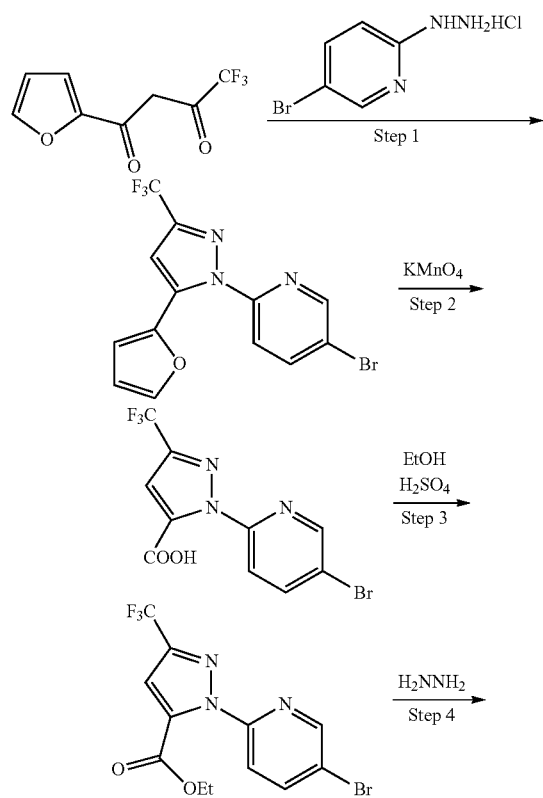

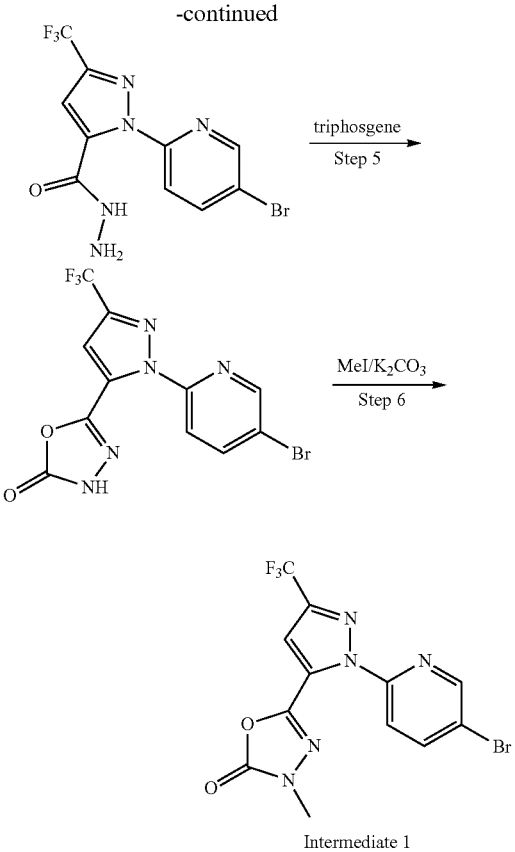

Intermediate 1

Step-1: 5-Bromo-2-(5-(furan-2-yl)-3-(trifluoromethyl)-1H-pyrazol-1-yl)pyridine: A mixture of 4,4,4-trifluoro-1-(furan-2-yl)butane-1,3-dione (7.0 g, 34.0 mmol) and 5-bromo-2-hydrazinylpyridine hydrochloride (7.62 g, 34.0 mmol) in acetic acid (20 mL) was stirred at 70° C. for 1.5 h. The reaction mixture was cooled to room temperature (RT) and then diluted with ethyl acetate (200 mL) and basified with aqueous sodium hydroxide solution (10%, pH 7-8). The resulting slurry was filtered and the filtrate was washed with water (50 mL), dried (Na$_2$SO$_4$) and filtered. The filtrate was rotary evaporated and the crude product was purified by flash column chromatography (silica gel, 20% ethyl acetate-hexanes as eluent) to afford 10 g (82%) of the title compound as white semisolid. $^1$HNMR (400 MHz, CDCl$_3$) δ 8.54 (brs, 1H), 8.02 (dd, J=2.5 & 8.5 Hz, 1H), 7.64 (d, J=8.5 Hz, 1H), 7.45 (d, J=1.5 Hz, 1H), 6.93 (s, 1H), 6.62 (d, J=3.5 Hz, 1H), 6.47 (dd, J=3.5 & 1.5 Hz, 1H); ESI-MS (m/z) 358, 360 [(MH)$^+$, Br$^{79,81}$].

Step-2: 1-(5-Bromopyridin-2-yl)-3-(trifluoromethyl)-1H-pyrazole-5-carboxylic acid: To a stirred solution of step-1 intermediate (10 g, 27.9 mmol) in acetone: water (1:1, 200 mL) at 0° C. was drop-wise added a solution of KMnO4 (30.9 g, 195 mmol) in water (50 mL). The resulting mixture was stirred at room temperature for 15 min and then at 60° C. for 4 h. The reaction was cooled back down to room temperature and 2-propanol (40 mL) was added to the above mixture and stirring was continued for another 4 h at room temperature. The reaction was filtered through celite and the filtrate was evaporated under reduced pressure to dryness. The residue was dissolved in 1N aqueous sodium hydroxide solution (300 mL) and washed with ethyl acetate-hexanes (10%). The aqueous layer was acidified with aqueous hydrochloric acid (10%, pH 4.0) and then extracted with ethyl acetate (3×100 mL). The combined organic layers were washed with brine (100 mL), dried (Na$_2$SO$_4$) and filtered. The filtrate was concentrated under vacuum to afford 6.0 g (64%) of the title compound as a white semi solid. ESI-MS (m/z) 336, 338 [(MH)$^+$, Br$^{79,81}$].

Step-3: Ethyl 1-(5-bromopyridin-2-yl)-3-(trifluoromethyl)-1H-pyrazole-5-carboxylate: To a stirred solution of step-2 intermediate (6.90 g, 20.53 mmol) in ethanol (100 mL) at room temperature was added sulfuric acid (6 mL) dropwise and the reaction was stirred at 100° C. for 18 h. The reaction was cooled to room temperature and the solvent was evaporated under vacuum. Water (100 mL) was added to the above obtained residue, basified with aqueous sodium carbonate solution (10%, 30 mL) and extracted with ethyl acetate (3×100 mL). The combined organic layers were washed with water (100 mL), brine (100 mL), dried (Na$_2$SO$_4$) and filtered. The filtrate was concentrated under vacuum to afford 6.0 g (80%) of the title compound as a white semi-solid. $^1$HNMR (400 MHz, DMSO-d$_6$) δ 8.72 (d, J=2.5 Hz, 1H), 8.38 (dd, J=2.5 & 8.5 Hz, 1H), 7.83 (d, J=8.5 Hz, 1H), 7.62 (s, 1H), 4.25 (q, J=7.0 Hz, 2H), 1.16 (t, J=7.0 Hz, 3H); ESI-MS (m/z) 364, 366 [(MH)$^+$, Br$^{79,81}$].

Step-4: 1-(5-Bromopyridin-2-yl)-3-(trifluoromethyl)-1H-pyrazole-5-carbohydrazide: A mixture of step-3 intermediate (6.0 g, 16.48 mmol) and hydrazine hydrate (2.59 mL, 82 mmol) in ethanol (100 mL) was stirred at 100° C. overnight. Reaction mixture was cooled down to room temperature and the solvent was evaporated under vacuum. The residue was triturated with toluene to obtain 4.0 g (70%) of title compound as a white solid. $^1$HNMR (400 MHz, DMSO-d$_6$) δ 9.99 (s, 1H, D$_2$O exchangeable), 8.64 (d, J=2.5 Hz, 1H), 8.30 (dd, J=2.5 & 8.5 Hz, 1H), 7.75 (d, J=8.5 Hz, 1H), 7.30 (s, 1H), 4.55 (brs, 2H, D$_2$O exchangeable); ESI-MS (m/z) 350, 352 [(MH)$^+$, Br$^{79,81}$].

Step-5: 5-(1-(5-Bromopyridin-2-yl)-3-(trifluoromethyl)-1H-pyrazol-5-yl)-1,3,4-oxadiazol-2(3H)-one: To a stirred and (0° C.) cooled solution of step-4 intermediate (4.0 g, 11.43 mmol) and DIPEA (3.99 mL, 22.85 mmol) in DCM (50 mL) was added a solution of triphosgene (1.35 g, 4.57 mmol) in DCM (20 mL) over a period of 10 min. Reaction mixture was warmed to room temperature and stirred overnight. The reaction was cooled to 0° C. and quenched with ice water (5 mL). Water (25 mL) was added to the above mixture followed by DCM (100 mL). The layers were separated and the aqueous layer was extracted with DCM (2×100 mL). The combined organic layers were washed with brine (50 mL), dried (Na$_2$SO$_4$) and filtered. The filtrate was rotary evaporated to afford 3.0 g (70%) of the title compound as pink semisolid. $^1$HNMR (400 MHz, DMSO-d$_6$) δ 12.95 (s, 1H, D$_2$O exchangeable), 8.71 (d, J=2.5 Hz, 1H), 8.39 (dd, J=2.5 & 8.5 Hz, 1H), 7.90 (d, T=8.5 Hz, 1H), 7.70 (s, 1H); ESI-MS (m/z) 376, 378 [(MH)$^+$, Br$^{79,81}$].

Step-6: 5-(1-(5-Bromopyridin-2-yl)-3-(trifluoromethyl)-1H-pyrazol-5-yl)-3-methyl-1,3,4-oxadiazol-2(3H)-one: To a (0° C.) cooled and stirred solution of step-5 intermediate (3.0 g, 7.98 mmol) in DMF (25 mL) was added potassium carbonate (1.0 g, 7.18 mmol) and methyl iodide (0.50 mL, 7.98 mmol) and the reaction was stirred at room temperature for 18 h. Ice cooled water (10 mL) was then added to the above reaction mixture and the separated solid was filtered and dried to afford 2.50 g (80%) of the desired product as a white solid. $^1$HNMR (400 MHz, CDCl$_3$) δ 8.47 (d, J =2.0 Hz, 1H), 8.05 (dd, J=2.0 & 8.5 Hz, 1H), 7.83 (d, J=8.5 Hz, 1H), 7.12 (s, 1H), 3.51 (s, 3H); ESI-MS (m/z) 390, 392 [(MH)$^+$, Br$^{79,81}$].

Intermediate-2: 5-(1-(5-Bromopyridin-2-yl)-5-(trifluoromethyl)-1H-pyrazol-3-yl)-3-methyl-1,3,4-oxadiazol-2(3H)-one

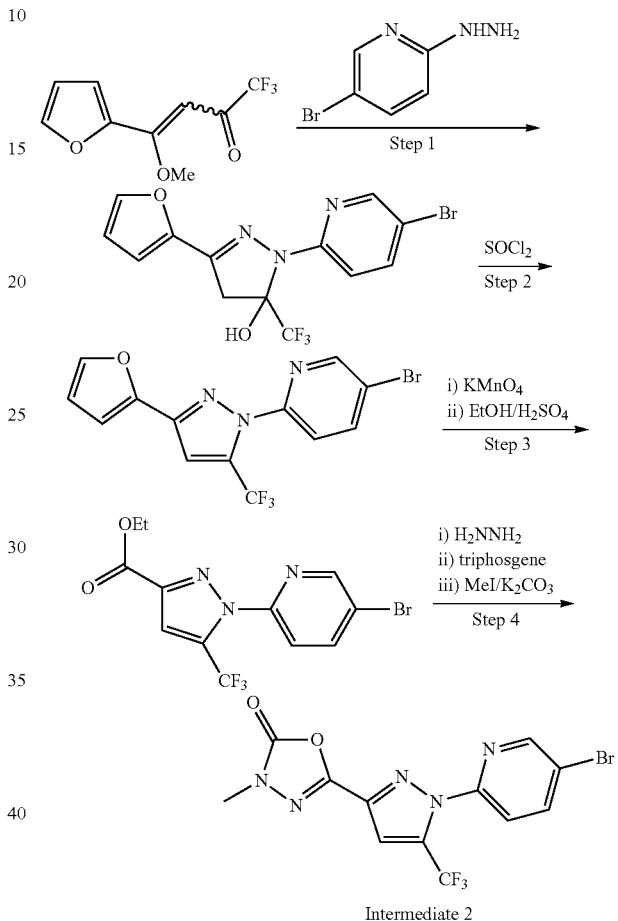

Intermediate 2

Step-1: 1-(5-Bromopyridin-2-yl)-3-(furan-2-yl)-5-(trifluoromethyl)-4,5-dihydro-1H-pyrazol-5-ol: To a stirred solution of 1,1,1-trifluoro-4-(furan-2-yl)-4-methoxybut-3-en-2-one (129 g, 585 mmol; prepared by following the procedure described in Tett Lett., 2002, 43, 8701) in chloroform (600 mL) was added solid 5-bromo-2-hydrazinylpyridine (prepared by the reaction of 2,5-dibromopyridine with hydrazine hydrate, 110.0 g, 585 mmol) in 10 portions at 0° C. over a period of 30 min. The reaction was stirred for 1 h at room temperature, and then at 50° C. for 36 h. The reaction was cooled to 0° C. before the addition of water (200 mL) and chloroform (500 mL). The layers were separated and the aqueous layer was extracted with chloroform (3×200 mL). The combined organic layers were washed with brine (200 mL), dried (Na$_2$SO$_4$) and filtered. The filtrate was rotary evaporated and the crude product was purified by flash column chromatography (5% ethyl acetate-hexanes system as eluent) to afford 90 g (40%) of the title compound as a white solid. $^1$HNMR (400 MHz, CDCl$_3$) δ 8.17 (d, J=2.5 Hz, 1H), 7.96 (s, 1H, D$_2$O Exchangeable), 7.75 (dd, J=2.5 & 8.5 Hz, 1H), 7.56 (d, J=1.5 Hz, 1H), 7.41 (d, J=8.5 Hz, 1H), 6.76 (d, J=2.5 Hz, 1H), 6.54 (dd, J=1.5 & 2.5 Hz, 1H), 3.71(d, J=18.5 Hz, 1H), 3.56 (d, J=18.5 Hz, 1H); ESI-MS (m/z) 376, 378 [(MH)+, Br[79,81]].

Step-2: 5-Bromo-2-(3-(furan-2-yl)-5-(trifluoromethyl)-1H-pyrazol-1-yl) pyridine: To a (5° C.) cooled solution of step-1 intermediate (80 g, 213 mmol) in benzene (600 mL) was added SOCl$_2$ (38.8 mL, 532 mmol). After stirring for 15 min at 5° C., pyridine (51.6 mL, 638 mmol) was added at the same temperature and the reaction was continued to stir for another 15 min. Ice cooled water (100 mL) was then added to the above reaction mixture followed by ethyl acetate (300 mL). The layers were separated and the aqueous layer was extracted with ethyl acetate (2×200 mL). The combined organic layers were washed with saturated aqueous NaHCO$_3$ (300 mL), brine (200 mL), dried (Na$_2$SO$_4$) and filtered. The filtrate was concentrated under vacuum to afford 70 g (92%) of the title compound as white solid. $^1$HNMR (400 MHz, CDCl$_3$) δ 8.55 (d, J=1.5 Hz, 1H), 7.97 (dd, J=2.0 & 8.5 Hz, 1H), 7.84 (d, J=8.5 Hz, 1H), 7.53 (d, J=1.5 Hz, 1H), 7.11 (s, 1H), 6.84 (d, J=3.0 Hz, 1H), 6.53 (dd, J=3.0 & 1.5 Hz, 1H); ESI-MS (m/z) 358, 360 [(MH)+, Br[79,81]].

Step-3: Ethyl-1-(5-bromopyridin-2-yl)-5-(trifluoromethyl)-1H-pyrazole-3-carboxylate: The title compound was prepared by following the similar procedure described for step-3 of Intermediate-1 using above step-2 intermediate. $^1$HNMR (400 MHz, CDCl$_3$) δ 8.59 (d, J=2.5 Hz, 1H), 8.03 (dd, J=2.5 & 8.5 Hz, 1H), 7.87 (d, J=8.5 Hz, 1H), 7.37 (s, 1H), 4.46 (q, J=7.0 Hz, 2H), 1.43 (t, J=7.0 Hz, 3H); ESI-MS (m/z) 364, 366 [(MH)+, BR[79,81]].

Step-4: 5-(1-(5-Bromopyridin-2-yl)-5-(trifluoromethyl)-1H-pyrazol-3-yl)-3-methyl-1,3,4-oxadiazol-2(3H)-one: The title compound was prepared by following the similar procedure sequentially as described in Step-4, Step-5, and Step-6 of Intermediate-1 using above step-3 intermediate. $^1$HNMR (400 MHz, DMSO-d$_6$) δ 8.75 (d, J=2.5 Hz, 1H), 8.38 (dd, J=2.5 & 8.5 Hz, 1H), 7.88 (d, J=8.5 Hz, 1H), 7.75 (s, 1H), 3.43 (s, 3H); ESI-MS (m/z) 390, 392 [(MH)+, Br[79,81]].

Intermediate-3: 6-(3-(4-Methyl-5-oxo-4,5-dihydro-1,3,4-oxadiazol-2-yl)-5-(trifluoromethyl)-1H-pyrazol-1-yl)nicotinic acid

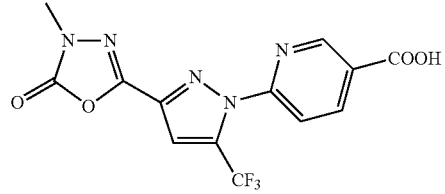

intermediate 3

Step-1: 6-(3-(4-Methyl-5-oxo-4,5-dihydro-1,3,4-oxadiazol-2-yl)-5-(trifluoromethyl)-1H-pyrazol-1-yl)nicotinonitrile: In a sealed tube containing a suspension of Intermediate-2 (1.0 g, 2.56 mmol), dicyanozinc (0.90 g, 7.69 mmol) in dioxane (8 mL) was purged nitrogen gas for 30 min and, tetrakis(triphenylphosphine)palladium(O) (296 mg, 0.256 mmol) was added. The resulting mixture was thoroughly deoxygenated by purging nitrogen gas and the sealed tube was capped and stirred at 110° C. for 5 h. The reaction mixture was cooled back down to room temperature and ammonium hydroxide solution (1.0 mL) was added followed by water (10 mL) and then diluted with ethyl acetate (50 mL). The layers were separated and the aqueous layer was extracted with ethyl acetate (2×30 mL). The combined organic layers were washed with saturated aqueous NaHCO$_3$ (50 mL), dried (Na$_2$SO$_4$) and filtered. The filtrate was rotary evaporated and the crude product was purified by flash column chromatography (20% ethyl acetate-hexanes as eluent) to afford 850 mg (99%) of the title compound as white solid. $^1$HNMR (400 MHz, DMSO-d$_6$) δ 9.10 (d, J=2.5 Hz, 1H), 8.62 (dd, J=2.5 & 8.5 Hz, 1H), 8.13 (d, J=8.5 Hz, 1H), 7.83 (s, 1H), 3.44 (s, 3H);ESI-MS (m/z) 337 (MH)+.

Step-2: 5-6-(3-(4-Methyl-5-oxo-4,5-dihydro-1,3,4-oxadiazol-2-yl)-5-(trifluoromethyl)-1H-pyrazol-1-yl)nicotinic acid: In a sealed tube containing a solution of 6-(3-(4-methyl-5-oxo-4,5-dihydro-1,3,4-oxadiazol-2-yl)-5-(trifluoromethyl)-1H-pyrazol-1-yl)nicotinonitrile (0.80 g, 2.37 mmol) in methanesulfonic acid (5 mL, 77 mmol) and water (4 mL) was heated at 70° C. for 6 h. The reaction mixture was then cooled to room temperature and water (10 mL) was added to the above mixture followed by ethyl acetate (50 mL). The layers were separated and the aqueous layer was extracted with ethyl acetate (2×30 mL). The combined organic layers were washed with saturated aqueous NaHCO$_3$ (30 mL), dried (Na$_2$SO$_4$) and filtered. The filtrate was rotary evaporated to afford 500 mg (60%) of the title compound as white solid. $^1$HNMR (400 MHz, DMSO-d$_6$) δ 13.71 (s, 1H, D$_2$O exchangeable), 9.01 (d, J=2.5 Hz, 1H), 8.55 (dd, J=2.5 & 8.5 Hz, 1H), 8.06 (d, J=8.5 Hz, 1H), 7.80 (s, 1H), 3.40 (s, 3H); ESI-MS (m/z) 356 (MH)+.

Intermediate-4: 3-(1-(5-Bromopyridin-2-yl)-5-(trifluoromethyl)-1H-pyrazol-3-yl)-5,5-dimethylisoxazol-4(5H)-one

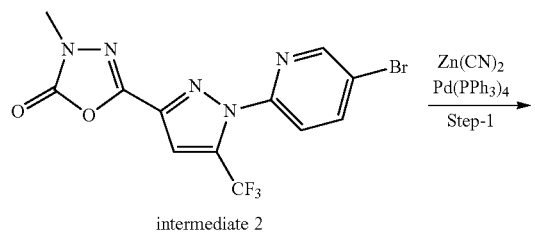

intermediate 2

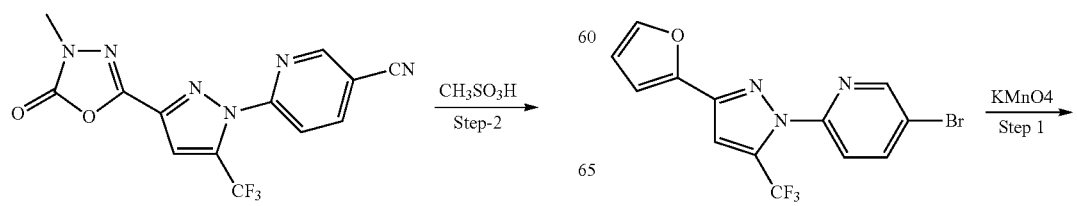

-continued

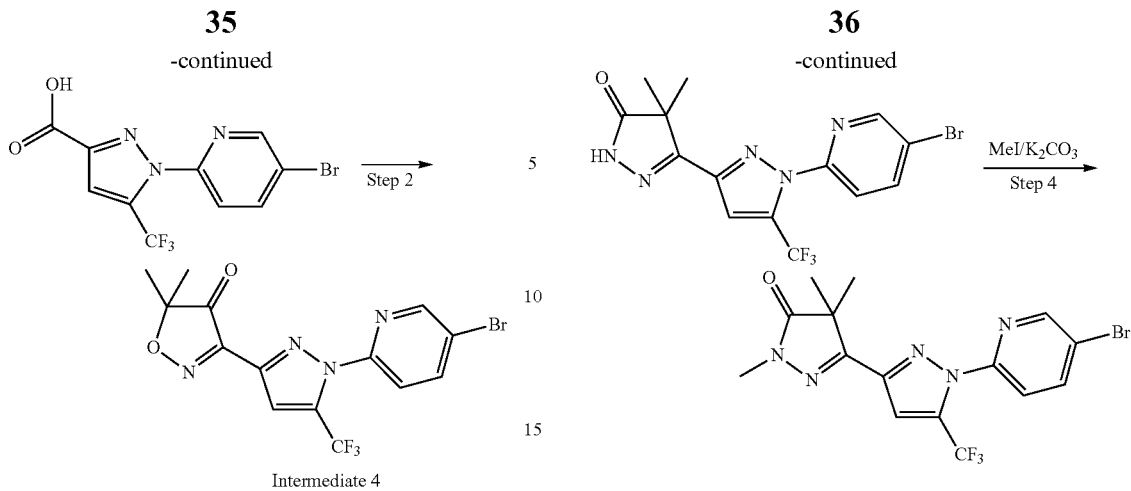

Intermediate 4

Step-1: 1-(5-Bromopyridin-2-yl)-5-(trifluoromethyl)-1H-pyrazole-3-carboxylic acid: The title compound was prepared from Step-2 of Intermediate-2 using potassium permanganate by following the similar procedure as described in Step-2 of Intermediate-1. $^1$HNMR (400 MHz, DMSO- $d_6$) δ 8.73 (d, J=2.5 Hz, 1H), 8.36 (dd, J=2.5 & 8.5 Hz, 1H), 7.88 (d, J=8.5 Hz, 1H), 7.51 (s, 1H); ESI-MS (m/z) 336, 338 [(M)$^+$, Br$^{79,81}$].

Step-2: 3-(1-(5-Bromopyridin-2-yl)-5-(trifluoromethyl)-1H-pyrazol-3-yl)-5,5-dimethyl isoxazol-4(5H)-one: The title compound was prepared from 1-(5-bromopyridin-2-yl)-5-(trifluoromethyl)-1H-pyrazole-3-carboxylic acid by following the analogues procedure as described in WO2012056748. $^1$HNMR (400 MHz, CDCl$_3$) δ 8.60 (d, J=2.5 Hz, 1H), 8.02 (dd, J=2.5 & 8.5 Hz, 1H), 7.92 (d, J=8.5 Hz, 1H), 7.52 (s, 1H), 1.53 (s, 6H); ESI-MS (m/z) 403, 405 [(MH)$^+$, Br$^{79,81}$].

Intermediate-5: 1'-(5-Bromopyridin-2-yl)-1,4,4-trimethyl-5'-(trifluoromethyl)-1H,1'H-[3,3'-bipyrazol]-5(4H)-one

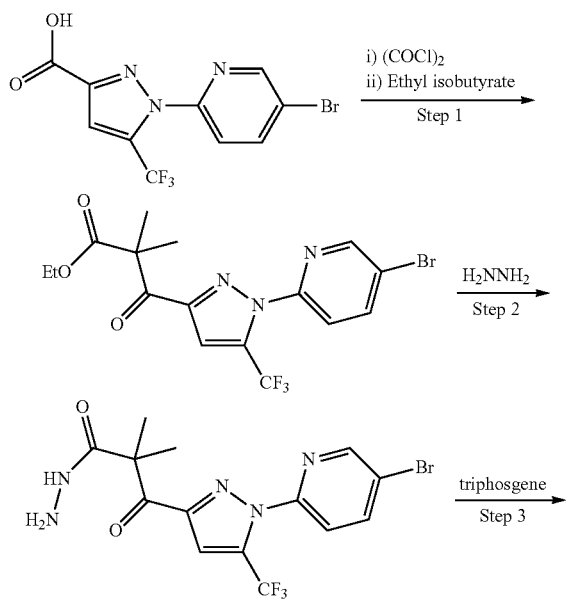

Step-1: Ethyl 3-(1-(5-bromopyridin-2-yl)-5-(trifluoromethyl)-1H-pyrazol-3-yl)-2,2-dimethyl-3-oxopropanoate: To (0° C.) cooled and stirred solution of 1-(5-bromopyridin-2-yl)-5-(trifluoromethyl)-1H-pyrazole-3-carboxylic acid (6.0 g, 17.85 mmol) in DCM (30 mL) was added oxalyl chloride (4.69 mL, 53 6 mmol) followed by catalytic amount of DMF (0.14 mL, 1.78 mmol). The resulting mixture was warmed to room temperature and then stirred for 1 h. Reaction mass was concentrated under vacuum and the crude product was dried under vacuum.

To a freshly prepared solution of lithium diisopropyl amide (prepared by the addition of n-butyl lithium (12.27 mL, 19.63 mmol) to a solution of diisopropylamine (2.80 mL, 19.63 mmol) in THF (20 mL)) at −78° C., was drop-wise added a solution of ethyl isobutyrate (2.21 mL, 16.36 mmol) in THF (10 mL). The resulting mixture was stirred at the same temperature for 1 h and then the above prepared solution of 1-(5-bromopyridin-2-yl)-5-(trifluoromethyl)-1H-pyrazole-3-carbonyl chloride (5.80 g, 16.36 mmol) in THF (20 mL) was drop-wise added. The resulting mixture was stirred at −78° C. for 30 min, then gradually warmed to room temperature over 1 h and then stirred for another 1 h at room temperature. The reaction was cooled to 0° C. and then quenched with saturated ammonium chloride solution (20 mL) and then diluted with ethyl acetate (100 mL). The layers were separated and the aqueous layer was extracted with ethyl acetate (2×50 mL). The combined organic layers were washed with brine (50 mL), dried (Na$_2$SO$_4$) and filtered. The filtrate was rotary evaporated and the crude product was purified by flash column chromatography (10% ethyl acetate in hexanes as eluent) to afford 2.50 g (35%) of the title compound as a white solid. $^1$HNMR (400 MHz, CDCl$_3$) δ 8.58 (d, J=2.0 Hz, 1H), 8.02 (dd, J=2.0 & 8.0 Hz, 1H), 7.73 (d, J=8.0 Hz, 1H), 7.39 (s, 1H), 4.11 (q, J=7.0 Hz, 2H), 1.60 (s, 3H), 1.58 (s, 3H), 1.04 (t, J=7.0 Hz, 3H); ESI-MS (m/z) 434, 436 [(MH)$^+$Br79,81].

Step-2: 3-(1-(5-Bromopyridin-2-yl)-5-(trifluoromethyl)-1H-pyrazol-3-yl)-2,2-dimethyl-3-oxopropanehydrazide: A mixture of step-1 intermediate (2.40 g, 5.53 mmol) and hydrazine hydrate (0.87 mL, 27.6 mmol) in ethanol (30 mL) was heated at 80° C. overnight. The reaction mixture was cooled to room temperature and the solvent was then evaporated under vacuum. The residue was triturated with toluene to obtain 2.0 g (86%) of title compound as a white solid. $^1$HNMR (400 MHz, DMSO-$d_6$) δ 11.78 (s, 1H, D$_2$O exchangeable), 8.72 (d, J=2.0 Hz, 1H), 8.38 (dd, J=2.0 & 8.0 Hz, 1H), 7.92 (d, J=8.0 Hz, 1H), 7.54 (s, 1H), 1.42 (s, 6H); ESI-MS (m/z) 420, 422 [(MH)$^+$, Br$^{79,81}$].

Step-3: 1'-(5-Bromopyridin-2-yl)-4,4-dimethyl-5'-(trifluoromethyl)-1H, 1'H-[3,3'-bipyrazol]-5(4H)-one: To a stirred and (0° C.) cooled solution of step-2 intermediate (2.0 g, 4.76 mmol) and DIPEA (1.66 mL, 9.52 mmol) in DCM (20 mL) was added a solution of triphosgene (560 mg, 1.90 mmol) in DCM (5 mL) over a period of 10 min. The reaction mixture was warmed to room temperature and then stirred overnight. Reaction was cooled down to 0° C. and then quenched with ice water (5 mL). Water (25 mL) was added to the reaction followed by DCM (50 mL). The layers were separated and the aqueous layer was extracted with DCM (2×50 mL). The combined organic layers were washed with brine (50 mL), dried ($Na_2SO_4$) and filtered. The filtrate was rotary evaporated to afford 1.50 g (78%) of the title compound as semisolid. $^1$HNMR (400 MHz, $CDCl_3$) δ 8.85 (s, 1H, $D_2O$ exchangeable), 8.59 (d, J=2.0 Hz, 1H), 8.02 (dd, J=2.0 & 8.0 Hz, 1H), 7.78 (d, J=8.0 Hz, 1H), 7.31 (s, 1H), 1.60 (s, 6H); ESI-MS (m/z) 402, 404 [(MH)$^+$, Br$^{79,81}$].

Step-4: 1'-(5-Bromopyridin-2-yl)-1,4,4-trimethyl-5'-(trifluoromethyl)-1H,1'H-[3,3'-bipyrazol]-5(4H)-one: To a (0° C.) cooled and stirred solution of step-3 intermediate (1.50 g, 3.73 mmol) in DMF (10 mL) was added potassium carbonate (619 mg, 4.48 mmol) and methyl iodide (0.28 mL, 4.48 mmol) and the reaction was stirred at room temperature for 18 h. Ice cooled water (10 mL) was added to the above reaction mixture and the separated solid was filtered and dried to afford 1.50 g (97%) of the desired product as a white solid. $^1$HNMR (400 MHz, $CDCl_3$) δ 8.59 (d, J=2.0 Hz, 1H), 8.03 (dd, J=2.0 & 8.0 Hz, 1H), 7.78 (d, J=8.0 Hz, 1H), 7.32 (s, 1H), 3.44 (s, 3H), 1.55 (s, 6H); ESI-MS (m/z) 416, 418 [(MH)$^+$, Br$^{79,81}$].

Intermediate-6: 3-(1-(5-Bromopyridin-2-yl)-5-(trifluoromethyl)-1H-pyrazol-3-yl)-4-methyl-1,2,4-oxadiazol-5(4H)-one

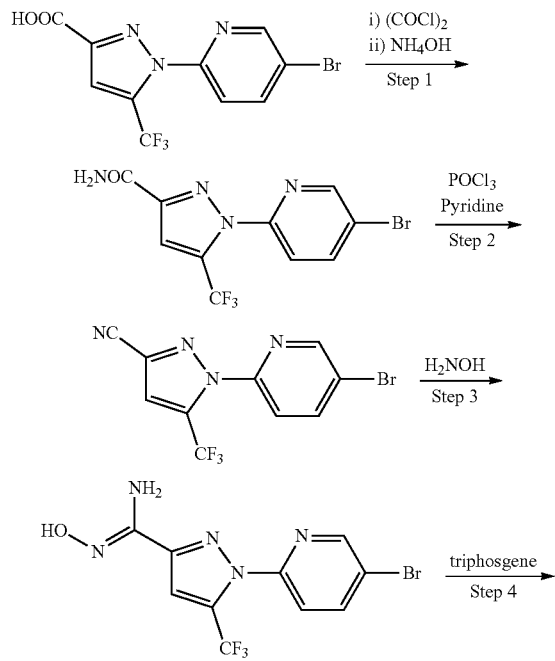

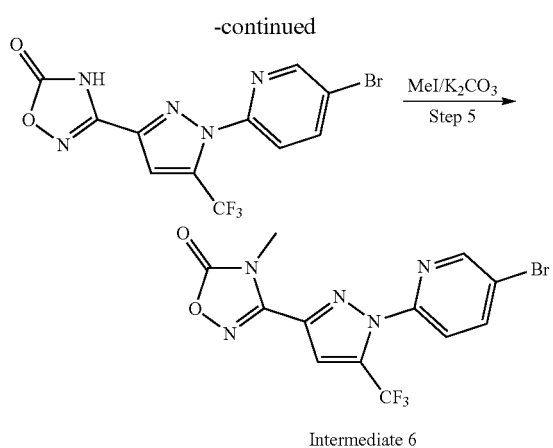

Intermediate 6

Step-1: 1-(5-Bromopyridin-2-yl)-5-(trifluoromethyl)-1H-pyrazole-3-carboxamide: To a (0° C.) cooled solution of 1-(5-bromopyridin-2-yl)-5-(trifluoromethyl)-1H-pyrazole-3-carboxylic acid (5.0 g, 14.88 mmol) in DCM (50 mL) was added oxalyl chloride (3.91 mL, 44.6 mmol) followed by catalytic amount of DMF (0.14 mL, 1.78 mmol). The resulting mixture was stirred at room temperature for 1 h. The excess of oxalyl chloride was removed under vacuum and the residue was again diluted with DCM (100 mL). Aqueous ammonium hydroxide solution (29.0 mL, 744 mmol) was added dropwise to the above mixture at 0° C. and the reaction mixture was stirred at room temperature overnight. The solvent was evaporated under vacuum and concentrate was diluted with ethyl acetate (100 mL). The layers were separated and the aqueous layer was extracted with ethyl acetate (2×100 mL). The combined organic layers were washed with brine (100 mL), dried ($Na_2SO_4$) and filtered. The filtrate was rotary evaporated to afford 4.0 g (80%) of the title compound as white solid. $^1$HNMR (400 MHz, DMSO-$d_6$) δ 8.73 (d, J=2.0 Hz, 1H), 8.41 (dd, J=2.0 & 8.0 Hz, 1H), 8.09 (s, 1H, $D_2O$ exchangeable), 7.97 (d, J=8.0 Hz, 1H), 7.70 (s, 1H, $D_2O$ exchangeable), 7.52 (s, 1H); ESI-MS (m/z) 335, 337 [(MH)$^+$, Br$^{79,81}$].

Step-2: 1-(5-Bromopyridin-2-yl)-5-(trifluoromethyl)-1H-pyrazole-3-carbonitrile: To a stirred and (0° C.) cooled solution of step-1 intermediate (4.0 g, 11.94 mmol) in $POCl_3$ (22.25 mL, 239 mmol) was added pyridine (1.93 mL, 23.87 mmol). The resulting mixture was warmed to room temperature and then stirred at 80° C. for 3 h. The reaction was cooled to room temperature and the excess of $POCl_3$ was evaporated under vacuum. Water (50 mL) was added to the above obtained residue, basified with aqueous saturated sodium bicarbonate solution (50 mL) and extracted with ethyl acetate (3×100 mL). The combined organic layers were washed with water (50 mL), brine (50 mL), dried ($Na_2SO_4$) and filtered. The filtrate was concentrated under vacuum to afford 3.20 g (85%) of the title compound as a white solid. $^1$HNMR (400 MHz, $CDCl_3$) δ 8.61 (d, J=2.0 Hz, 1H), 8.08 (dd, J=2.0 & 8.0 Hz, 1H), 7.81 (d, J=8.0 Hz, 1H), 7.26 (s, 1H); ESI-MS (m/z) 317, 319 [(MH)$^+$, Br$^{79,81}$].

Step-3: 1-(5-Bromopyridin-2-yl)-N-hydroxy-5-(trifluoromethyl)-1H-pyrazole-3-carboximidamide: A mixture of step-2 intermediate (150 mg, 0.473 mmol), hydroxylamine hydrochloride (82 mg, 1.183 mmol) and $Na_2CO_3$ (125 mg, 1.183 mmol) in ethanol (10 mL) was stirred at 85° C. for 6 h. Reaction mixture was cooled to room temperature and the solvent was evaporated under vacuum. Water (10 mL) was added to the obtained residue and extracted with ethyl acetate (2×25 mL). The combined organic layers were washed with water (20 mL), brine (20 mL), dried (Na$_2$SO$_4$) and filtered. The filtrate was concentrated under vacuum to afford 106 mg (64%) of the title compound as a white solid. $^1$HNMR (400 MHz, DMSO- d$_6$) δ 9.96 (s, 1H), 8.69 (d, J=2.0 Hz, 1H), 8.37 (dd, J=2.0 & 8.0 Hz, 1H), 8.00 (d, J=8.0 Hz, 1H), 7.23 (s, 1H), 5.93 (s, 2H); ESI-MS (m/z) 350, 352 [(MH)$^+$, Br$^{79,81}$].

Step-4: 3-(1-(5-Bromopyridin-2-yl)-5-(trifluoromethyl)-1H-pyrazol-3-yl)-1,2,4-oxadiazol-5(4H)-one: To a stirred and (0° C.) cooled solution of step-3 intermediate (106 mg, 0.303 mmol) and DIPEA (0.106 mL, 0.606 mmol) in DCM (15 mL) was added drop-wise a solution of triphosgene (35 mg, 0.121 mmol) in DCM (3 mL). The reaction was stirred at room temperature for 1 h before quenching with ice water (5 mL). Water (10 mL) was added to the above mixture followed by DCM (25 mL). The layers were separated and the aqueous layer was extracted with DCM (2×15 mL). The combined organic layers were washed with brine (15 mL), dried (Na$_2$SO$_4$) and filtered. The filtrate was rotary evaporated to afford 100 mg (88%) of the title compound as brown solid. ESI-MS (m/z) 376, 378 [(MH)$^+$, Br$^{79,81}$].

Step-5: 3-(1-(5-Bromopyridin-2-yl)-5-(trifluoromethyl)-1H-pyrazol-3-yl)-4-methyl-1,2,4-oxadiazol-5(4H)-one: To a (0° C.) cooled and stirred solution of step-4 intermediate (100 mg, 0.266 mmol) in DMF (3 mL) was added potassium carbonate (73 mg, 0.532 mmol) and methyl iodide (33 μL, 0.532 mmol) and the reaction was stirred at room temperature for 18 h. Ice cooled water (3 mL) was added to the reaction and extracted with ethyl acetate (2×15 mL). The combined organic layers were washed with water (3×10 mL), brine (10 mL), dried (Na$_2$SO$_4$) and filtered. The filtrate was rotary evaporated and the crude product was purified by flash column chromatography to afford 25 mg (24%) of the title compound as white solid. $^1$HNMR (400 MHz, CDCl$_3$) δ 8.64 (d, J=2.0 Hz, 1H), 8.07 (dd, J=2.0 & 8.0Hz, 1H), 7.73 (d, J=8.0 Hz, 1H), 7.44 (s, 1H), 3.68 (s, 3H); ESI-MS (m/z) 390, 392 [(MH)$^+$, Br$^{79,81}$].

Intermediate-7: 1-(5-(1-(5-Bromopyridin-2-yl)-5-(trifluoromethyl)-1H-pyrazol-3-yl)-2,2-dimethyl-1,3,4-oxadiazol-3(2H)-yl)ethanone

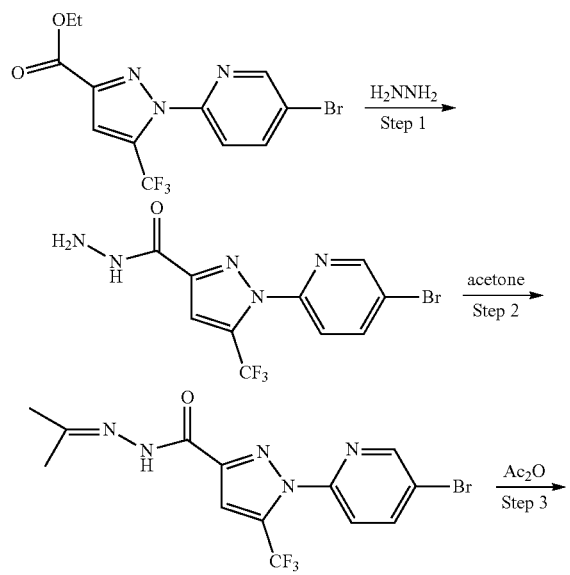

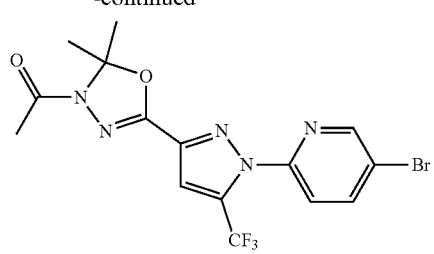

Intermediate 7

Step-1: 1-(5-Bromopyridin-2-yl)-5-(trifluoromethyl)-1H-pyrazole-3-carbohydrazide: A mixture of ethyl 1-(5-bromopyridin-2-yl)-5-(trifluoromethyl)-1H-pyrazole-3-carboxylate (33 g, 91 mmol) and hydrazine hydrate (17.07 mL, 544 mmol) in ethanol (330 mL) was heated at 100° C. overnight. The reaction mixture was cooled back down to room temperature and the solvent was evaporated under vacuum. The residue was triturated with toluene to obtain 30 g (95%) of the title compound as a white solid. $^1$HNMR (400 MHz, DMSO-d$_6$) δ 9.97 (s, 1H, D$_2$O exchangeable), 8.72 (d, J=2.5 Hz, 1H), 8.40 (dd, J=2.5 & 8.5 Hz, 1H), 7.98 (d, J=8.5 Hz, 1H), 7.54 (s, 1H), 4.58 (s, 2H, D$_2$O exchangeable); ESI-MS (m/z) 350, 352 [(MH)$^+$, Br$^{79,81}$].

Step-2: 1-(5-Bromopyridin-2-yl)-N'-(propan-2-ylidene)-5-(trifluoromethyl)-1H-pyrazole-3-carbohydrazide: A solution of step-1 intermediate (1.0 g, 2.86 mmol) in acetone:hexane (1:1, 12 mL) was stirred at 70° C. for 3 h. The reaction was then cooled to room temperature and the solvent was evaporated under vacuum to afford 800 mg (72%) of the title compound as white solid. ESI-MS (m/z) 390, 392 [(MH)$^+$, Br$^{79,81}$].

Step-3: 1-(5-(1-(5-Bromopyridin-2-yl)-5-(trifluoromethyl)-1H-pyrazol-3-yl)-2,2-dimethyl-1,3,4-oxadiazol-3 (2H)-yl)ethanone: A mixture of step-2 intermediate (800 mg, 2.05 mmol) and pyridine (0.33 mL, 4.1 mmol) in acetic anhydride (8 mL) was stirred at 140° C. for 3 h. The reaction was then cooled to room temperature and the solvent was evaporated under vacuum. The crude product was purified by flash column chromatography (silica gel, ethyl acetate-hexanes system as eluent) to afford 250 mg (28%) of the title compound as white solid. $^1$HNMR (400 MHz, DMSO-d$_6$) δ 8.76 (d, J=2.0 Hz, 1H), 8.36 (dd, J=2.0 & 8.0 Hz, 1H), 7.88 (d, J=8.0 Hz, 1H), 7.65 (s, 1H), 2.21 (s, 3H), 1.81 (s, 6H); ESI-MS (m/z) 432, 434[(MH)$^+$, Br$^{79,81}$].

Intermediate-8: 2-(1-(5-Bromopyridin-2-yl)-5-(trifluoromethyl)-1H-pyrazol-3-yl)-4,4-dimethyl-4,5-dihydrooxazole

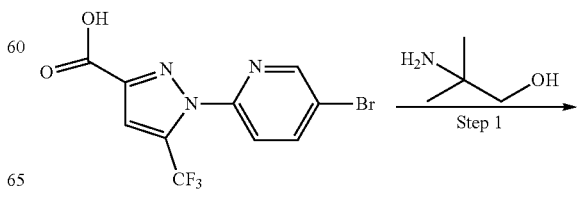

-continued

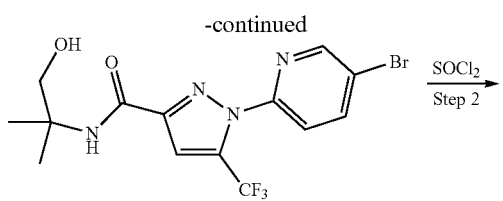

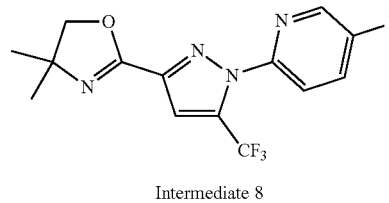

Intermediate 8

Step-1: 1-(5-Bromopyridin-2-yl)-N-(1-hydroxy-2-methylpropan-2-yl)-5-(trifluoromethyl)-1H-pyrazole-3-carboxamide: To (0° C.) cooled solution of 1-(5-bromopyridin-2-yl)-5-(trifluoromethyl)-1H-pyrazole-3-carboxylic acid (500 mg, 1.48 mmol), in DCM (20 mL) was added oxalyl chloride (391 µL, 4.46 mmol) followed by catalytic amount of DMF. The resulting mixture was stirred at room temperature for 3 h. The solvent and excess of oxalyl chloride was then removed under vacuum and the resulting residue was dissloved in DCM (10 mL). A solution of 2-amino-2-methylpropan-1-ol (0.35 mL, 3.72 mmol) in DCM (5 mL) was then added to the above solution drop-wise at 0° C. and the resulting mixture was warmed to room temperature and then continued stirring at the same temperature for 18 h. Water (10 mL) was added to the above reaction followed by DCM (20 mL). The layers were separated and the aqueous layer was extracted with DCM (3×10 mL). The combined organic layers were washed with bine (10 mL), dried (anhydrous $Na_2SO_4$) and filtered. The filtrate was rotary evaporated and the crude product was purified by flash column chromatography to afford 600 mg (99%) of the title compound as white solid. $^1$HNMR (400 MHz, $CDCl_3$) δ 8.61 (d, J=2.0 Hz, 1H), 8.04 (dd, J=2.0 & 8.0 Hz, 1H), 7.75 (d, J=8.0 Hz, 1H), 7.37 (s, 1H), 6.96 (s, 1H, $D_2O$ exchangeable), 3.73 (s, 2H), 1.44 (s, 6H) ; ESI-MS (m/z) 407, 409 [(MH)$^+$, Br$^{79,81}$].

Step-2: 2-(1-(5-Bromopyridin-2-yl)-5-(trifluoromethyl)-1H-pyrazol-3-yl)-4,4-dimethyl-4,5-dihydrooxazole: To a stirred solution of step-1 intermediate (600 mg, 1.47 mmol) in DCM (15 mL) at room temperature was added thionyl chloride (215 µL, 2.95 mmol) drop-wise and the resulting mixture was then stirred at room temperature for 24 h. The reaction was then cooled to 0° C., diluted with water (20 mL) and the layers were separated. The aqueous layer was extracted with DCM (10 mL). The combined organic layers were washed with brine (10 mL), dried ($Na_2SO_4$) and filtered. The filtrate was rotary evaporated and the crude product was purified by flash column chromatography (silica gel, ethyl acetate-hexanes system as eluent) to afford 310 mg (54%) of the title compound as white solid. $^1$HNMR (400 MHz, $CDCl_3$) δ 8.57 (d, J=2.0 Hz, 1H), 8.00 (dd, J=2.0 & 8.0 Hz, 1H), 7.89 (d, J=8.0 Hz, 1H), 7.38 (s, 1H), 4.20 (s, 2H), 1.43 (s, 6H); ESI-MS (m/z) 389, 391 [(MH)$^+$, Br$^{79,81}$]

Intermediate-9: 5-(1-(5-Bromopyridin-2-yl)-3-cyclopropyl-1H-pyrazol-5-yl)-3-methyl-1,3,4-oxadiazol-2(3H)-one

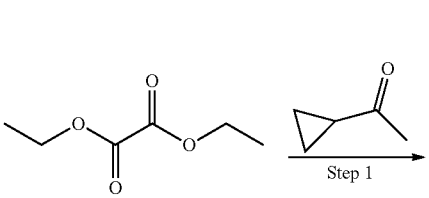

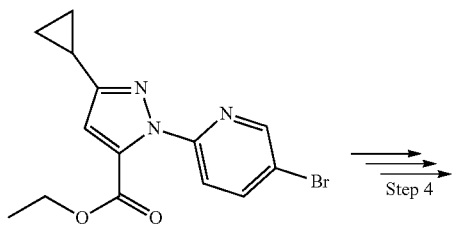

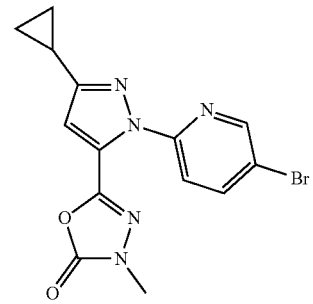

Intermediate 9

Step-1: Ethyl 4-cyclopropyl-2,4-dioxobutanoate: The title compound was prepared by reacting 1-cyclopropylethanone with diethyl oxalate by following the procedure described in US20120115903.

Step-2: Ethyl 4-cyclopropyl-2-(methoxyimino)-4-oxobutanoate: The title compound was prepared by reacting ethyl 4-cyclopropyl-2,4-dioxobutanoate with O-methylhydroxylamine hydrochloride in ethanol-water (5:1) by following the procedure described in WO2012022487.

Step-3: Ethyl 1-(5-Bromopyridin-2-yl)-3-cyclopropyl-1H-pyrazole-5-carboxylate: To a stirred solution of ethyl 4-cyclopropyl-2-(methoxyimino)-4-oxobutanoate (420 mg, 1.97 mmol) in acetic acid:2-methoxyethanol (6 mL, 2:1) was added 5-bromo-2-hydrazinylpyridine (370 mg, 1.97 mmol) at room temperature. The resulting mixture was refluxed for 3 h. The reaction mixture was cooled to room temperature and the solvent was evaporated under vacuum. The crude product was purified by flash column chromatography (silica gel, ethyl acetate-hexanes system) to afford 220 mg (33%) of the title compound as pale yellow syrup. $^1$HNMR (400 MHz, CDCl$_3$) δ 8.49 (d, J=2.0 Hz, 1H), 7.95 (dd, J=2.0 & 8.0 Hz, 1H), 7.58 (d, J=8.0 Hz, 1H), 6.56 (s, 1H), 4.30 (q, J=7.0 Hz, 2H), 2.04-1.98 (m, 1H), 1.29 (t, J=7.0 Hz, 3H), 1.02-0.97 (m, 2H), 0.83-0.79 (m, 2H); ESI-MS (m/z) 336, 338 [(MH)$^+$, Br$^{79,81}$].

Step-4: 5-(1-(5-Bromopyridin-2-yl)-3-cyclopropyl-1H-pyrazol-5-yl)-3-methyl-1,3,4-oxadiazol-2(3H)-one: The title compound was prepared from step-3 intermediate by following the procedure sequentially as described in step-4, step-5 and step-6 of intermediate 1. $^1$HNMR (400 MHz, CDCl$_3$) δ 8.38 (d, J=2.0 Hz, 1H), 7.93 (dd, J=2.0 & 8.0 Hz, 1H), 7.76 (d, J=8.0 Hz, 1H), 6.54 (s, 1H), 3.51 (s, 3H), 2.06-1.99 (m, 1H), 1.06-1.01 (m, 2H), 0.89-0.87 (m, 2H); ESI-MS (m/z) 362, 364 [(MH)$^+$, Br$^{79,81}$].

Intermediate-10: 5-(1-(5-Bromopyridin-2-yl)-5-cyclopropyl-1H-pyrazol-3-yl)-3-methyl-1,3,4-oxadiazol-2(3H)-one

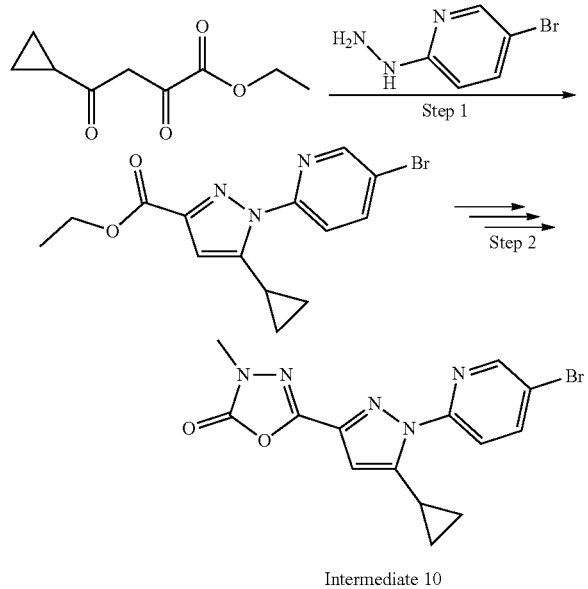

Intermediate 10

Step-1: Ethyl 1-(5-bromopyridin-2-yl)-5-cyclopropyl-1H-pyrazole-3-carboxylate: To a stirred solution of ethyl 4-cyclopropyl-2,4-dioxobutanoate (0.378 g, 2.05 mmol) in acetic acid (5 mL) was added 5-bromo-2-hydrazinylpyridine (386 mg, 2.05 mmol) at room temperature and the resulting mixture was refluxed for 2 h. The reaction was then cooled to room temperature and the solvent was evaporated under vacuum. The crude product was purified by flash column chromatography (silica gel, ethyl acetate-hexane system as eluent) to afford 300 mg (43%) of the title compound as pale yellow syrup. $^1$HNMR (400 MHz, CDCl$_3$) δ 8.55 (d, J=2.0 Hz, 1H), 7.98 (dd, J=2.0 & 8.0 Hz, 1H), 7.87 (d, J=8.0 Hz, 1H), 6.50 (s, 1H), 4.41 (q, J=7.0 Hz, 2H), 2.70-2.64 (m, 1H), 1.40 (t, J=7.0 Hz, 3H), 1.05-1.00 (m, 2H), 0.75-0.71 (m, 2H); ESI-MS (m/z) 336, 338 [(MH)$^+$Br$^{79,81}$].

Step-2: 5-(1-(5-Bromopyridin-2-yl)-5-cyclopropyl-1H-pyrazol-3-yl)-3-methyl-1,3,4-oxadiazol-2(3H)-one: The title compound was prepared from step-1 intermediate by following the procedure sequentially as described in step-4, step-5 and step-6 of intermediate-1. $^1$HNMR (400 MHz, CDCl$_3$) δ 8.55 (d, J=2.0 Hz, 1H), 7.99 (dd, J=2.0 & 8.0 Hz, 1H), 7.88 (d, J=8.0 Hz, 1H), 6.41 (s, 1H), 3.55 (s, 3H), 2.80-2.73 (m, 1H), 1.09-1.03 (m, 2H), 0.77-0.74 (m, 2H); ESI-MS (m/z) 362, 364 [(MH)$^+$, Br$^{79,81}$].

Intermediate-11: 5-(1-(5-Bromopyridin-2-yl)-5-methyl-1H-pyrazol-3-yl)-3-methyl-1,3,4-oxadiazol-2(3H)-one

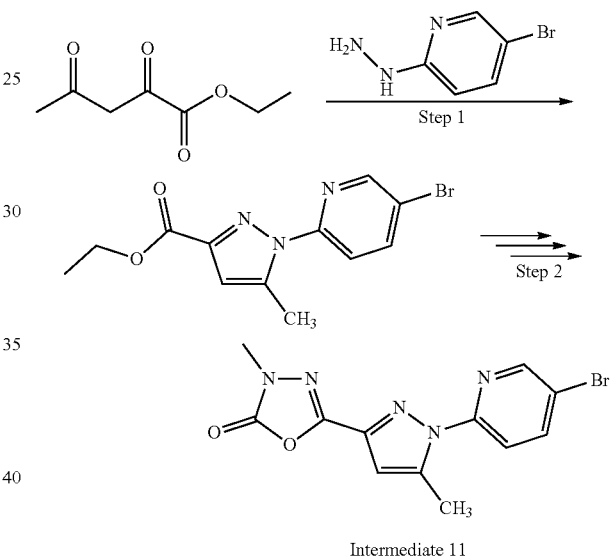

Intermediate 11

Step-1: Ethyl-1-(5-bromopyridin-2-yl)-5-methyl-1H-pyrazole-3-carboxylate: To a stirred solution of 5-bromo-2-hydrazinylpyridine (16.6 g, 89.0 mmol), in ethanol (5 mL) and acetic acid (10 mL) was added ethyl 2,4-dioxopentanoate (14.0 g, 89.0 mmol) drop-wise at 0° C. and the resulting mixture was stirred at 100° C. for 2 h. The reaction mixture was then cooled to room temperature and the solvent was evaporated under vacuum. The residue was diluted with water (50 mL) followed by ethyl acetate (100 mL). The layers were separated and the aqueous layer was extracted with ethyl acetate (2×100 mL). The combined organic layers were washed with brine (100 mL), dried (Na$_2$SO$_4$) and filtered. The filtrate was rotary evaporated and the crude product was purified by flash column chromatography (silica gel, ethyl acetate-hexanes system as eluent) to afford 2.60 g (10%) of the title compound as white solid. $^1$HNMR (400 MHz, CDCl$_3$) δ 8.51-8.50 (m, 1H), 7.96-7.93 (m, 2H), 6.71 (s, 1H), 4.41 (q, J=7.0 Hz, 2H), 2.67 (s, 3H), 1.41 (t, J=7.0 Hz, 3H); ESI-MS (m/z) 310, 312 [(MH)$^+$, Br$^{79,81}$].

Step-2: 5-(1-(5-Bromopyridin-2-yl)-5-methyl-1H-pyrazol-3-yl)-3-methyl-1,3,4-oxadiazol-2(3H)-one: The title compound was prepared from step-1 intermediate by following the procedure sequentially described in step-4, step-5 and step-6 of Intermediate-1. $^1$HNMR (400 MHz, CDCl$_3$) δ 8.53-8.52 (m, 1H), 7.98-7.93 (m, 2H), 6.62 (s, 1H), 3.53 (s, 3H), 2.72 (s, 3H); ESI-MS (m/z) 336, 338 [(MH)$^+$, Br$^{79,81}$]

Intermediate-12: Methyl 3-(1-(5-bromopyridin-2-yl)-5-(trifluoromethyl)-1H-pyrazol-3-yl)-5-methyl-4,5-dihydroisoxazole-5-carboxylate

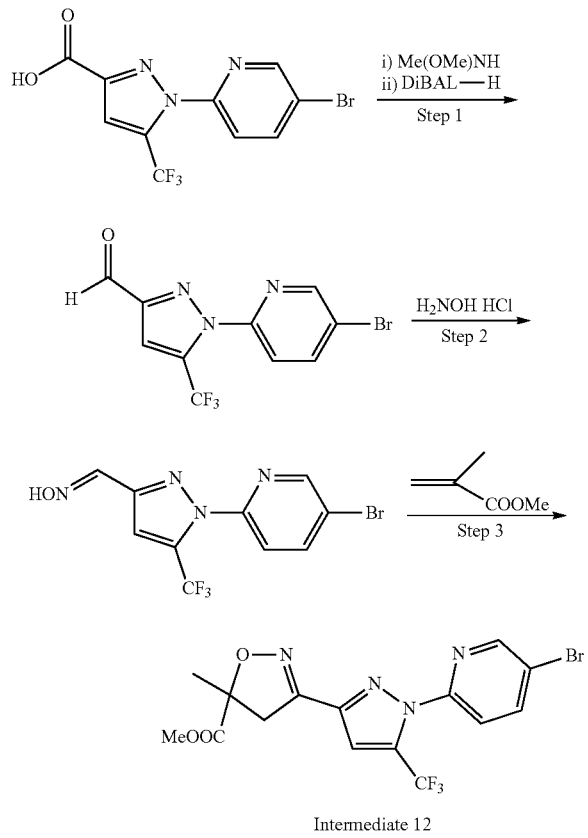

Intermediate 12

Step-1: 1-(5-Bromopyridin-2-yl)-5-(trifluoromethyl)-1H-pyrazole-3-carbaldehyde: To a stirred solution of 1-(5-bromopyridin-2-yl)-5-(trifluoromethyl)-1H-pyrazole-3-carboxylic acid (6.20 g, 18.45 mmol), in DMF (50 mL) was successively added EDC.HCl (4.24 g, 22.14 mmol), HOBT (3.11 g, 20.29 mmol), N,O-dimethylhydroxylamine hydrochloride (2.70 g, 27.7 mmol) and triethylamine (5.14 mL, 36.9 mmol). After stirring the reaction mixture at 65° C. for 12 h, the reaction was cooled to RT. Water (60 mL) was added to the above reaction followed by ethyl acetate (100 mL). The layers were separated and aqueous layer was extracted with ethyl acetate (3×100 mL). The combined organic layers were washed with water (100 mL), brine (100 mL), dried (Na$_2$SO$_4$) and filtered. The filtrate was rotary evaporated and the crude product was purified by flash column chromatography (silica gel, ethyl acetate-hexanes system as eluent) to afford 4.20 g (60%) of the 1-(5-bromopyridin-2-yl)-N-methoxy-N-methyl-5-(trifluoromethyl)-1H-pyrazole-3-carboxamide as white solid. $^1$HNMR (400 MHz, DMSO-d$_6$) δ 8.74 (d, J=2.5 Hz, 1H), 8.37 (dd, J=2.5 & 8.5 Hz, 1H), 7.88 (d, J=8.5 Hz, 1H), 7.50 (s, 1H), 3.77 (s, 3H), 3.34 (s, 3H); ESI-MS (m/z) 379, 381 [(MH)$^+$, Br$^{79,81}$].

To a −78° C. cooled and stirred solution of 1-(5-Bromopyridin-2-yl)-N-methoxy-N-methyl-5-(trifluoromethyl)-1H-pyrazole-3-carboxamide (4.40 g, 11.61 mmol) in THF (35 mL) was added DIBAL-H (1M, 29.9 mL, 29.9 mmol) over a period of 30 min. Reaction was quenched at the same temperature with hydrochloric acid (10%) and diluted with ethyl acetate (100 mL). The mixture was stirred at room temperature for 2 h and then the layers were separated. The aqueous layer was extracted with ethyl acetate (2×100 mL). The combined organic layers were washed with brine (100 mL), dried (Na$_2$SO$_4$) and filtered. The filtrate was evaporated and the crude product was purified by flash column chromatography to afford 2.60 g (70%) of the title compound as white solid. $^1$HNMR (400 MHz, CDCl$_3$) δ 10.07 (s, 1H), 8.62 (d, J=2.0 Hz, 1H), 8.08 (dd, J=2.0 & 8.0 Hz, 1H), 7.85 (d, J=8.0 Hz, 1H), 7.37 (s, 1H); ESI-MS (m/z) 320, 322 [(MH)$^+$, Br$^{79,81}$].

Step-2: 1-(5-Bromopyridin-2-yl)-5-(trifluoromethyl)-1H-pyrazole-3-carbaldehyde oxime: To a (0° C.) cooled solution of 1-(5-bromopyridin-2-yl)-5-(trifluoromethyl)-1H-pyrazole-3-carbaldehyde (2.60 g, 8.12 mmol) in methanol (30 mL) was added a solution of hydroxylamine hydrochloride (0.847 g, 12.19 mmol) in water (5 mL) followed by a solution of sodium carbonate (0.517 g, 4.87 mmol) in water (2 mL). The reaction mixture was warmed to room temperature and then stirred for 1h. The reaction mixture was diluted with water (20 mL) and diluted with ethyl acetate (100 mL). The layers were separated and the aqueous layer was extracted with ethyl acetate (2×50 mL). The combined organic layers were washed with brine (50 mL), dried (Na$_2$SO$_4$) and filtered. The filtrate was concentrated under vacuum to afford 2.60 g (96%) as white solid. $^1$HNMR (400 MHz, CDCl$_3$) δ 8.57 (d, J=2.0 Hz, 1H), 8.23 (s, 1H), 7.98 (dd, J=2.0 & 8.0 Hz, 1H), 7.78 (d, J=8.0 Hz, 1H), 7.67 (s, 1H), 7.19 (s, 1H), ESI-MS (m/z) 335, 337 [(MH)$^+$, Br$^{79,81}$].

Step-3: Methyl 3-(1-(5-bromopyridin-2-yl)-5-(trifluoromethyl)-1H-pyrazol-3- yl)-5-methyl-4,5-dihydroisoxazole-5-carboxylate: To a stirred solution of step-2 intermediate (3.0 g, 8.95 mmol) in THF (100 mL) was added NCS (1.79 g, 13.43 mmol) and pyridine (434 µL, 5.37 mmol) at 0° C. and then stirred at 60° C. for 3 h. The reaction was then cooled back down to 0° C., methyl methacrylate (1.43 mL, 13.43 mmol) and triethylamine (2.49 mL, 17.91 mmol) were added sequentially to the above mixture and the resulting mixture was stirred at 45° C. for 6 h. The reaction mixture was cooled to room temperature and then diluted with water (50 mL) followed by ethyl acetate (100 mL). The layers were separated and the aqueous layer was extracted with ethyl acetate (2×50 mL). The combined organic layers were washed with brine (50 mL), dried (Na$_2$SO$_4$) and filtered. The filtrate was rotary evaporated and the crude product was purified by flash column chromatography (silica gel, ethyl acetate-hexanes system as eluent) to afford 2.0 g (51%) of the title compound as white solid. $^1$HNMR (400 MHz, CDCl$_3$) δ 8.58 (d, J=2.0 Hz, 1H), 8.01-7.98 (dd, J=2.0 & 8.0 Hz, 1H), 7.76 (d, J=8.0 Hz, 1H), 7.32 (s, 1H), 4.00 (d, J=17.0 Hz, 1H), 3.81(s, 3H), 3.36 (d, T=17.0 Hz, 1H), 1.74 (s, 3H); ESI-MS (m/z) 433, 435 [(MH)$^+$, Br$^{79,81}$].

Intermediate-13a: 1-(5-Bromopyridin-2-yl)-3-(furan-2-yl)-1H-pyrazole-5-carboxylic acid And Intermediate-13b: 1-(5-Bromopyridin-2-yl)-5-(furan-2-yl)-1H-pyrazole-3-carboxylic acid

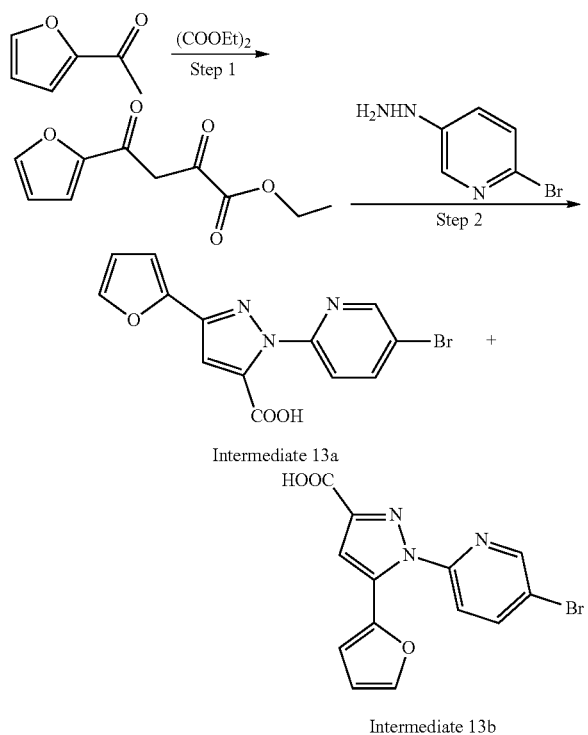

Step-1: Ethyl 4-(furan-2-yl)-2,4-dioxobutanoate: To a (0° C.) cooled and stirred suspension of sodium hydride (60% suspension in mineral oil, 5.45 g, 136 mmol) in THF (100 mL) was added drop-wise a solution of diethyl oxalate (12.4 mL, 91 mmol) over a period of 30 min. The resulting mixture was then warmed to room temperature and then continued stirring for 30 min at the same temperature. A solution of 1-(furan-2-yl)ethanone (5.0 g, 45.4 mmol) in THF (25 mL) was then added to the above mixture at room temperature and the resulting mixture was slowly warmed to 50° C. and continued stirring at the same temperature for 5 h. The reaction mixture was cooled down to room temperature and then quenched with aqueous hydrochloric acid (10%, 10 mL) followed by the addition of water (50 mL) and ethyl acetate (100 mL). The layers were separated and the aqueous layer was extracted with ethyl acetate (2×100 mL). The combined organic layers were washed with brine (100 mL), dried ($Na_2SO_4$) and filtered. The filtrate was rotary evaporated to afford 9.54 g (100%) of the title compound as semisolid. ESI-MS (m/z) 211 [(MH)$^+$ Step-2: 1-(5-Bromopyridin-2-yl)-3-(furan-2-yl)-1H-pyrazole-5-carboxylic acid and 1-(5-Bromopyridin-2-yl)-5-(furan-2-yl)-1H-pyrazole-3-carboxylic acid: A mixture of ethyl 4-(furan-2-yl)-2,4-dioxobutanoate (1.0 g, 4.76 mmol) and 5-bromo-2-hydrazinylpyridine (895 mg, 4.76 mmol) in acetic acid (6 mL) and ethanol (6 mL) was heated at 100° C. for 1 h. The reaction mixture was cooled to room temperature and the solvent was evaporated under vacuum. The crude product was purified by flash column chromatography to afford 60 mg (4%) of intermediate 13a and 200 mg (12%) of the intermediate 13b as white solids.

Intermediate-13a: 1-(5-Bromopyridin-2-yl)-3-(furan-2-yl)-1H-pyrazole-5-carboxylic acid: $^1$HNMR (400 MHz, DMSO-$d_6$) δ13.25 (s, 1H, $D_2O$ exchangeable), 8.67 (d, J=2.0 Hz, 1H), 8.35 (dd, J=8.0 & 2.0 Hz, 1H), 7.76-7.72 (m, 2H), 7.17 (s, 1H), 6.67-6.66 (m, 1H), 6.56-6.55 (m, 1H); ESI-MS (m/z) 334, 336 [(MH)$^+$, $Br^{79,81}$].

Intermediate-13b: 1-(5-Bromopyridin-2-yl)-5-(furan-2-yl)-1H-pyrazole-3-carboxylic acid: $^1$HNMR (400 MHz, DMSO-$d_6$) δ13.68 (s, 1H, $D_2O$ exchangeable), 8.66 (d, J=2.0 Hz, 1H), 8.35 (dd, J=8.0 & 2.0 Hz, 1H), 7.80-7.74 (m, 2H), 7.28 (s, 1H), 6.99-6.98 (m, 1H), 6.64-6.63 (m, 1H); ESI-MS (m/z) 334, 336 [(MH)$^+$, $Br^{79,81}$].

Intermediate-14: 5-(1-(5-Bromopyridin-2-yl)-5-(difluoromethyl)-1H-pyrazol-3-yl)-3-methyl-1,3,4-oxadiazol-2(3H)-one

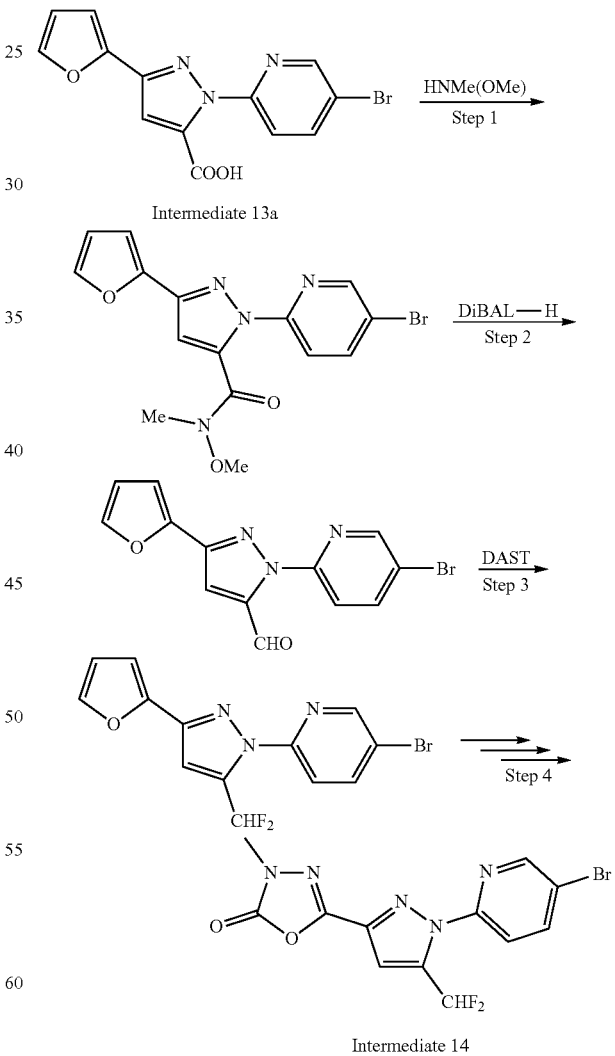

Step-1: 1-(5-Bromopyridin-2-yl)-3-(furan-2-yl)-N-methoxy-N-methyl-1H-pyrazole-5-carboxamide: To a stirred solution of 1-(5-bromopyridin-2-yl)-3-(furan-2-yl)-1H-pyrazole-5-carboxylic acid (500 mg, 1.49 mmol) in THF (10 mL) was successively added EDC.HCl (430 mg, 2.24 mmol), HOBT (344 mg, 2.24 mmol), N,O-dimethylhydroxylamine hydrochloride (219 mg, 2.24 mmol) and triethylamine 417 µL, 2.99 mmol). The resulting mixture was stirred at room temperature for 16 h. The reaction was then diluted with water (10 mL) followed by ethyl acetate (10 mL). The layers were separated and the aqueous layer was extracted with ethyl acetate (3×25 mL). The combined organic layers were washed with brine (20 mL), dried ($Na_2SO_4$) and filtered. The filtrate was rotary evaporated and the crude product was purified by flash column chromatography (silica gel, ethyl acetate-hexanes system as eluent) to afford 300 mg (7%) of the desired product as white solid. $^1$HNMR (400 MHz, $CDCl_3$) δ 8.01 (d, J=2.0 Hz, 1H), 7.96-7.89 (m, 2H), 7.53-7.50 (m, 1H), 6.83-6.82 (m, 2H), 6.53-6.52 (m, 1H), 3.48 (s, 3H), 3.36 (s, 3H); (ESI-MS (m/z) 377, 379 [(MH)$^+$, $Br^{79,81}$]

Step-2: 1-(5-Bromopyridin-2-yl)-3-(furan-2-yl)-1H-pyrazole-5-carbaldehyde: To a −78° C. cooled and stirred solution of step-1 intermediate (10.0 g, 26 5 mmol) in THF (40 mL) was added drop-wise DIBAL-H (1M in THF, 53.0 mL, 53 0 mmol) over a period of 30 min. The reaction was gradually warmed to room temperature and stirred overnight. The reaction was then cooled to 0° C. and quenched with aqueous hydrochloric acid (10%, 50 mL) followed by the addition of water (50 mL) and ethyl acetate (100 mL). The layers were separated and the aqueous layer was extracted with ethyl acetate (2×100 mL). The combined organic layers were washed with brine (100 mL), dried ($Na_2SO_4$) and filtered. The filtrate was rotary evaporated and the crude product was purified by flash column chromatography to afford 1.50 g (17%) of the title compound as white solid. $^1$HNMR (400 MHz, DMSO-$d_6$) δ 10.43 (s, 1H), 8.72 (d, J=2.0 Hz, 1H), 8.34 (dd, J=8.0 & 2.0 Hz, 1H), 7.93 (d, J=8.0 Hz, 1H), 7.84-7.83 (m, 1H), 7.44 (s, 1H), 7.08-7.07 (m, 1H), 6.67-6.65 (m, 1H). (ESI-MS (m/z) 318, 320 [(MH)$^+$, $Br^{79,81}$]

Step-3: 5-Bromo-2-(5-(difluoromethyl)-3-(furan-2-yl)-1H-pyrazol-1-yl)pyridine: To a cooled (−35° C.) and stirred solution of step-2 intermediate (4.0 g, 12.57 mmol) in DCM (100 mL) was added DAST (4.15 mL, 31.4 mmol) drop-wise and the reaction was gradually warmed to room temperature and then stirred at the same temperature overnight. The reaction mixture was diluted with water (50 mL) followed by DCM (50 mL). The layers were separated and the aqueous layer was extracted with DCM (2×100 mL). The combined organic layers were washed with brine (100 mL), dried ($Na_2SO_4$) and filtered. The filtrate was rotary evaporated and the crude product was purified by flash column chromatography to afford 2.70 g (63%) of the title compound as white solid. $^1$HNMR (400 MHz, DMSO-$d_6$) δ 8.64 (d, J=2.0 Hz, 1H), 8.28 (dd, J=8.0 & 2.0 Hz, 1H), 7.93 (d, J=8.0 Hz, 1H), 7.84-7.83 (m, 1H), 7.77 (t, J=50 Hz, 1H), 7.29 (s, 1H), 7.07-7.06 (m, 1H), 6.66-6.65 (m, 1H); (ESI-MS (m/z) 340, 342 [(MH)$^+$, $Br^{79,81}$].

Step-4: 5-(1-(5-Bromopyridin-2-yl)-5-(difluoromethyl)-1H-pyrazol-3-yl)-3-methyl-1,3,4-oxadiazol-2(3H)-one: The title compound was prepared from step-3 intermediate by following the similar procedure sequentially as described in step-4, step-5 and step-6 of intermediate-1. $^1$HNMR (400 MHz, $Cd_3CN$) δ 8.60 (d, J=2.0 Hz, 1H), 8.17 (dd, J=8.0 & 2.0 Hz, 1H), 7.96 (d, J=8.0 Hz, 1H), 7.72 (t, J=50 Hz, 1H), 7.28 (s, 1H), 3.45 (s, 3H); (ESI-MS (m/z) 372, 374 [(MH)$^+$, $Br^{79,81}$].

Intermediate-15: 5-(1-(5-Bromopyridin-2-yl)-3-(difluoromethyl)-1H-pyrazol-5-yl)-3-methyl-1,3,4-oxadiazol-2(3H)-one

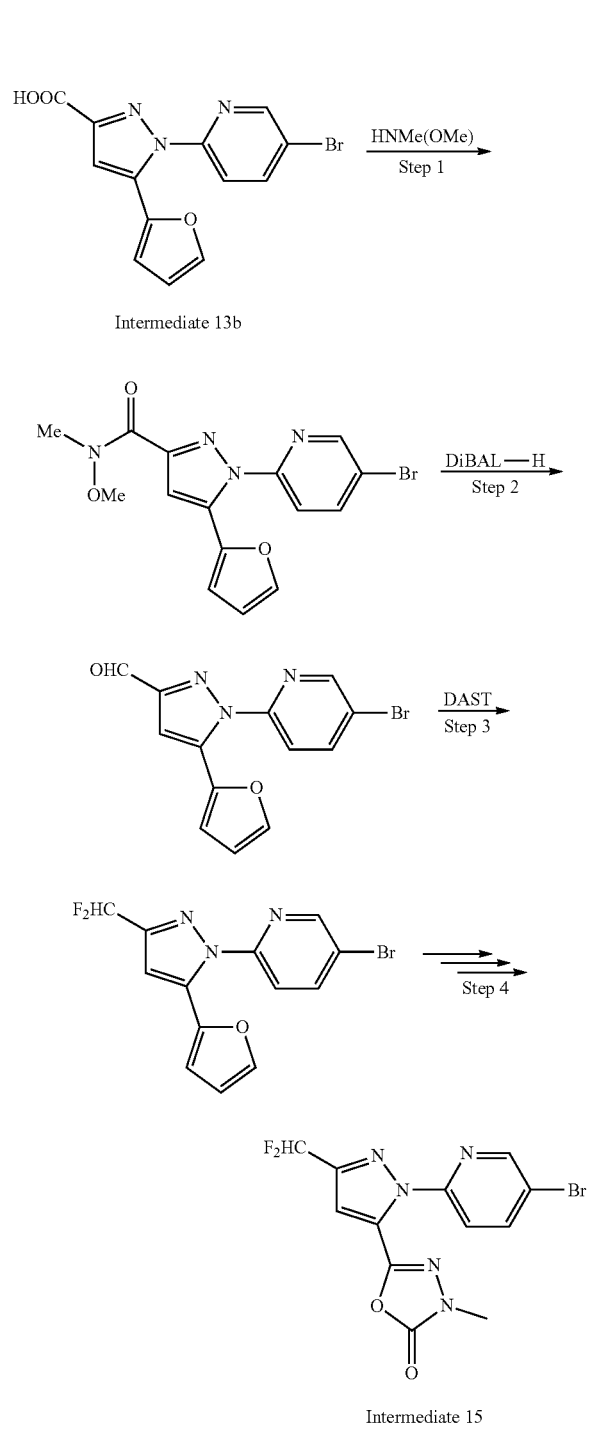

Intermediate 15

The title compound was prepared from Intermediate 13b by following the similar procedure as described in Intermediate-14. $^1$HNMR (400 MHz, DMSO-$d_6$) δ 8.66 (d, J=2.0 Hz, 1H), 8.36 (dd, J=8.0 &2.0 Hz, 1H), 7.87 (d, J=8.0 Hz, 1H), 7.42 (s, 1H), 7.23 (t, J=50 Hz, 1H), 3.40 (s, 3H); (ESI-MS (m/z) 372, 374 [(MH)$^+$, $Br^{79,81}$].

Intermediate-16: 5-(1-(5-Bromopyridin-2-yl)-5-(fluoromethyl)-1H-pyrazol-3-yl)-3-methyl-1,3,4-oxadiazol-2(3H)-one

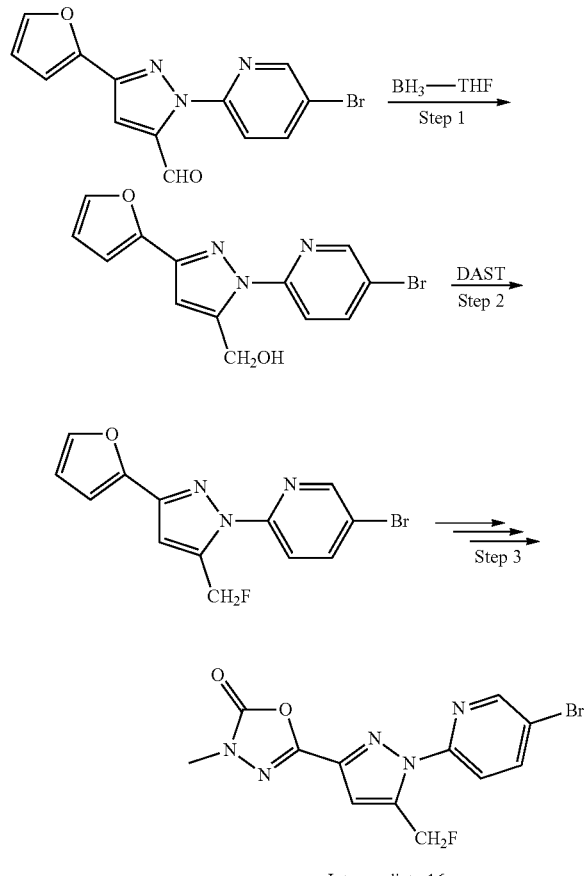

Intermediate 16

Step-1: (1-(5-Bromopyridin-2-yl)-3-(furan-2-yl)-1H-pyrazol-5-yl)methanol: To a stirred solution of 1-(5-bromopyridin-2-yl)-3-(furan-2-yl)-1H-pyrazole-5-carbaldehyde (5.0 g, 15.72 mmol) in THF (40 mL) was added borane-THF complex (1M, 31.4 mL, 31.4 mmol) drop-wise at 0° C. over a period of 15 min. The reaction was gradually warmed to room temperature and then stirred at the same temperature for 2 h. The reaction was cooled to 0° C. and then quenched with ice cold water (10 mL) followed by the addition of ethyl acetate (50 mL). The layers were separated and the aqueous layer was extracted with ethyl acetate (2×100 mL). The combined organic layers were washed with brine (50 mL), dried (Na$_2$SO$_4$) and filtered. The filtrate was rotary evaporated and the crude product was purified by flash column chromatography (silica gel, ethyl acetate-hexanes system as eluent) to afford 2.0 g (40%) of the title compound as white solid. $^1$HNMR (400 MHz, CDCl$_3$) δ 8.48 (d, J=2.0 Hz, 1H), 8.0 (d, J=8.0 Hz, 1H), 8.00 (dd, J=8.0 & 2.0 Hz, 1H), 7.53-7.51 (m, 1H), 6.79-6.78 (m, 1H), 6.65 (s, 1H), 6.52-6.50 (m, 1H), 5.28 (s, 1H), 4.76 (s, 2H); ESI-MS (m/z) 320, 322 [(MH)$^+$, Br$^{79,81}$]

Step-2: 5-Bromo-2-(5-(fluoromethyl)-3-(furan-2-yl)-1H-pyrazol-1-yl)pyridine: To a (−78° C.) cooled and stirred solution of step-1 intermediate (2.0 g, 6.25 mmol) in DCM (30 mL) was drop-wise added DAST (1.65 mL, 12.49 mmol) and the reaction was then warmed to −40° C. and then stirred for 2 h at that temperature. The reaction was diluted with water (30 mL) at −40° C. followed by the addition of DCM (50 mL). The layers were separated and the aqueous layer was extracted with DCM (2×50 mL). The combined organic layers were washed with brine (50 mL), dried (Na$_2$SO$_4$) and filtered. The filtrate was rotary evaporated and the crude product was purified by flash column chromatography to afford 1.10 g (54%) of the title compound as white solid. $^1$HNMR (400 MHz, DMSO- d$_6$) δ 8.62 (d, J=2.0 Hz, 1H), 8.25 (dd, J=8.0 & 2.0 Hz, 1H), 7.91 (d, J=8.0 Hz, 1H), 7.81 (m, 1H), 7.00-6.99 (m, 1H), 6.97 (s, 1H), 6.65-6.63 (m, 1H), 5.93 (d, J=50 Hz, 2H); (ESI-MS (m/z) 322, 324 [(MH)$^+$, Br$^{79,81}$].

Intermediate-17: 5-Hydrazinyl-2-nitropyridine hydrochloride

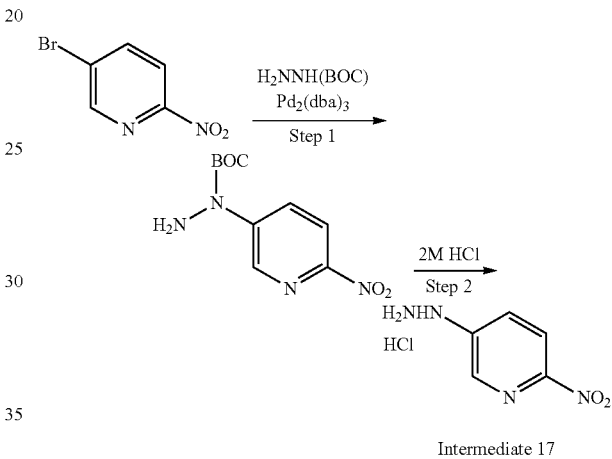

Intermediate 17

Step-1: tert-butyl 1-(6-nitropyridin-3-yl)hydrazinecarboxylate: To a nitrogen purged solution of 5-bromo-2-nitropyridine (50 g, 246 mmol) and tert-butyl hydrazinecarboxylate (26.0 g, 197 mmol) in toluene (500 mL) in a sealed tube, cesium carbonate (93.0 g, 286 mmol), dppf (20.48 g, 36.9 mmol) and Pd$_2$(dba)$_3$ (15.79 g, 17.24 mmol) were sequentially added. The resulting mixture was thoroughly deoxygenated by flushing nitrogen gas for 15 min and the resulting mixture was stirred at 100° C. for 5 h. The reaction mixture was cooled to room temperature and then filtered through celite. The filtrate was rotary evaporated and the crude product was purified by flash column chromatography (silica gel, ethyl acetate-hexanes system as eluent) to afford 23.0 g (38%) of the title compound as a yellow solid. $^1$HNMR (400 MHz, CDCl$_3$) δ 9.0 (d, J=2.5 Hz, 1H), 8.36 (dd, J=2.5 & 8.5 Hz, 1H), 8.22 (d, J=8.5 Hz, 1H), 4.47 (s, 2H, D$_2$O exchangeable) 1.61 (s, 9H); GCMS (m/z) 154 (M-Boc)$^+$ Step-2: 5-Hydrazinyl-2-nitropyridine hydrochloride: To (0° C.) cooled solution of tert-butyl 1-(6-nitropyridin-3-yl)hydrazinecarboxylate (5.0 g, 19.67 mmol) in dry 1,4-dioxane (250 mL) was added aqueous hydrochloric acid (2N, 98 mL). After stirring for 16 h at 25° C., the solvent was evaporated under vacuum. The residue was triturated with hexane and dried under vacuum to afford 2.70 g (89%) of the title compound as pink solid. $^1$HNMR (400 MHz, DMSO- d$_6$) δ 10.75 (brs, 2H, D$_2$O exchangeable), 9.75 (s, 1H, D$_2$O exchangeable), 8.32 (d, J=8.5 Hz, 1H), 8.21 (d, J=2.5 Hz, 1H), 7.55(dd, J=2.5 & 8.5 Hz, 1H).

Intermediate-18: 5-(1-(6-Aminopyridin-3-yl)-5-(trifluoromethyl)-1H-pyrazol-3-yl)-3-methyl-1,3,4-oxadiazol-2(3H)-one

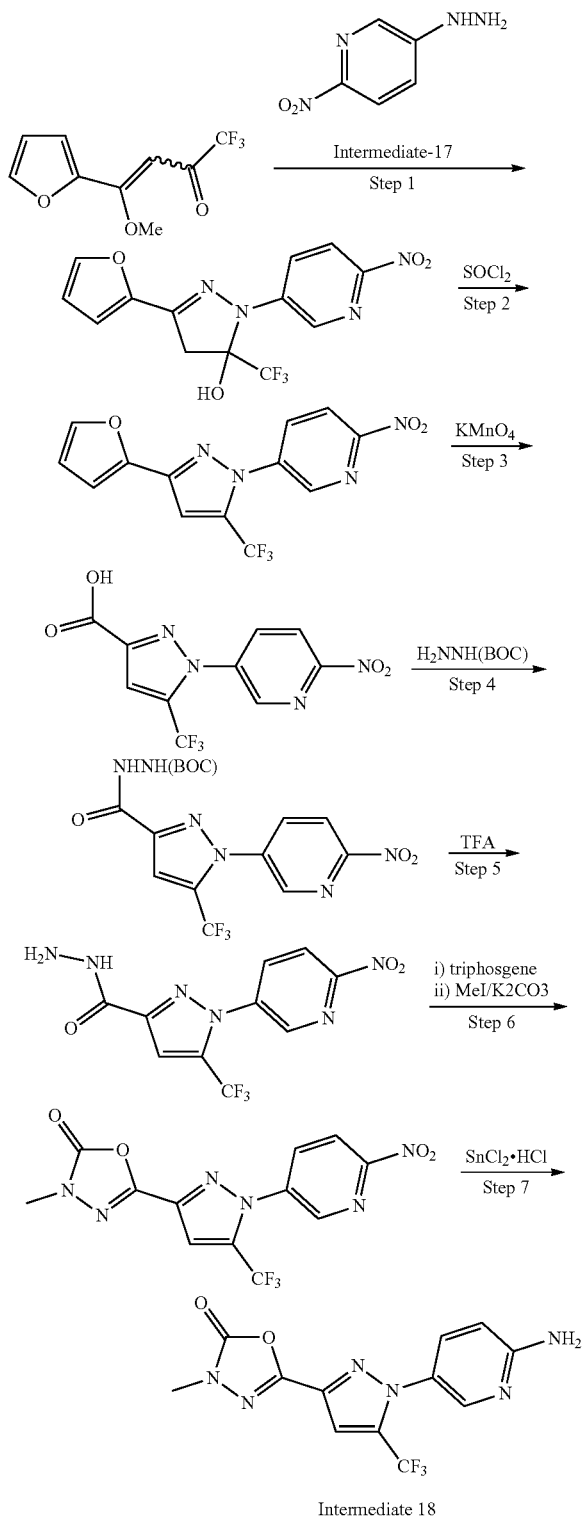

Intermediate 18

Step-1: 3-(Furan-2-yl)-1-(6-nitropyridin-3-yl)-5-(trifluoromethyl)-4,5-dihydro-1H-pyrazol-5-ol: To a stirred solution of Intermediate-17, (17.0 g, 89 mmol) in ethanol (50 mL) was added DIPEA (31.2 mL, 178 mmol) at 0° C. and stirred for 30 min. The resulting mixture was added drop-wise to a 0° C. cooled solution of 1,1,1-trifluoro-4-(furan-2-yl)-4-methoxybut-3-en-2-one (23.5 g, 107 mmol) in ethanol (20 mL). The resulting mixture was warmed to room temperature and then stirred at 45° C. overnight. The solvent was removed under reduced pressure and the residue was purified by flash column chromatography (silica gel, 30% ethyl acetate-hexanes system as eluent) to afford 12.0 g (30%) of the title compound as a pink solid. $^1$HNMR (400 MHz, DMSO-d$_6$) δ 9.03 (s, 1H, D$_2$O exchangeable), 8.65 (d, J=2.5 Hz, 1H), 8.34 (d, J=8.5 Hz, 1H), 8.02 (dd, J=2.5 & 8.5 Hz, 1H), 7.94 (d, J=1.5 Hz, 1H), 7.12 (d, J=3.0 Hz, 1H), 6.72 (dd, J=1.5 & 3.0 Hz, 1H), 4.00 (d, J=19.0 Hz, 1H), 3.66 (d, J=19.0 Hz, 1H); ESI-MS (m/z) 343 (MH)$^+$.

Step-2: 5-(3-(Furan-2-yl)-5-(trifluoromethyl)-1H-pyrazol-1-yl)-2-nitropyridine: To a (0° C.) cooled solution of step-1 intermediate (1.50 g, 4.38 mmol) in DCM (15 mL) was added SOCl$_2$ (0.70 mL, 9.64 mmol). After stirring for 15 min at 0° C., pyridine (0.88 mL, 10.9 mmol) was added at the same temperature and the resulting mixture was stirred for 30 min at 0° C. The solvent was removed under reduced pressure and the residue was dissolved in ice cooled water (30 mL) and ethyl acetate (25 mL). The layers were separated and the aqueous layer was extracted with ethyl acetate (2×50 mL). The combined organic layers were washed with saturated aqueous NaHCO$_3$ solution (50 mL), dried (Na$_2$SO$_4$) and filtered. The filtrate was concentrated under vacuum and the crude product was purified by flash column chromatography (silica gel, ethyl acetate-hexanes system as eluent) to afford 1.0 g (74%) of the title compound as a white solid. $^1$HNMR (400 MHz, CDCl$_3$) δ 8.94 (d, J=2.5 Hz, 1H), 8.45 (d, J=8.5 Hz, 1H), 8.30 (dd, J=2.5 & 8.5 Hz, 1H), 7.56 (d, J=1.5 Hz, 1H), 7.27 (s, 1H), 6.89 (d, J=3.0 Hz, 1H), 6.56 (dd, J=1.5 & 3.0 Hz, 1H); ESI-MS (m/z) 325 (MH)$^+$.

Step-3: 1-(6-Nitropyridin-3-yl)-5-(trifluoromethyl)-1H-pyrazole-3-carboxylic acid: The title compound was prepared by reacting step-2 intermediate (4.0 g, 12.34 mmol) with potassium permanganate (13.0 g, 83 mmol) by following the similar procedure as described in Step-2 of Intermediate-1 to afford 3.0 g (80%) of the desired product as a white solid. $^1$HNMR (400 MHz, DMSO- d$_6$) δ 8.99 (d, J=1.5 Hz, 1H), 8.60-8.57 (m, 2H), 7.71 (s, 1H); ESI-MS (m/z) 302 (MH)$^+$.

Step-4: tert-Butyl 2-(1-(6-nitropyridin-3-yl)-5-(trifluoromethyl)-1H-pyrazole-3-carbonyl) hydrazinecarboxylate: To a stirred solution of step-3 intermediate (2.50 g, 8.27 mmol) in DCM (25 mL) was successively added EDC.HCl (2.37 g, 12.41 mmol), HOBT (0.634 g, 4.14 mmol) and tert-butylhydrazine carboxylate (1.093 g, 8.27 mmol). After stirring at room temperature for 6 h, the reaction mixture was diluted with water (10 mL) and dichloromethane (30 mL). The layers were separated and aqueous layer was extracted with dichloromethane (3×20mL). The combined organic layers were washed with brine (50 mL), dried (Na$_2$SO$_4$) and filtered. The filtrate was rotary evaporated and the crude product was purified by flash column chromatography to afford 2.0 g (58%) of the title compound as a white solid. $^1$HNMR (400 MHz, CDCl$_3$) δ 8.89 (d, J=2.5 Hz, 1H), 8.53 (s, 1H, D$_2$O exchangeable), 8.49 (d, J=8.5 Hz, 1H), 8.27 (dd, J=2.5 & 8.5 Hz, 1H), 7.85 (s, 1H, D$_2$O exchangeable), 7.51(s, 1H), 1.51 (s, 9H); ESI-MS (m/z) 317 (M-Boc)$^+$.

Step-5: 1-(6-Nitropyridin-3-yl)-5-(trifluoromethyl)-1H-pyrazole-3-carbohydrazide: To a (0° C.) cooled solution of step-4 intermediate (2.0 g, 4.80 mmol) in dichloromethane (25 mL) was added drop-wise trifluoroacetic acid (3.70 mL, 48.0 mmol). After stirring the reaction mixture at room temperature for 18 h, the solvent was evaporated under reduced pressure. The crude product was triturated with diethyl ether to obtain 1.32 g (87%) of the title compound as semi solid. The residue was used for next step without further purification. ESI-MS (m/z) 317 (MH)$^+$.

Step-6: 3-Methyl-5-(1-(6-nitropyridin-3-yl)-5-(trifluoromethyl)-1H-pyrazol-3-yl)-1,3,4-oxadiazol-2(3H)-one:
The title compound was prepared from step-5 intermediate by following the similar procedure sequentially as described in Step-5 and Step-6 of Intermediate-1. ¹HNMR (400 MHz, CDCl₃) δ 8.91(d, J=2.5 Hz, 1H), 8.48 (d, J=8.5 Hz, 1H), 8.31(dd, J=2.5 & 8.5 Hz, 1H), 7.37 (s, 1H), 3.53 (s, 3H); ESI-MS (m/z) 398 (M+acetonitrile).

Step-7: 5-(1-(6-Aminopyridin-3-yl)-5-(trifluoromethyl)-1H-pyrazol-3-yl)-3-methyl-1,3,4-oxadiazol-2(3H)-one: To a 0° C. cooled and stirred solution of Step-6 intermediate (500 mg, 1.40 mmol) in ethanol (10 mL) and hydrochloric acid (1M, 0.5 mL) was added iron powder (800 mg, 14 mmol, 10 eq) portion-wise. The resulting mixture was then stirred at 95° C. for 2 h. The reaction was then cooled down to 0° C., poured in ice water and basified with aqueous ammonia solution followed by the addition of ethyl acetate (20 mL). The layers were separated and the aqueous layer was extracted with ethyl acetate (2×25 mL). The combined organic layers were washed with brine (50 mL), dried (Na₂SO₄) and filtered. The filtrate was rotary evaporated to afford 400 mg (87%) of the title product as a white solid. ¹HNMR (400 MHz, DMSO-d₆) ¹HNMR (400 MHz, CDCl₃) δ 8.06 (d, J=2.0 Hz, 1H), 7.62 (s, 1H), 7.55 (dd, J=2.5, 8.5 Hz, 1H), 6.61 (s, 2H, D₂O exchangeable), 6.55 (d, J=8.5 Hz, 1H), 3.41 (s, 3H); ESI-MS (m/z) 327 (MH)⁺.

EXAMPLES

Example-1

2,6-Difluoro-N-(6-(5-(4-methyl-5-oxo-4,5-dihydro-1,3,4-oxadiazol-2-yl)-3-(trifluoromethyl)-1H-pyrazol-1-yl)pyridin-3-yl)benzamide

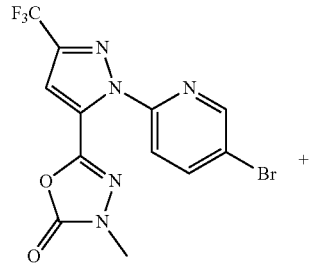

Intermediate 1

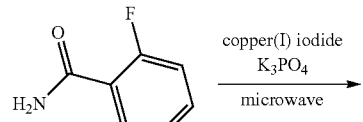

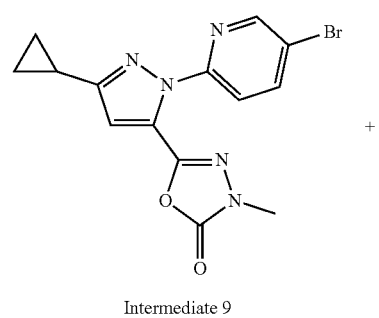

Example 1

To a nitrogen purged solution of Intermediate-1 (200 mg, 0.51 mmol) in dioxane (5 mL), was added potassium phosphate (268 mg, 1.54 mmol), 2,6-difluorobenzamide (161 mg, 1.02 mmol), trans1,2-diaminocyclohexane (25 μL, 0.205 mmol) and copper(I) iodide (39 mg, 0.205 mmol) sequentially. The resulting mixture was thoroughly deoxygenated by purging nitrogen gas for 15 min and then the resulting mixture was stirred at 110° C. for (30 min×2) in a microwave (Biotage). The reaction mixture was cooled down to room temperature and then filtered through celite. The filtrate was evaporated and the crude product was purified by flash column chromatography (silica gel, 30% ethyl acetate-hexanes system as eluent) to afford 45 mg (18%) of the desired product as white solid. ¹HNMR (400 MHz, CDCl₃) δ 8.55 (d, J=2.5 Hz, 1H), 8.50 (dd, J=2.5 & 8.5 Hz, 1H), 7.97 (s, 1H, D₂O exchangeable), 7.91(d, J=8.5 Hz, 1H), 7.52-7.48 (m, 1H), 7.12 (s, 1H), 7.06 (t, J=8.5 Hz, 2H), 3.49 (s, 3H) ; ESI-MS (m/z) 467 (MH)⁺.

Example-2

2-Fluoro-6-methyl-N-(6-(5-(4-methyl-5-oxo-4,5-dihydro-1,3,4-oxadiazol-2-yl)-3-(trifluoromethyl)-1H-pyrazol-1-yl)pyridin-3-yl)benzamide

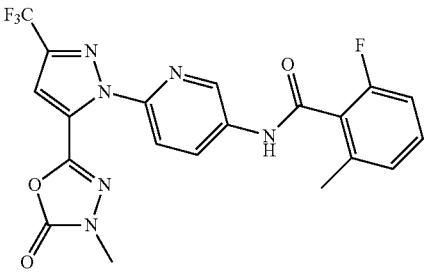 [SMILES: Cc1cccc(F)c1C(=O)Nc1ccc(-n2nc(C(F)(F)F)cc2-c2nn(C)c(=O)o2)nc1]

The title compound was prepared by following the similar procedure as described in Example-1 by using Intermediate-1 and 2-fluoro-6-methylbenzamide. ¹HNMR (400 MHz, CDCl₃) δ 8.55 (s, 1H, D₂O exchangeable), 8.50 (d, J=8.5 Hz, 1H), 7.91-7.88 (m, 2H), 7.38-7.32 (m, 1H), 7.12 (s, 1H) 7.10 (d, J=8.0 Hz, 1H), 7.01 (t, J=8.0 Hz, 1H), 3.49 (s, 3H), 2.50 (s, 3H); ESI-MS (m/z) 463 (MH)⁺.

Example-3

5-(3-Cyclopropyl-1-(5-((2,6-difluorobenzyl)amino)pyridin-2-yl)-1H-pyrazol-5-yl)-3-methyl-1,3,4-oxadiazol-2(3H)-one Intermediate 9

-continued

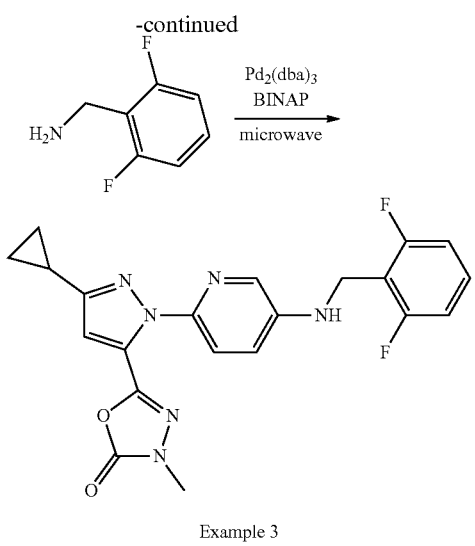

Example 3

In a microwave vial containing toluene (10 mL) and cesium carbonate (360 mg, 1.104 mmol) was purged nitrogen gas for 30 min and then Intermediate-9 (200 mg, 0.552 mmol), (2,6-difluorophenyl)methanamine (95 mg, 0.663 mmol) and BINAP (34.4 mg, 0.055 mmol) were sequentially added. The resulting mixture was thoroughly deoxygenated by purging nitrogen gas for another 15 min and then $Pd_2(dba)_3$ (37.9 mg, 0.041 mmol) was added to the above mixture. Microwave vial was then sealed and kept in microwave reactor and stirred at 125° C. for 1 h. The reaction mixture was cooled to room temperature and filtered through celite. The filtrate was rotary evaporated and the crude product was purified by flash column chromatography (silica gel, ethyl acetate-hexanes system as eluent) to afford 12 mg (5%) of the title compound as white solid. $^1$HNMR (400 MHz, DMSO-$d_6$) δ 7.78 (s, 1H), 7.47-7.42 (m, 2H), 7.22-7.13 (m, 3H), 6.71 (s, 1H), 6.11 (brs, 1H, $D_2O$ exchangeable), 4.34 (d, J=4.0 Hz, 2H), 3.34 (s, 3H), 2.10-1.90 (m, 1H), 0.95-0.93 (m, 2H), 0.80-0.76 (m, 2H); ESI-MS (m/z) 425 (MH)$^+$ The below Examples 4 to 7 given in Table-1 were prepared by following the similar procedure as described in Example-3 by using appropriate intermediate of Intermediate-12, Intermediate-15 or Intermediate-16 and appropriate amine or amide Intermediate.

TABLE 1

| Example No: IUPAC name | Structure | $^1$H-NMR/ESI-MS |
|---|---|---|
| Example-4: N-(6-(3-(Difluoromethyl)-5-(4-methyl-5-oxo-4,5-dihydro-1,3,4-oxadiazol-2-yl)-1H-pyrazol-1-yl)pyridin-3-yl)-2,6-difluorobenzamide | | $^1$HNMR (400 MHz, DMSO-$d_6$) δ 11.38 (s, 1H), 8.74 (d, J = 2.0 Hz, 1H), 8.41 (dd, J = 8.0 & 2.0 Hz, 1H), 7.92 (d, J = 8.0 Hz, 1H), 7.69-7.61 (m, 1H), 7.40 (s, 1H), 7.31 (t, J = 8.0 Hz, 2H), 7.23 (t, J = 50 Hz, 1H), 3.40 (s, 3H); ESI-MS (m/z) 449 (MH)$^+$ |
| Example-5: 5-(1-(5-((2,6-Difluorobenzyl)amino)pyridin-2-yl)-5-(fluoromethyl)-1H-pyrazol-3-yl)-3-methyl-1,3,4-oxadiazol-2(3H)-one | | $^1$HNMR (400 MHz, DMSO-$d_6$) δ 7.90 (d, J = 2.0 Hz, 1H), 7.64 (d, J = 8.0 Hz, 1H), 7.48-7.40 (m, 1H), 7.29 (dd, J = 8.0 & 2.0 Hz, 1H), 7.15 (t, J = 8.0 Hz, 2H), 7.01 (s, 1H), 6.70 (t, J = 5.0 Hz, 1H, $D_2O$ exchangeable), 5.83 (d, J = 50 Hz, 2H), 4.37 (d, J = 5.0 Hz, 2H), 3.35 (s, 3H); ESI-MS (m/z) 417 (MH)$^+$ |
| Example-6: Methyl 3-(1-(5-((2,6-difluorobenzyl)amino)pyridin-2-yl)-5-(trifluoromethyl)-1H-pyrazol-3-yl)-5-methyl-4,5-dihydroisoxazole-5-carboxylate | | $^1$HNMR (400 MHz, DMSO-$d_6$) δ 7.91 (d, J = 2.0 Hz, 1H), 7.50 (d, J = 8.0 Hz, 1H), 7.46-7.42 (m, 1H), 7.40 (s, 1H), 7.25-7.23 (dd, J = 2.0 & 8.0 Hz, 1H), 7.15 (t, J = 8.0 Hz, 2H), 6.85 (t, J = 5.0 Hz, 1H, $D_2O$ exchangeable), 4.36 (d, J = 5.0 Hz, 2H), 3.83 (d, J = 17.0 Hz, 1H), 3.69 (s, 3H), 3.44 (d, J = 17.0 Hz, 1H), 1.59 (s, 3H); ESI-MS (m/z) 496 (MH)$^+$ |

TABLE 1-continued

| Example No: IUPAC name | Structure | ¹H-NMR/ESI-MS |
|---|---|---|
| Example-7: Methyl 3-(1-(5-((2-chloro-6-fluorobenzyl)amino)pyridin-2-yl)-5-(trifluoromethyl)-1H-pyrazol-3-yl)-5-methyl-4,5-dihydroisoxazole-5-carboxylate | 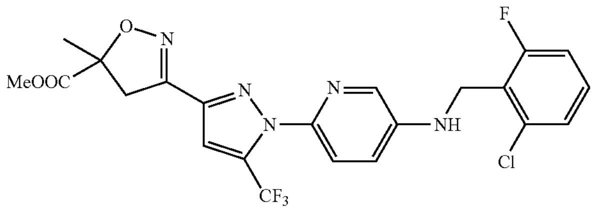 [SMILES: COC(=O)C1(C)CC(c2cc(C(F)(F)F)n(-c3ccc(NCc4c(F)cccc4Cl)cn3)n2)=NO1] | ¹HNMR (400 MHz, DMSO-$d_6$) δ 7.59 (d, J = 2.0 Hz, 1H), 7.52 (d, J = 8.0 Hz, 1H), 7.45-7.39 (m, 3H), 7.33-7.26 (m, 2H), 6.75 (t, J = 5.0 Hz, 1H, $D_2O$ exchangeable), 4.42 (d, J = 5.0 Hz, 2H), 3.85 (d, J = 17.0 Hz, 1H), 3.71 (s, 3H), 3.46 (d, J = 17.0 Hz, 1H), 1.61 (s, 3H); ESI-MS (m/z) 512, 514 [(MH)+, $Cl^{35,37}$] |

Example-8

2,6-Difluoro-N-(6-(3-(4-methyl-5-oxo-4,5-dihydro-1,3,4-oxadiazol-2-yl)-5-(trifluoromethyl)-1H-pyrazol-1-yl)pyridin-3-yl)benzamide

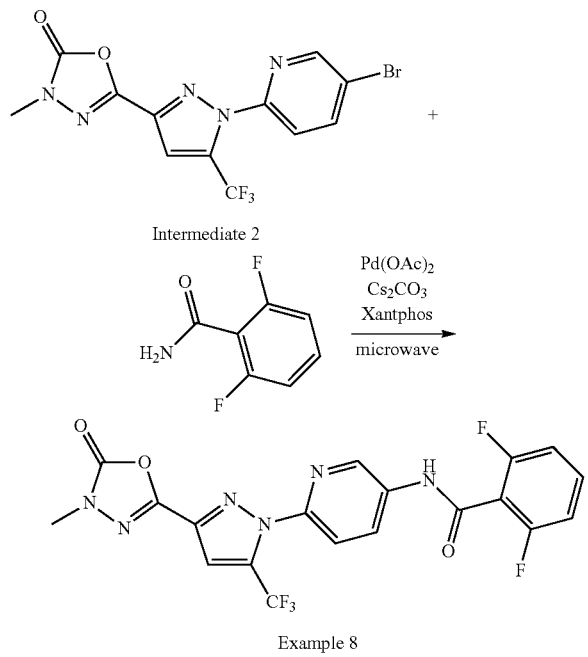

To a nitrogen purged solution of Intermediate-2 (2.0 g, 5.13 mmol) in dioxane (8 mL) in a microwave vial was added cesium carbonate (3.34 g, 10.25 mmol), 2,6-difluorobenzamide (1.05 g, 6.66 mmol) and xantphos (445 mg, 0.77 mmol) sequentially. The resulting mixture was thoroughly deoxygenated by purging nitrogen gas for 15 min and then palladium (II) acetate (115 mg, 0.513 mmol) was added to the above reaction mixture. Microwave vial was sealed and kept in microwave (Biotage) and heated to 125° C. and maintained for 1 h. The reaction mixture was cooled to room temperature and filtered through celite. The filtrate was evaporated and the crude product was purified by flash column chromatography (silica gel, 40% ethyl acetate-hexanes system as eluent) to afford 790 mg (33%) of the desired product as white solid. ¹HNMR (400 MHz, $CDCl_3$) δ 8.65 (d, J=2.5 Hz, 1H), 8.50 (dd, J=2.5 & 8.5 Hz, 1H), 7.95 (d, J=8.5 Hz, 1H), 7.90 (s, 1H, $D_2O$ exchangeable), 7.54-7.47 (m, 1H), 7.28 (s, 1H), 7.07 (t, J=8.5 Hz, 2H), 3.55 (s, 3H); ESI-MS (m/z) 467 (MH)+.

The below Examples 9 to 32 given in Table-2 were prepared by following the similar procedure as described in Example-8 by using corresponding Intermediate (Intermediate 2, 4, 5, 6, 7, 8, 9, 10, 11, 14, 15) and appropriate amine or amide Intermediate.

TABLE 2

| Example No: IUPAC name | Structure | ¹H-NMR/ESI-MS |
|---|---|---|
| Example-9: 2-Chloro-6-fluoro-N-(6-(3-(4-methyl-5-oxo-4,5-dihydro-1,3,4-oxadiazol-2-yl)-5-(trifluoromethyl)-1H-pyrazol-1-yl)pyridin-3-yl)benzamide | 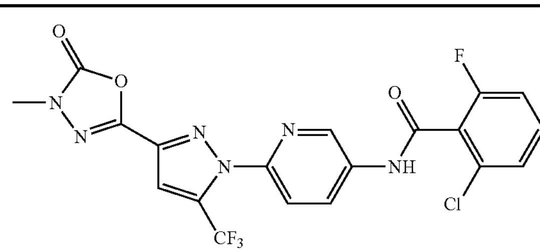 | ¹HNMR (400 MHz, $CDCl_3$) δ 8.65 (d, J = 2.5 Hz, 1H), 8.49 (dd, J = 2.5 & 8.5 Hz, 1H), 7.96 (d, J = 8.5 Hz, 1H), 7.80 (s, 1H, $D_2O$ exchangeable), 7.46-7.42 (m, 1H), 7.32 (d, J = 8.0 Hz, 1H), 7.28 (s, 1H), 7.71 (t, J = 8.0 Hz, 1H), 3.55 (s, 3H); ESI-MS (m/z) 483 (MH)+ |

TABLE 2-continued

| Example No: IUPAC name | Structure | $^1$H-NMR/ESI-MS |
|---|---|---|
| Example-10: 2-Fluoro-6-methyl-N-(6-(3-(4-methyl-5-oxo-4,5-dihydro-1,3,4-oxadiazol-2-yl)-5-(trifluoromethyl)-1H-pyrazol-1-yl)pyridin-3-yl)benzamide | 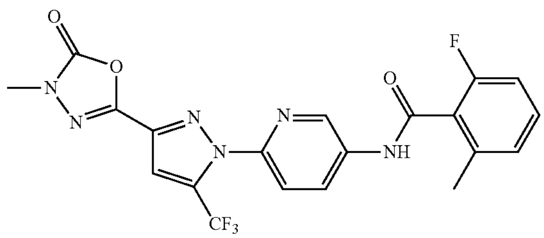 | $^1$HNMR (400 MHz, CDCl$_3$) δ 8.65 (d, J = 2.5 Hz, 1H), 8.49 (dd, J = 2.5 & 8.5 Hz, 1H), 7.94 (d, J = 8.5 Hz, 1H), 7.79 (s, 1H, D$_2$O exchangeable), 7.39-7.34 (m, 1H), 7.28 (s, 1H), 7.12 (d, J = 7.5 Hz, 1H) 7.04 (t, J = 7.5 Hz, 1H), 3.55 (s, 3H), 2.52 (s, 3H); ESI-MS (m/z) 463 (MH)$^+$ |
| Example-11: N-(6-(5-(Difluoromethyl)-3-(4-methyl-5-oxo-4,5-dihydro-1,3,4-oxadiazol-2-yl)-1H-pyrazol-1-yl)pyridin-3-yl)-2,6-difluorobenzamide | 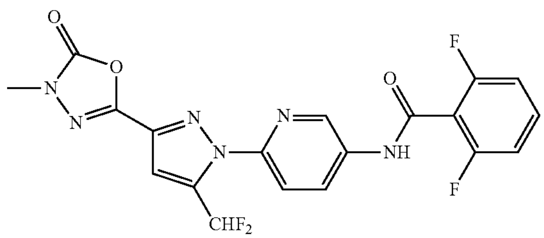 | $^1$HNMR (400 MHz, DMSO-d$_6$) δ 11.40 (s, 1H, D$_2$O exchangeable), 8.01 (d, J = 2.0 Hz, 1H), 8.03 (dd, J = 8.0 & 2.0 Hz, 1H), 8.02 (d, J = 8.0 Hz, 1H), 7.83 (t, J = 50 Hz, 1H), 7.69-7.61 (m, 1H), 7.35 (s, 1H), 7.30 (t, J = 8.0 Hz, 2H), 3.43 (s, 3H); ESI-MS (m/z) 449 (MH)$^+$ |
| Example-12: 5-(1-(5-((2,6-Difluorobenzyl)amino)pyridin-2-yl)-5-(difluoromethyl)-1H-pyrazol-3-yl)-3-methyl-1,3,4-oxadiazol-2(3H)-one | 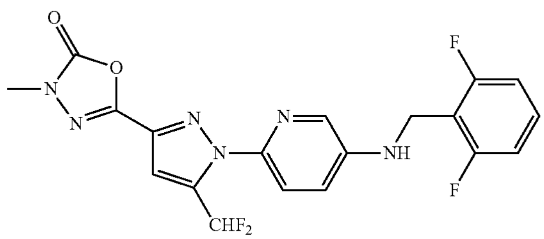 | $^1$HNMR (400 MHz, DMSO-d$_6$) δ 7.91 (d, J = 2.0 Hz, 1H), 7.70 (d, J = 8.0 Hz, 1H), 7.67 (t, J = 50 Hz, 1H), 7.48-7.41 (m, 1H), 7.30 (dd, J = 8.0 & 2.0 Hz, 1H), 7.24 (s, 1H), 7.15 (t, J = 8.0 Hz, 2H), 6.78 (t, J = 5.0 Hz, 1H, D$_2$O exchangeable), 4.38 (d, J = 5.0 Hz, 2H), 3.41 (s, 3H); ESI-MS (m/z) 435 (MH)$^+$ |
| Example-13: 5-(1-(5-((2,6-Difluorobenzyl)amino)pyridin-2-yl)-3-(difluoromethyl)-1H-pyrazol-5-yl)-3-methyl-1,3,4-oxadiazol-2(3H)-one | 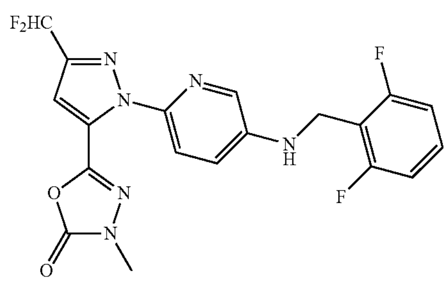 [SMILES: Cn1nc(-c2cc(C(F)F)nn2-c2ccc(NCc3c(F)cccc3F)cn2)oc1=O] | $^1$HNMR (400 MHz, CDCl$_3$) δ 7.87 (d, J = 2.0 Hz, 1H), 7.52 (d, J = 8.0 Hz, 1H), 7.32-7.25 (m, 1H), 7.19 (dd, J = 8.0 & 2.0 Hz, 1H), 7.05 (s, 1H) 6.93 (t, J = 8.0 Hz, 2H), 6.76 (t, J = 50 Hz, 1H), 4.50 (s, 2H), 3.48 (s, 3H); ESI-MS (m/z) 435 (MH)$^+$ |
| Example-14: N-(6-(3-(5,5-Dimethyl-4-oxo-4,5-dihydroisoxazol-3-yl)-5-(trifluoromethyl)-1H-pyrazol-1-yl)pyridin-3-yl)-2,6-difluorobenzamide | 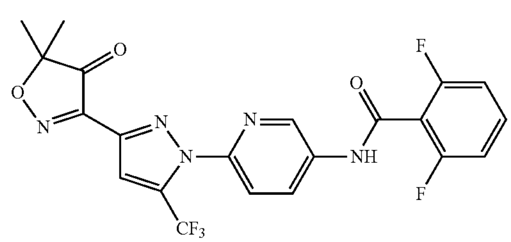 [SMILES: CC1(C)ON=C(c2cc(C(F)(F)F)n(-c3ccc(NC(=O)c4c(F)cccc4F)cn3)n2)C1=O] | $^1$HNMR (400 MHz, DMSO-d$_6$) δ 11.35 (s, 1H, D$_2$O exchangeable), 8.82 (d, J = 2.5 Hz, 1H), 8.47 (dd, J = 2.5 & 8.5 Hz, 1H), 7.94 (d, J = 8.5 Hz, 1H), 7.69-7.63 (m, 1H), 7.62 (s, 1H), 7.31 (t, J = 7.5 Hz, 2H), 1.46 (s, 6H); ESI-MS (m/z) 480 (MH)$^+$ |
| Example-15: 2-Chloro-N-(6-(3-(5,5-dimethyl-4-oxo-4,5-dihydro-isoxazol-3-yl)-5-(trifluoromethyl)-1H-pyrazol-1-yl)pyridin-3-yl)-6-fluorobenzamide | 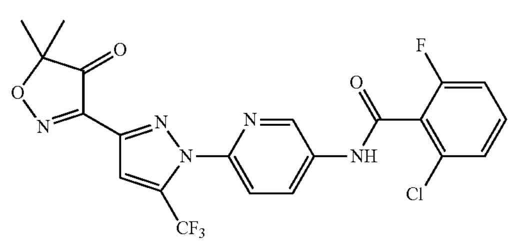 [SMILES: CC1(C)ON=C(c2cc(C(F)(F)F)n(-c3ccc(NC(=O)c4c(F)cccc4Cl)cn3)n2)C1=O] | $^1$HNMR (400 MHz, CDCl$_3$) δ 8.67 (d, J = 2.5 Hz, 1H), 8.51 (dd, J = 2.5 & 8.5 Hz, 1H), 7.97 (d, J = 8.5 Hz, 1H), 7.95 (s, 1H, D$_2$O exchangeable), 7.50 (s, 1H), 7.43-7.40 (m, 1H), 7.31 (d, J = 8.0 Hz, 1H), 7.15 (t, J = 8.0 Hz, 1H), 1.53 (s, 6H); ESI-MS (m/z) 496, 497 [(MH)$^+$, Cl$^{35,37}$] |

TABLE 2-continued

| Example No: IUPAC name | Structure | ¹H-NMR/ESI-MS |
|---|---|---|
| Example-16: 2,6-Difluoro-N-(6-(1',4',4'-trimethyl-5'-oxo-5-(trifluoromethyl)-4',5'-dihydro-1H,1'H-[3,3'-bipyrazol]-1-yl)pyridin-3-yl)benzamide | 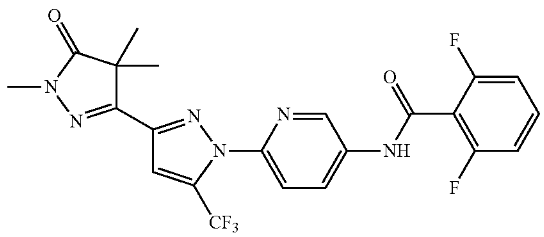 | ¹HNMR (400 MHz, DMSO-$d_6$) δ 11.36 (s, 1H, $D_2O$ exchangeable), 8.84 (d, J = 2.0 Hz, 1H), 8.41 (dd, J = 2.0 & 8.0 Hz, 1H), 7.97 (d, J = 8.0 Hz, 1H), 7.69-7.61 (m, 1H), 7.53 (s, 1H), 7.31 (t, J = 8.0 Hz, 2H) 3.34 (s, 3H), 1.45 (s, 6H); ESI-MS (m/z) 493 (MH)⁺ |
| Example-17: 2-Chloro-6-fluoro-N-(6-(1',4',4'-trimethyl-5'-oxo-5-(trifluoromethyl)-4',5'-dihydro-1H,1'H-[3,3'-bipyrazol]-1-yl)pyridin-3-yl)benzamide | 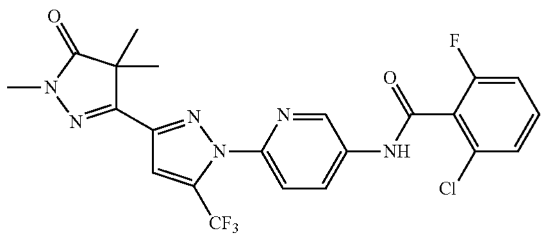 [SMILES: CN1N=C(c2cc(C(F)(F)F)n(-c3ccc(NC(=O)c4c(F)cccc4Cl)cn3)n2)C(C)(C)C1=O] | ¹HNMR (400 MHz, DMSO-$d_6$) δ 11.38 (s, 1H, $D_2O$ exchangeable), 8.83 (d, J = 2.0 Hz, 1H), 8.42 (dd, J = 2.0 & 8.0 Hz, 1H), 7.97 (d, J = 8.0 Hz, 1H), 7.64-7.58 (m, 1H), 7.53 (s, 1H), 7.51 (d, J = 8.0 Hz, 1H) 7.45 (t, J = 8.0 Hz, 1H), 3.34 (s, 3H), 1.45 (s, 6H); ESI-MS (m/z) 509 (MH)⁺ |
| Example-18: 2-Fluoro-6-methyl-N-(6-(1',4',4'-trimethyl-5'-oxo-5-(trifluoromethyl)-4',5'-dihydro-1H,1'H-[3,3'-bipyrazol]-1-yl)pyridin-3-yl)benzamide | 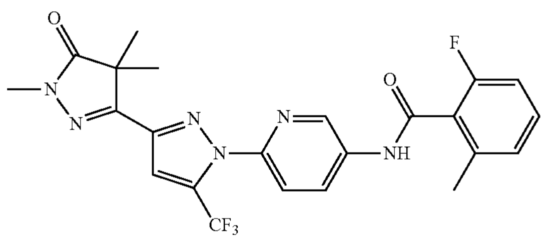 [SMILES: Cc1cccc(F)c1C(=O)Nc1ccc(-n2nc(C3=NN(C)C(=O)C3(C)C)cc2C(F)(F)F)nc1] | ¹HNMR (400 MHz, DMSO-$d_6$) δ 11.19 (s, 1H, $D_2O$ exchangeable), 8.84 (d, J = 2.0 Hz, 1H), 8.45 (dd, J = 2.0 & 8.0 Hz, 1H), 7.95 (d, J = 8.0 Hz, 1H), 7.52 (s, 1H), 7.46-7.42 (m, 1H), 7.22-7.18 (m, 2H), 3.34 (s, 3H), 2.36 (s, 3H), 1.45 (s, 6H); ESI-MS (m/z) 489 (MH)⁺ |
| Example-19: 2,6-Difluoro-N-(6-(3-(4-methyl-5-oxo-4,5-dihydro-1,2,4-oxadiazol-3-yl)-5-(trifluoromethyl)-1H-pyrazol-1-yl)pyridin-3-yl)benzamide | 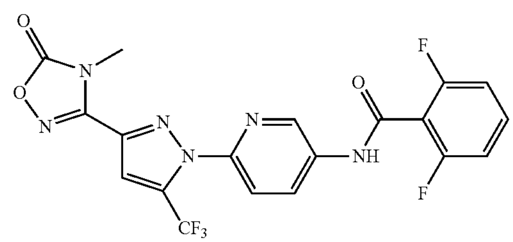 [SMILES: Cn1c(-c2cc(C(F)(F)F)n(-c3ccc(NC(=O)c4c(F)cccc4F)cn3)n2)noc1=O] | ¹HNMR (400 MHz, DMSO-$d_6$) δ 11.42 (s, 1H, $D_2O$ exchangeable), 8.85 (d, J = 2.0 Hz, 1H), 8.45 (dd, J = 2.0 & 8.0 Hz, 1H), 8.01 (d, J = 8.0 Hz, 1H), 7.81 (s, 1H), 7.70-7.62 (m, 1H), 7.32 (t, J = 8.0 Hz, 2H), 3.52 (s, 3H); ESI-MS (m/z) 467 (MH)⁺ |
| Example-20: N-(6-(3-(4-Acetyl-5,5-dimethyl-4,5-dihydro-1,3,4-oxadiazol-2-yl)-5-(trifluoromethyl)-1H-pyrazol-1-yl)pyridin-3-yl)-2,6-difluorobenzamide | 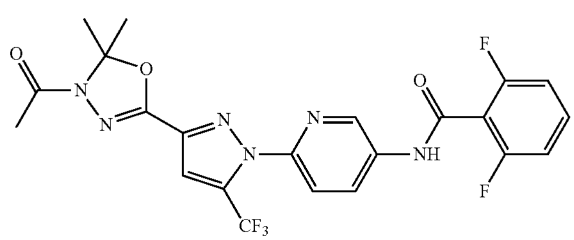 [SMILES: CC(=O)N1N=C(c2cc(C(F)(F)F)n(-c3ccc(NC(=O)c4c(F)cccc4F)cn3)n2)OC1(C)C] | ¹HNMR (400 MHz, CDCl₃) δ 8.63 (d, J = 2.0 Hz, 1H), 8.53 (dd, J = 2.0 & 8.0 Hz, 1H), 8.13 (s, 1H, $D_2O$ exchangeable), 7.90 (d, J = 8.0 Hz, 1H), 7.53-7.46 (m, 1H), 7.29 (s, 1H), 7.06 (t, J = 8.0 Hz, 2H), 2.31 (s, 3H), 1.91 (s, 6H); ESI-MS (m/z) 509 (MH)⁺ |
| Example-21: N-(6-(3-(4,4-Dimethyl-4,5-dihydrooxazol-2-yl)-5-(trifluoromethyl)-1H-pyrazol-1-yl)pyridin-3-yl)-2,6-difluorobenzamide | 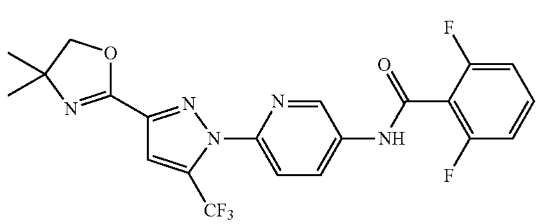 [SMILES: CC1(C)COC(c2cc(C(F)(F)F)n(-c3ccc(NC(=O)c4c(F)cccc4F)cn3)n2)=N1] | ¹HNMR (400 MHz, DMSO-$d_6$) δ 11.39 (s, 1H, $D_2O$ exchangeable), 8.78 (d, J = 2.0 Hz, 1H), 8.46 (dd, J = 2.0 & 8.0 Hz, 1H), 7.93 (d, J = 8.0 Hz, 1H), 7.68-7.63 (m, 1H), 7.54 (s, 1H), 7.31 (t, J = 8.0 Hz, 2H), 4.15 (s, 2H), 1.31 (s, 6H); ESI-MS (m/z) 466 (MH)⁺ |

TABLE 2-continued

| Example No: IUPAC name | Structure | ¹H-NMR/ESI-MS |
|---|---|---|
| Example-22: 5-(1-(5-((2,6-Difluorobenzyl)amino)pyridin-2-yl)-5-(trifluoromethyl)-1H-pyrazol-3-yl)-3-methyl-1,3,4-oxadiazol-2(3H)-one | 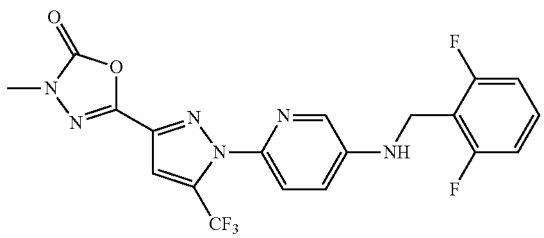 [SMILES: Cn1nc(-c2cc(C(F)(F)F)n(-c3ccc(NCc4c(F)cccc4F)cn3)n2)oc1=O] | ¹HNMR (400 MHz, CDCl₃) δ 7.97 (d, J = 2.5 Hz, 1H), 7.58 (d, J = 8.5 Hz, 1H), 7.31-7.26 (m, 1H), 7.21-7.18 (m, 2H), 6.94 (t, J = 8.0 Hz, 2H), 4.51 (s, 2H), 3.53 (s, 3H); ESI-MS (m/z) 453 (MH)⁺ |
| Example-23: 5-(1-(5-((2-Chloro-6-fluorobenzyl)amino)pyridin-2-yl)-5-(trifluoromethyl)-1H-pyrazol-3-yl)-3-methyl-1,3,4-oxadiazol-2(3H)-one | 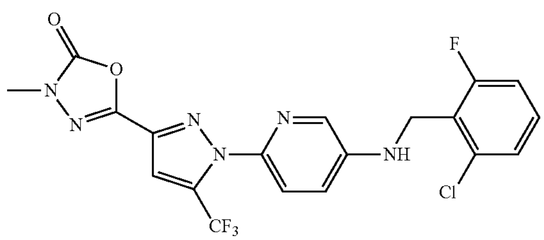 [SMILES: Cn1nc(-c2cc(C(F)(F)F)n(-c3ccc(NCc4c(F)cccc4Cl)cn3)n2)oc1=O] | ¹HNMR (400 MHz, CDCl₃) δ 7.97 (d, J = 2.5 Hz, 1H), 7.58 (d, J = 8.5 Hz, 1H), 7.30-7.20 (m, 5H), 7.08-7.06 (m, 1H), 4.58 (s, 2H), 3.53 (s, 3H); ESI-MS (m/z) 469, 471 [(MH)⁺, Cl³⁵,³⁷] |
| Example-24: 1'-(5-((2,6-Difluorobenzyl)amino)pyridin-2-yl)-1,4,4-trimethyl-5'-(trifluoromethyl)-1H,1'H-[3,3'-bipyrazol]-5(4H)-one | 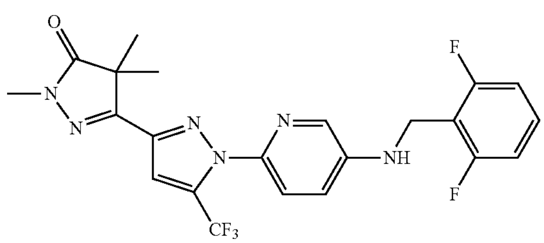 [SMILES: CN1N=C(c2cc(C(F)(F)F)n(-c3ccc(NCc4c(F)cccc4F)cn3)n2)C(C)(C)C1=O] | ¹HNMR (400 MHz, DMSO-d₆) δ 7.92 (d, J = 2.5 Hz, 1H), 7.56 (d, J = 8.5 Hz, 1H), 7.47-7.42 (m, 1H), 7.41 (s, 1H), 7.28 (dd, J = 2.5 & 8.5 Hz, 1H), 7.16 (t, J = 8.0 Hz, 2H), 6.83 (t, J = 5.5 Hz, 1H, D₂O exchangeable), 4.38 (d, J = 5.5 Hz, 2H), 3.33 (s, 3H), 1.41 (s, 6H); ESI-MS (m/z) 479 (MH)⁺ |
| Example-25: 1'-(5-((2-Chloro-6-fluorobenzyl)amino)pyridin-2-yl)-1,4,4-trimethyl-5'-(trifluoromethyl)-1H,1'H-[3,3'-bipyrazol]-5(4H)-one | 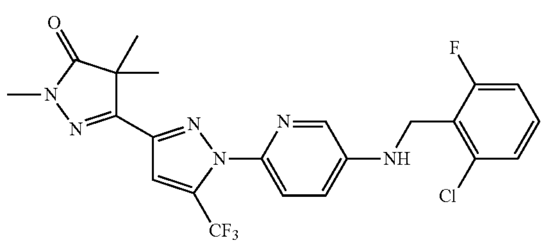 [SMILES: CN1N=C(c2cc(C(F)(F)F)n(-c3ccc(NCc4c(F)cccc4Cl)cn3)n2)C(C)(C)C1=O] | ¹HNMR (400 MHz, DMSO-d₆) δ 7.95 (d, J = 2.5 Hz, 1H), 7.57 (d, J = 8.5 Hz, 1H), 7.48-7.39 (m, 2H), 7.41 (s, 1H), 7.33-7.28 (m, 2H), 6.74 (t, J = 5.0 Hz, 1H, D₂O exchangeable), 4.42 (d, J = 5.0 Hz, 2H), 3.33 (s, 3H), 1.41 (s, 6H); ESI-MS (m/z) 495, 497 [(MH)⁺, Cl³⁵,³⁷] |
| Example-26: 3-(1-(5-((2,6-Difluorobenzyl)amino)pyridin-2-yl)-5-(trifluoromethyl)-1H-pyrazol-3-yl)-4-methyl-1,2,4-oxadiazol-5(4H)-one | 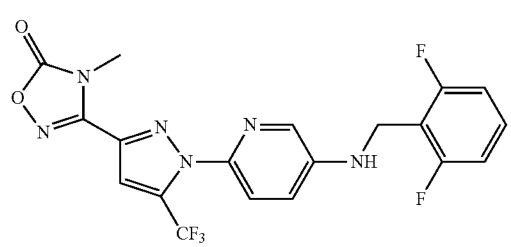 [SMILES: Cn1c(-c2cc(C(F)(F)F)n(-c3ccc(NCc4c(F)cccc4F)cn3)n2)noc1=O] | ¹HNMR (400 MHz, DMSO-d₆) δ 7.96 (d, J = 2.0 Hz, 1H), 7.69 (s, 1H), 7.63 (d, J = 8.0 Hz, 1H), 7.47-7.41 (m, 1H), 7.28 (dd, J = 2.0 & 8.0 Hz, 1H), 7.16 (t, J = 8.0 Hz, 2H), 6.92 (t, J = 5.0 Hz, 1H, D₂O exchangeable), 4.39 (d, J = 5.0 Hz, 2H), 3.47 (s, 3H); ESI-MS (m/z) 453 (MH)⁺ |
| Example-27: 1-(5-(1-(5-((2,6-Difluorobenzyl)amino)pyridin-2-yl)-5-(trifluoromethyl)-1H-pyrazol-3-yl)-2,2-dimethyl-1,3,4-oxadiazol-3(2H)-yl)ethanone | 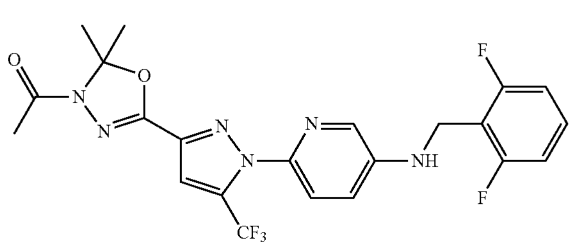 [SMILES: CC(=O)N1N=C(c2cc(C(F)(F)F)n(-c3ccc(NCc4c(F)cccc4F)cn3)n2)OC1(C)C] | ¹HNMR (400 MHz, CDCl₃) δ 7.96 (d, J = 2.0 Hz, 1H), 7.53 (d, J = 8.0 Hz, 1H), 7.32-7.28 (m, 1H), 7.21 (s, 1H), 7.17 (dd, J = 2.0 & 8.0 Hz, 1H), 6.94 (t, J = 8.0 Hz, 2H), 4.51 (s, 2H), 2.31 (s, 3H), 1.89 (s, 6H); ESI-MS (m/z) 495 (MH)⁺ |

TABLE 2-continued

| Example No: IUPAC name | Structure | ¹H-NMR/ESI-MS |
|---|---|---|
| Example-28: N-(2,6-Difluorobenzyl)-6-(3-(4,4-dimethyl-4,5-dihydrooxazol-2-yl)-5-(trifluoromethyl)-1H-pyrazol-1-yl)pyridin-3-amine | 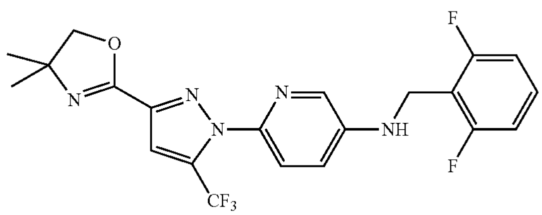 [SMILES: CC1(C)COC(c2cc(C(F)(F)F)n(-c3ccc(NCc4c(F)cccc4F)cn3)n2)=N1] | ¹HNMR (400 MHz, DMSO-d$_6$) δ 7.93 (d, J = 2.0 Hz, 1H), 7.52 (d, J = 8.0 Hz, 1H), 7.50-7.43 (m, 1H), 7.41 (s, 1H), 7.26 (dd, J = 2.0 & 8.0 Hz, 1H), 7.16 (t, J = 8.0 Hz, 2H), 6.82 (t, J = 5.0 Hz, 1H, D$_2$O exchangeable), 4.38 (d, J = 5.0 Hz, 2H), 4.12 (s, 2H), 1.29 (s, 6H); ESI-MS (m/z) 452 (MH)$^+$ |
| Example-29: N-(6-(5-Cyclopropyl-3-(4-methyl-5-oxo-4,5-dihydro-1,3,4-oxadiazol-2-yl)-1H-pyrazol-1-yl)pyridin-3-yl)-2,6-difluorobenzamide | 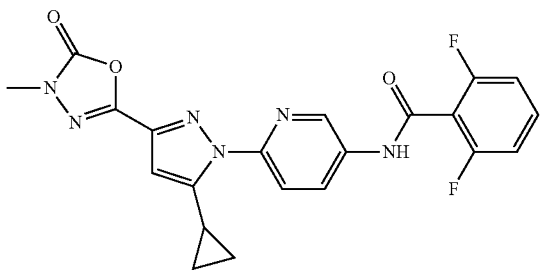 [SMILES: Cn1nc(-c2cc(C3CC3)n(-c3ccc(NC(=O)c4c(F)cccc4F)cn3)n2)oc1=O] | ¹HNMR (400 MHz, DMSO-d$_6$) δ 11.32 (s, 1H, D$_2$O exchangeable), 8.83 (d, J = 2.0 Hz, 1H), 8.40 (dd, J = 2.0 & 8.0 Hz, 1H), 7.86 (d, J = 8.0 Hz, 1H), 7.67-7.63 (m, 1H), 7.31 (t, J = 8.0 Hz, 2H), 6.64 (s, 1H), 3.41 (s, 3H), 2.67-2.59 (m, 1H), 1.02-0.97 (m, 2H), 0.82-0.77 (m, 2H); ESI-MS (m/z) 439 (MH)$^+$ |
| Example-30: N-(6-(3-Cyclopropyl 5-(4-methyl-5-oxo-4,5-dihydro-1,3,4-oxadiazol-2-yl)-1H-pyrazol-1-yl)pyridin-3-yl)-2,6-difluorobenzamide | 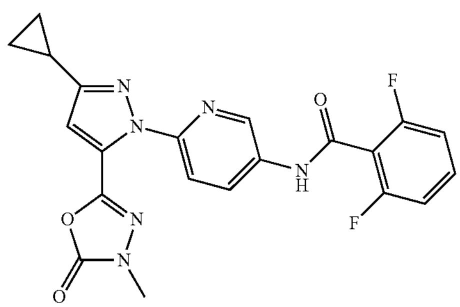 [SMILES: Cn1nc(-c2cc(C3CC3)nn2-c2ccc(NC(=O)c3c(F)cccc3F)cn2)oc1=O] | ¹HNMR (400 MHz, DMSO-d$_6$) δ 11.25 (s, 1H, D$_2$O exchangeable), 8.65 (d, J = 2.0 Hz, 1H), 8.32 (dd, J = 2.0 & 8.0 Hz, 1H), 7.84 (d, J = 8.0 Hz, 1H), 7.67-7.60 (m, 1H), 7.29 (t, J = 8.0 Hz, 2H), 6.84 (s, 1H), 3.39 (s, 3H), 2.07-1.98 (m, 1H), 1.01-0.96 (m, 2H), 0.83-0.79 (m, 2H); ESI-MS (m/z) 439 (MH)$^+$ |
| Example-31: 2,6-Difluoro-N-(6-(5-methyl-3-(4-methyl-5-oxo-4,5-dihydro-1,3,4-oxadiazol-2-yl)-1H-pyrazol-1-yl)pyridin-3-yl)benzamide | 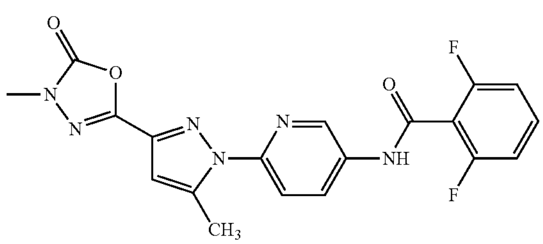 [SMILES: Cc1cc(-c2nn(C)c(=O)o2)nn1-c1ccc(NC(=O)c2c(F)cccc2F)cn1] | ¹HNMR (400 MHz, DMSO-d$_6$) δ 11.29 (s, 1H, D$_2$O exchangeable), 8.80 (d, J = 2.0 Hz, 1H), 8.39 (dd, J = 2.0 & 8.0 Hz, 1H), 7.90 (d, J = 8.0 Hz, 1H), 7.68-7.6 (m, 1H), 7.30 (t, J = 8.0 Hz, 2H), 6.81 (s, 1H), 3.41 (s, 3H), 2.62 (s, 3H); ESI-MS (m/z) 413 (MH)$^+$ |
| Example-32: 5-(1-(5-((2,6-Difluorobenzyl)amino)pyridin-2-yl)-5-methyl-1H-pyrazol-3-yl)-3-methyl-1,3,4-oxadiazol-2(3H)-one | 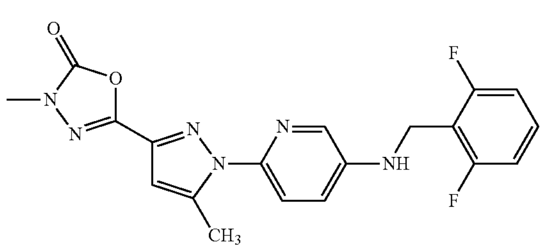 | ¹HNMR (400 MHz, CDCl$_3$) 7.93 (d, J = 2.0 Hz, 1H), 7.65 (d, J = 8.0 Hz, 1H), 7.31-7.23 (m, 1H), 7.19 (dd, J = 2.0 & 8.0 Hz, 1H), 6.93 (t, J = 8.0 Hz, 2H), 6.56 (s, 1H), 4.51 (d, J = 6.0 Hz, 2H), 4.31 (t, J = 6.0 Hz, 1H, D$_2$O exchangeable), 3.50 (s, 3H), 2.58 (s, 3H); ESI-MS (m/z) 399 (MH)$^+$ |

Example-33

(3-(1-(5-((2,6-Difluorobenzyl)amino)pyridin-2-yl)-5-(trifluoromethyl)-1H-pyrazol-3-yl)-5-methyl-4,5-dihydroisoxazol-5-yl)methanol

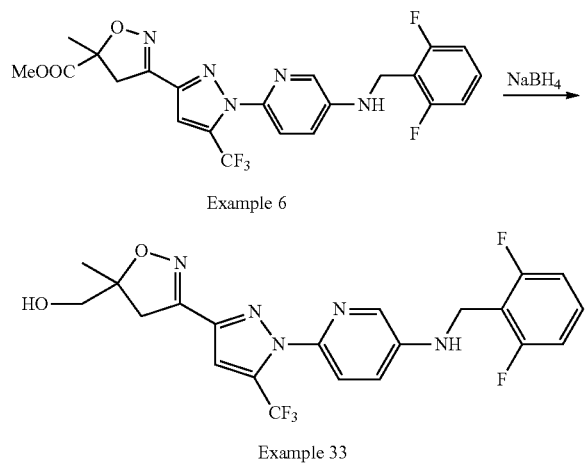

To a stirred and cooled (0° C.) solution of Example-6 (30 mg, 0.061 mmol) in methanol (3 mL) was added NaBH$_4$ (5 mg, 0.121 mmol). The resulting mixture was warmed to room temperature and then stirred for 3 h at the same temperature. Reaction was then diluted with water (3 mL) followed by ethyl acetate (5 mL). The layers were separated and the aqueous layer was extracted with ethyl acetate (2×5 mL). The combined organic layers were washed with brine (3 mL), dried (Na$_2$SO$_4$) and filtered. The filtrate was rotary evaporated and the crude product was purified by flash column chromatography (silica gel, ethyl acetate-hexanes system as eluent) to afford 20 mg (70%) of the title compound as white solid. $^1$HNMR (400 MHz, DMSO-d$_6$) δ 7.93 (d, J=2.0 Hz, 1H), 7.51 (d, J=8.0 Hz, 1H), 7.49-7.45 (m, 1H), 7.35 (s, 1H), 7.24 (dd, J=2.0 & 8.0 Hz, 1H), 7.18 (t, J=8.0 Hz, 2H), 6.82 (t, J=8.0 Hz, 1H), 5.14 (t, J=5.0 Hz, 1H), 4.38 (d, J=5.0 Hz, 2H), 3.86-3.47 (m, 3H), 3.05 (d, J=17.0 Hz, 1H), 1.32 (s, 3H); ESI-MS (m/z) 468 (MH)$^+$

Example-34

(3-(1-(5-((2-Chloro-6-fluorobenzyl)amino)pyridin-2-yl)-5-(trifluoromethyl)-1H-pyrazol-3-yl)-5-methyl-4,5-dihydroisoxazol-5-yl)methanol

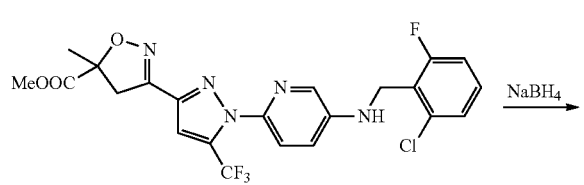

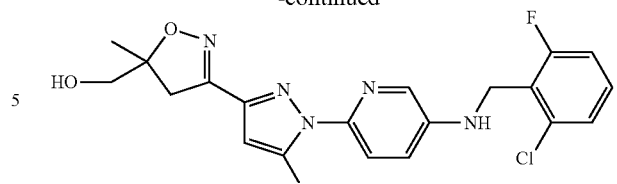

The title compound was prepared by following the similar procedure as described in Example-33 using Example-7. $^1$HNMR (400 MHz, CDCl$_3$) δ 7.99 (d, J=2.0 Hz, 1H), 7.46 (d, J=8.0 Hz, 1H), 7.30-7.23 (m, 2H), 7.21 (s, 1H), 7.18 (dd, J=8.0 & 2.0 Hz, 1H), 7.07-7.02 (m, 1H), 4.57 (s, 2H), 3.75 (d, J=12.0 Hz, 1H), 3.60 (d, J=12.0 Hz, 1H), 3.56 (d, J=17.0 Hz, 1H), 3.16 (d, J=17.0 Hz, 1H), 1.44 (s, 3H); ESI-MS (m/z) 485, 487 [(MH)$^+$, Cl$^{35,37}$]

Example-35

Methyl 3-(1-(5-(2,6-difluorobenzamido)pyridin-2-yl)-5-(trifluoromethyl)-1H-pyrazol-3-yl)-5-methyl-4,5-dihydroisoxazole-5-carboxylate

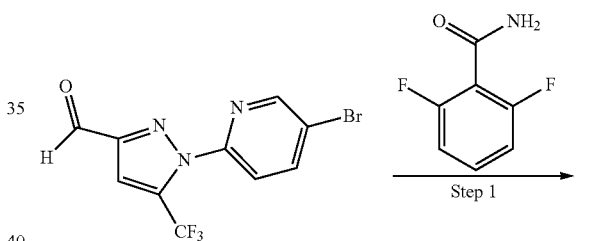

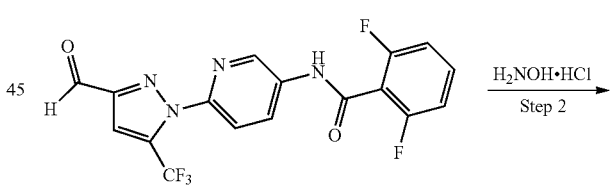

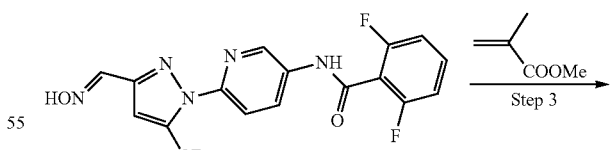

Step-1: 2,6-Difluoro-N-(6-(3-formyl-5-(trifluoromethyl)-1H-pyrazol-1-yl)pyridin-3-yl) benzamide: In a sealed tube containing a dioxane (20 mL) and cesium carbonate (2.54 g, 7.81 mmol) was purged with nitrogen gas for 10 min and then 1-(5-bromopyridin-2-yl)-5-(trifluoromethyl)-1H-pyrazole-3-carbaldehyde (prepared in step-1 of the intermediate-12; 1.0 g, 3.12 mmol), 2,6-difluorobenzamide (736 mg, 4.69 mmol) and xanthphos (180 mg, 0.31 mmol) were sequentially added. The resulting mixture was thoroughly deoxygenated by purging nitrogen gas for another 15 min and then palladium (II) acetate (35 mg, 0.15 mmol) was added to the above mixture. The sealed tube was capped and stirred at 130° C. for 6 h. The reaction mixture was then cooled to room temperature and filtered through celite. The filtrate was rotary evaporated and the crude product was purified by flash column chromatography (silica gel, ethyl acetate-hexanes system as eluent) to afford 700 mg (56%) of the title compound as white solid. $^1$HNMR (400 MHz, CDCl$_3$) δ 10.09 (s, 1H), 8.63 (d, J=2.0 Hz, 1H), 8.60 (dd, J=2.0 & 8.0 Hz, 1H), 8.00 (brs, 1H, D$_2$O Exchangeable), 7.93 (d, J=8.0 Hz, 1H), 7.59-7.53 (m, 1H), 7.36 (s, 1H), 7.09 (t, J=8.0 Hz, 2H); ESI-MS (m/z) 397 (MH)$^+$ Step-2: 2,6-Difluoro-N-(6-(3-((hydroxyimino)methyl)-5-(trifluoromethyl)-1H-pyrazol-1-yl)pyridin-3-yl)benzamide: To (0° C.) cooled solution of the above Step-1 intermediate (900 mg, 2.27 mmol) in methanol (10 mL) was added solution of hydroxylamine hydrochloride (237 mg, 3.41 mmol) in water (5 mL) followed by a solution of sodium carbonate (241 mg, 2.27 mmol) in water (2 mL). The resulting mixture was then stirred at room temperature for 2 h. The reaction was then diluted with water (20 mL) followed by ethyl acetate (50 mL). The layers were separated and the aqueous layer was extracted with ethyl acetate (2×50 mL). The combined organic layers were washed with brine (25 mL), dried (Na$_2$SO$_4$) and filtered. The filtrate was concentrated under vacuum to afford 900 mg (96%) of the desired product as white solid. ESI-MS (m/z) 412 (MH)$^+$ Step-3: Methyl 3-(1-(5-(2,6-difluorobenzamido)pyridin-2-yl)-5-(trifluoromethyl)-1H-pyrazol-3-yl)-5-methyl-4,5-dihydroisoxazole-5-carboxylate: To a stirred solution of the above Step-2 intermediate (900 mg, 2.18 mmol) in THF (25 mL) were added NCS (438 mg, 3.28 mmol) and pyridine (124 μL, 1.53 mmol) at 0° C. and then stirred at 45° C. for 2 h. The reaction was cooled to 0° C., methyl methacrylate (350 μL, 3.28 mmol) was then added to the above mixture followed by triethyl amine (610 μL, 4.38 mmol). The resulting mixture was stirred at 40° C. for 4 h. The reaction was then cooled down to room temperature and diluted with water (50 mL) followed by ethyl acetate (25 mL). The layers were separated and the aqueous layer was extracted with ethyl acetate (2×25 mL). The combined organic layers were washed with brine (20 mL), dried (Na$_2$SO$_4$) and filtered. The filtrate was rotary evaporated and the crude product was purified by flash column chromatography (silica gel, ethyl acetate-hexanes system as eluent) to afford 660 mg, (59%) of the title compound as white solid. $^1$HNMR (400 MHz, DMSO) δ 11.37 (s, 1H, D$_2$O exchangeable), 8.79 (d, J=2.0 Hz, 1H), 8.44 (dd, J=2.0 & 8.0 Hz, 1H), 7.92 (d, J=8.0 Hz, 1H), 7.69-7.62 (m, 1H), 7.56 (s, 1H), 7.33 (t, J=8.0 Hz, 2H), 3.90 (d, J=17.0 Hz, 1H), 3.72 (s, 3H), 3.51 (d, J=17.0 Hz, 1H), 1.62 (s, 3H). ESI-MS (m/z) 510 (MH)$^+$ Example-36

2,6-Difluoro-N-(6-(3-(5-(hydroxymethyl)-5-methyl-4,5-dihydroisoxazol-3-yl)-5-(trifluoromethyl)-1H-pyrazol-1-yl)pyridin-3-yl)benzamide

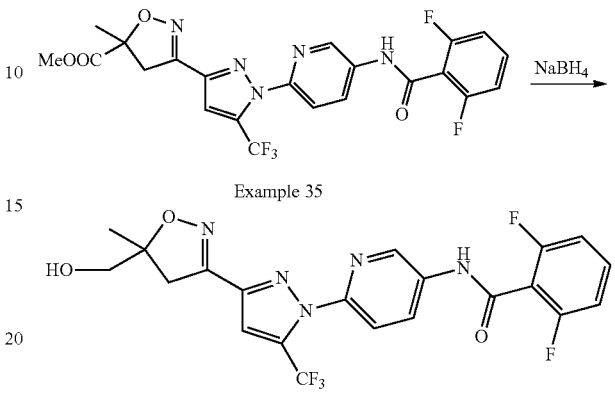

Example 35

Example 36

The title compound was prepared from Example-35 by following the similar procedure as described in Example-33. $^1$HNMR (400 MHz, CDCl$_3$) δ 8.56 (m, 1H), 8.54 (d, J=2.0 Hz, 1H), 7.85-7.83 (m, 2H), 7.54-7.47 (m, 1H), 7.29 (s, 1H), 7.07 (t, J=8.0 Hz, 2H), 3.79 (d, J=12.0 Hz, 1H), 3.36 (d, J=12.0 Hz, 1H), 3.61 (d, J=17.0 Hz, 1H), 3.20 (d, J=17.0 Hz, 1H), 1.47 (s, 3H); ESI-MS (m/z) 482 (MH)$^+$ Example-37

3-(1-(5-(2,6-Difluorobenzamido)pyridin-2-yl)-5-(trifluoromethyl)-1H-pyrazol-3-yl)-5-methyl-4,5-dihydroisoxazole-5-carboxamide

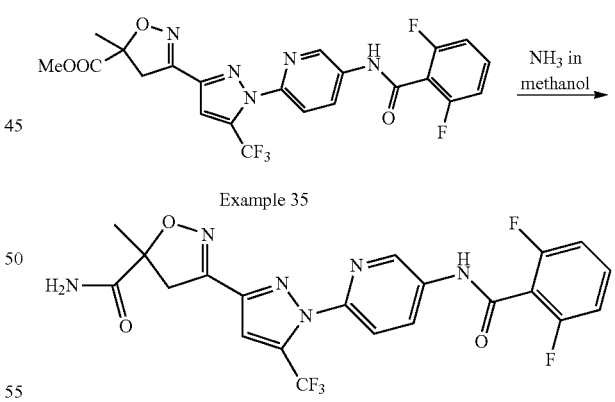

Example 35

Example 37

To a solution of from Example-35 (100 mg, 0.19 mmol) in methanol was added a solution of ammonia in methanol (5 mL) and the resulting solution was heated to 100° C. and further maintained for 16 h. The reaction was cooled to room temperature and the solvent was evaporated under reduced pressure. The crude product was triturated with 10% ethyl acetate in hexane (10 mL) to afford 50 mg (50%) of the title compound as white solid. $^1$HNMR (400 MHz, DMSO-d$_6$) δ 11.00 (s, 1H), 8.00 (d, J=2.0 Hz, 1H), 8.44-8.41 (dd, J=2.0 &

8.0 Hz, 1H), 7.94 (d, J=8.0 Hz, 1H), 7.69-7.65 (m, 1H), 7.64 (brs, 1H, D₂O exchangeable), 7.54 (s, 1H), 7.44 (brs, 1H, D₂O exchangeable), 7.33-7.29 (t, J=8.0 Hz, 2H), 3.81 (d, J=17.0 Hz, 1H), 3.37 (d, J=17.0 Hz, 1H), 1.58 (s, 3H); ESI-MS (m/z) 495 (MH)⁺

Example-38

2,6-Difluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide

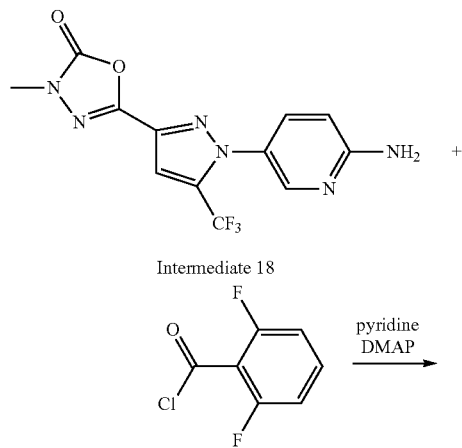

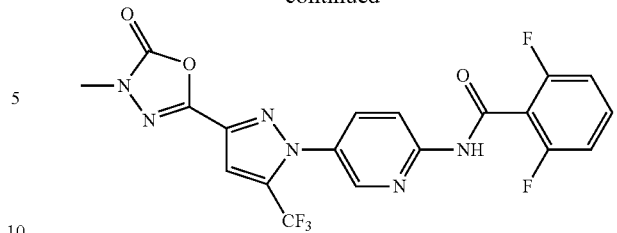

Example 38

To a stirred solution of Intermediate-18 (75 mg, 0.230 mmol) in DCM (2 mL) was added 2,6-difluorobenzoyl chloride (29 µL, 0.230 mmol), pyridine (37 µL, 0.460 mmol) followed by DMAP (5.62 mg, 0.046 mmol). After stirring the above reaction mixture at room temperature for 16 h, the reaction was diluted with DCM (10 mL), washed with aqueous hydrochloric acid (10%, 10 mL) brine (10 mL), dried (Na₂SO₄) and filtered. The filtrate was evaporated and the crude product was purified by flash column chromatography to afford 25 mg (20%) of the desired product as white solid. ¹HNMR (400 MHz, DMSO-d₆) δ 11.80 (s, 1H, D₂O exchangeable), 8.66 (d, J=2.5 Hz, 1H), 8.40 (d, J=8.5 Hz, 1H), 8.20 (dd, J=2.5 & 8.5 Hz, 1H), 7.77 (s, 1H), 7.65-7.57 (m, 1H), 7.25 (t, J=8.5 Hz, 2H), 3.43 (s, 3H); ESI-MS (m/z) 467 (MH)⁺.

The below Examples 39 to 50 given in Table-3 were prepared by following the similar procedure as described in Example-38 by using Intermediate-18 and appropriate acid chloride.

TABLE 3

| Example-No: IUPAC name | Structure | ¹HNMR/ESI-MS |
|---|---|---|
| Example-39: 2-Chloro-6-fluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide | | ¹HNMR (400 MHz, DMSO-d₆) δ 11.82 (s, 1H, D₂O exchangeable), 8.66 (d, J = 2.5 Hz, 1H), 8.42 (d, J = 8.5 Hz, 1H), 8.20 (dd, J = 2.5 & 8.5 Hz, 1H), 7.78 (s, 1H), 7.59-7.54 (m, 1H), 7.45 (d, J = 7.5 Hz, 1H), 7.39 (t, J = 7.5 Hz, 1H), 3.43 (s, 3H); ESI-MS (m/z) 483, 485 [(MH)⁺, Cl³⁵,³⁷]. |
| Example-40: 2-Fluoro-6-methyl-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide | 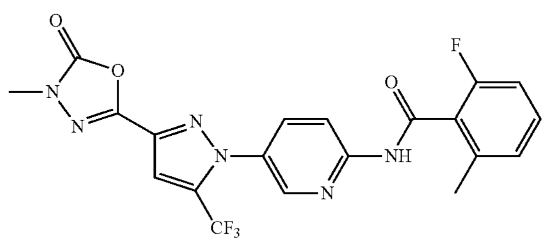 | ¹HNMR (400 MHz, DMSO-d₆) δ 10.63 (s, 1H, D₂O exchangeable), 9.13 (d, J = 2.5 Hz, 1H), 8.65 (dd, J = 2.5 & 8.5 Hz, 1H), 8.15 (d, J = 8.5 Hz, 1H), 7.82 (s, 1H), 7.50-7.42 (m, 3H), 3.45 (s, 3H); ESI-MS (m/z) 483 (MH)⁺. |
| Example-41: 2-Fluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide | 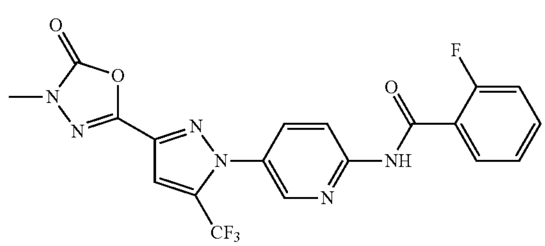 | ¹HNMR (400 MHz, DMSO-d₆) δ 11.32 (s, 1H, D₂O exchangeable), 8.66 (d, J = 2.0 Hz, 1H), 8.42 (d, J = 8.0 Hz, 1H), 8.19 (dd, J = 2.0 & 8.0 Hz, 1H), 7.78 (s, 1H), 7.76-7.72 (m, 1H), 7.65-7.59 (m, 1H), 7.39-7.32 (m, 2H), 3.43 (s, 3H); ESI-MS (m/z) 449 (MH)⁺ |

TABLE 3-continued

| Example-No: IUPAC name | Structure | $^1$HNMR/ESI-MS |
|---|---|---|
| Example-42: 2,3-Difluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide | 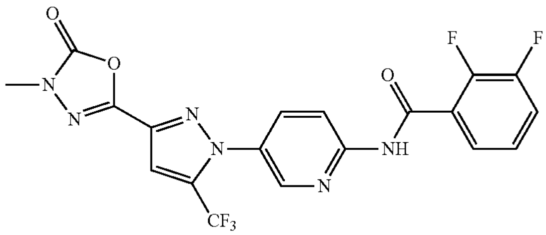 [SMILES: Cn1nc(-c2cc(C(F)(F)F)n(-c3ccc(NC(=O)c4cccc(F)c4F)nc3)n2)oc1=O] | $^1$HNMR (400 MHz, CDCl$_3$) δ 9.19 (d, J = 12.0 Hz, 1H), 8.61 (d, J = 12.0 Hz, 1H), 8.54 (d, J = 2.0 Hz, 1H), 7.96-7.92 (m, 2H), 7.46-7.43 (m, 1H), 7.33-7.28 (m, 2H), 3.55 (s, 3H); ESI-MS (m/z) 467 (MH)$^+$ |
| Example-43: 2,4,5-Trifluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide | 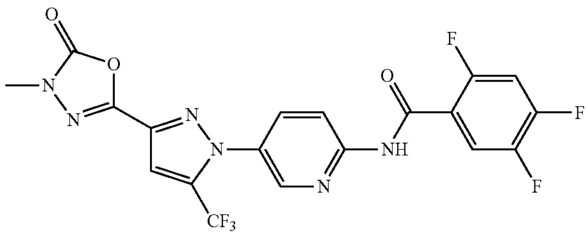 [SMILES: Cn1nc(-c2cc(C(F)(F)F)n(-c3ccc(NC(=O)c4cc(F)c(F)cc4F)nc3)n2)oc1=O] | $^1$HNMR (400 MHz, DMSO-d$_6$) δ 11.45 (s, 1H, D$_2$O exchangeable), 8.67 (d, J = 2.0 Hz, 1H), 8.39 (d, J = 8.0 Hz, 1H), 8.20 (dd, J = 2.0 & 8.0 Hz, 1H), 7.95-7.89 (m, 1H), 7.80-7.73 (m, 1H), 7.78 (s, 1H) 3.43 (s, 3H); ESI-MS (m/z) 485 (MH)$^+$ |
| Example-44: 2,3,4-Trifluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide | 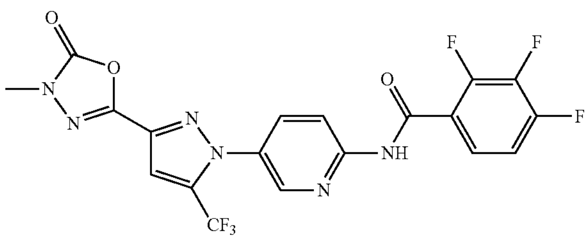 [SMILES: Cn1nc(-c2cc(C(F)(F)F)n(-c3ccc(NC(=O)c4ccc(F)c(F)c4F)nc3)n2)oc1=O] | $^1$HNMR (400 MHz, DMSO-d$_6$) δ 11.51 (s, 1H, D$_2$O exchangeable), 8.68 (d, J = 2.0 Hz, 1H), 8.39 (d, J = 8.0 Hz, 1H), 8.20 (dd, J = 2.0 & 8.0 Hz, 1H), 7.79 (s, 1H), 7.67-7.60 (m, 1H), 7.52-7.42 (m, 1H), 3.43 (s, 3H); ESI-MS (m/z) 485 (MH)$^+$ |
| Example-45: 2,4-Difluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide | 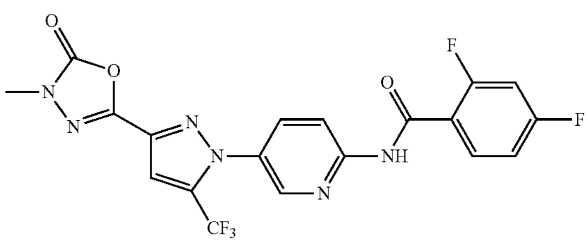 [SMILES: Cn1nc(-c2cc(C(F)(F)F)n(-c3ccc(NC(=O)c4ccc(F)cc4F)nc3)n2)oc1=O] | $^1$HNMR (400 MHz, DMSO-d$_6$) δ 11.34 (s, 1H, D$_2$O exchangeable), 8.65 (d, J = 2.0 Hz, 1H), 8.41 (d, J = 8.0 Hz, 1H), 8.18 (dd, J = 2.0 & 8.0 Hz, 1H), 7.85-7.80 (m, 1H), 7.78 (s, 1H), 7.47-7.44 (m, 1H), 7.27-7.24 (m, 1H), 3.43 (s, 3H); ESI-MS (m/z) 467 (MH)$^+$ |
| Example-46: 2,3-Dimethyl-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide | 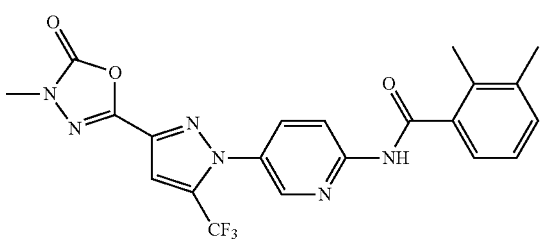 | $^1$HNMR (400 MHz, DMSO-d$_6$) δ 11.25 (s, 1H, D$_2$O exchangeable), 8.62 (d, J = 2.0 Hz, 1H), 8.44 (d, J = 8.0 Hz, 1H), 8.16 (dd, J = 2.0 & 8.0 Hz, 1H), 7.78 (s, 1H), 7.33-7.29 (m, 2H), 7.21-7.18 (m, 1H), 3.44 (s, 3H), 2.30 (s, 3H), 2.28 (s, 3H); ESI-MS (m/z) 459 (MH)$^+$ |
| Example-47: 2-Chloro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide | 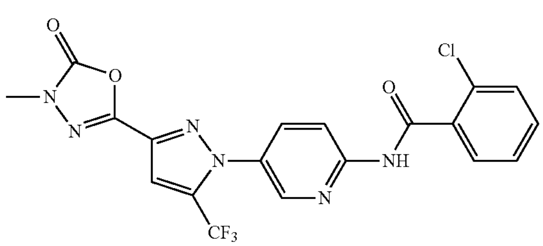 [SMILES: Cn1nc(-c2cc(C(F)(F)F)n(-c3ccc(NC(=O)c4ccccc4Cl)nc3)n2)oc1=O] | $^1$HNMR (400 MHz, DMSO-d$_6$) δ 11.50 (s, 1H, D$_2$O exchangeable), 8.64 (d, J = 2.0 Hz, 1H), 8.42 (d, J = 8.0 Hz, 1H), 8.18 (dd, J = 2.0 & 8.0 Hz, 1H), 7.78 (s, 1H), 7.65 (dd, J = 2.0 & 7.0 Hz, 1H), 7.58-7.56 (m, 1H), 7.54-7.50 (m, 1H), 7.48-7.44 (m, 1H), 3.43 (s, 3H); ESI-MS (m/z) 465, 467 [(MH)$^+$, Cl$^{35,37}$] |

TABLE 3-continued

| Example-No: IUPAC name | Structure | ¹HNMR/ESI-MS |
|---|---|---|
| Example-48: 2-Methyl-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide | | ¹HNMR (400 MHz, DMSO-$d_6$) δ 11.24 (s, 1H, $D_2O$ exchangeable), 8.64 (d, J = 2.0 Hz, 1H), 8.43 (d, J = 8.0 Hz, 1H), 8.16 (dd, J = 2.0 & 8.0 Hz, 1H), 7.77 (s, 1H), 7.53 (d, J = 8.0 Hz, 1H), 7.43-7.39 (m, 1H), 7.32-7.28 (m, 2H), 3.43 (s, 3H), 2.42 (s, 3H); ESI-MS (m/z) 445 $(MH)^+$ |
| Example-49: 4-Ethyl-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide | 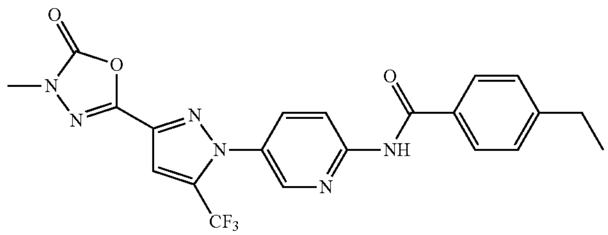 [SMILES: CCc1ccc(C(=O)Nc2ccc(-n3nc(-c4nn(C)c(=O)o4)cc3C(F)(F)F)cn2)cc1] | ¹HNMR (400 MHz, $CDCl_3$) δ 8.81 (s, 1H, $D_2O$ exchangeable), 8.62 (d, J = 8.0 Hz, 1H), 8.50 (d, J = 2.0 Hz, 1H), 7.93 (dd, J = 2.0 & 8.0 Hz, 1H), 7.89 (d, J = 8.0 Hz, 2H), 7.37 (d, J = 8.0 Hz, 2H), 7.27 (s, 1H), 3.55 (s, 3H), 2.76 (q, J = 7.0 Hz, 2H), 1.28 (t, J = 7.0 Hz, 3H); ESI-MS (m/z) 459 $(MH)^+$ |
| Example-50: N-(5-(3-(4-Methyl-5-oxo-4,5-dihydro-1,3,4-oxadiazol-2-yl)-5-(trifluoromethyl)-1H-pyrazol-1-yl)pyridin-2-yl)-2-naphthamide | 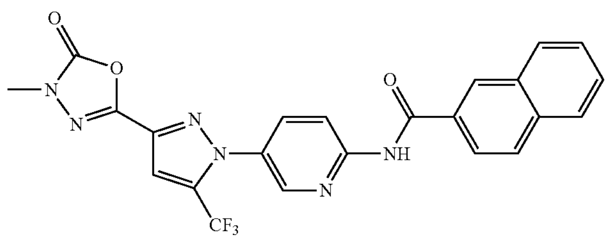 [SMILES: Cn1nc(-c2cc(C(F)(F)F)n(-c3ccc(NC(=O)c4ccc5ccccc5c4)nc3)n2)oc1=O] | ¹HNMR (400 MHz, $CDCl_3$) δ 8.96 (s, 1H, $D_2O$ exchangeable), 8.68 (d, J = 8.0 Hz, 1H), 8.55 (d, J = 2.0 Hz, 1H), 8.51-8.50 (m, 1H), 8.03-8.01 (m, 4H), 7.98-7.94 (m, 2H), 7.68-7.60 (m, 2H), 3.56 (s, 3H); ESI-MS (m/z) 481 $(MH)^+$ |

Example-51

5-(1-(6-((2,6-Difluorobenzyl)amino)pyridin-3-yl)-5-(trifluoromethyl)-1H-pyrazol-3-yl)-3-methyl-1,3,4-oxadiazol-2(3H)-one

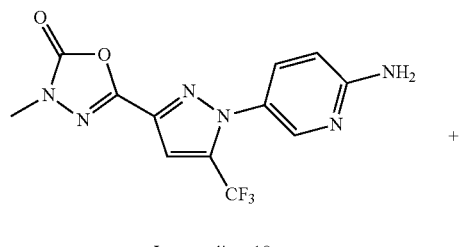

Intermediate 18

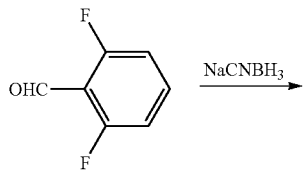

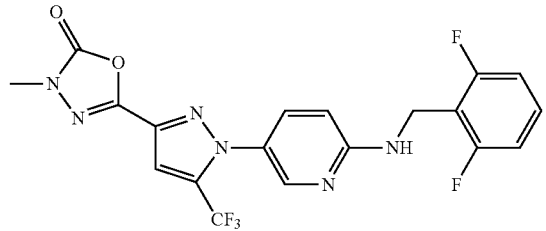

Example 51

To a stirred solution of Intermediate-18 (100 mg, 0.307 mmol) in methanol (5 mL), containing molecular sieves (100 mg), was added 2,6-difluorobenzaldehyde (97 mg, 0.61 mmol) and acetic acid (35 μL, 0.61 mmol). The reaction was stirred at room temperature for 18 h. Sodium cyanoborohydride (38.5 mg, 0.613 mmol) was then added to the above mixture. The resulting mixture was stirred at room temperature for 18 h and then filtered. The solid obtained was washed with methanol and purified by preparative HPLC to obtain 80 mg (55%) of the title compound as white solid. ¹HNMR (400 MHz, $CDCl_3$) δ 8.22 (d, J=2.5 Hz, 1H), 7.57 (dd, J=2.5 & 8.5 Hz, 1H), 7.33-7.25 (m, 1H), 7.20 (s, 1H), 6.92 (t, J=7.5 Hz, 2H), 6.63 (d, J=8.5 Hz, 1H), 5.57 (s, 1H), 4.68 (d, J=6.5 Hz, 2H), 3.53 (s, 3H) ; ESI-MS (m/z) 453 (MH)+.

Example-52

5-(1-(6-((4(2-Chloro-6-fluorobenzyl)amino)pyridin-3-yl)-5-(trifluoromethyl)-1H-pyrazol-3-yl)-3-methyl-1,3,4-oxadiazol-2(3H)-one

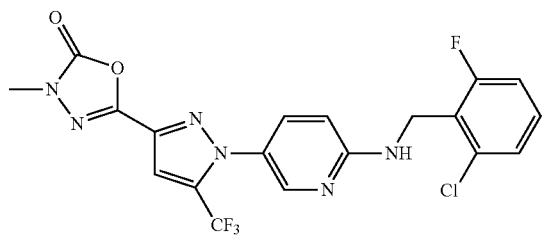

The title compound was prepared by following the similar reductive amination procedure as described in Example-51 using Intermediate-18 and 2-chloro-6-fluorobenzaldehyde. $^1$HNMR (400 MHz, DMSO-$d_6$) δ 8.20 (d, J=2.5 Hz, 1H), 7.64 (s, 1H), 7.59 (dd, J=2.5 & 8.5 Hz, 1H), 7.50-7.48 (m, 1H), 7.46-7.37 (m, 1H), 7.39 (s, 1H), 7.26-7.22 (m, 1H), 6.66 (d, J=8.5 Hz, 1H), 4.63 (s, 2H), 3.42 (s, 3H); ESI-MS (m/z) 469, 471 [(MH)+, Cl$^{35,37}$]

Example-53

5-(1-(6-((2-Fluoro-6-methylbenzyl)amino)pyridin-3-yl)-5-(trifluoromethyl)-1H-pyrazol-3-yl)-3-methyl-1,3,4-oxadiazol-2(3H)-one

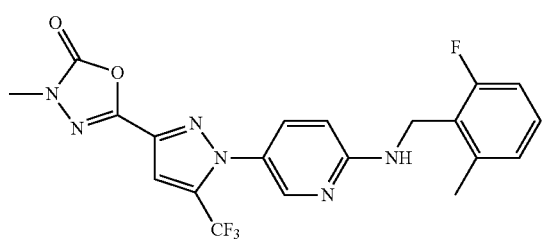

The title compound was prepared by following the similar reductive amination procedure as described in Example-51 using Intermediate-18 and 2-fluoro-6-methylbenzaldehyde. $^1$HNMR (400 MHz, CDCl$_3$) δ 8.24 (d, J=2.5 Hz, 1H), 7.50 (dd, J=2.5 & 8.5 Hz, 1H), 7.23-7.17 (m, 1H), 7.20 (s, 1H), 7.02 (d, J=7.0 Hz, 1H), 6.96 (t, J=7.0 Hz, 1H), 6.50 (d, J=8.5 Hz, 1H), 4.88 (s, 1H), 4.64 (s, 2H), 3.53 (s, 3H), 2.46 (s, 3H); ESI-MS (m/z) 449 (MH)+

Example-54

N-(2,6-Difluorophenyl)-6-(3-(4-methyl-5-oxo-4,5-dihydro-1,3,4-oxadiazol-2-yl)-5-(trifluoromethyl)-1H-pyrazol-1-yl)nicotinamide

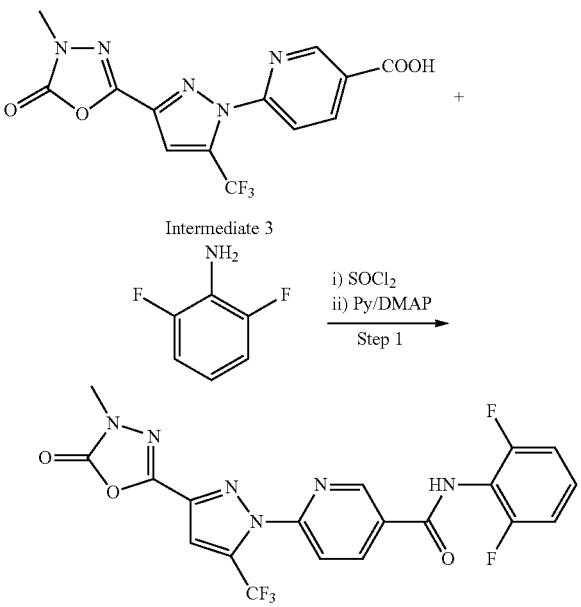

Example 54

A stirred suspension of Intermediate-3 (0.40 g, 1.12 mmol) and SOCl$_2$ (3.29 mL, 45.0 mmol) was heated to 90° C. and maintained for 4 h. Excess of SOCl$_2$ was evaporated. The residue was azeotroped with toluene and dissolved in DCM (20 mL) and 2,6-difluoroaniline (160 mg, 1.23 mmol), pyridine (0.273 mL, 3.38 mmol) and DMAP (0.014 g, 0.113 mmol) were sequentially added at 0° C. to the above solution. The reaction was then warmed to room temperature and then stirred for 18 h at the same temperature. Reaction was cooled back down to 0° C. and ice water (10 mL) was added. The separated solid was filtered and dried under vacuum to afford 70 mg (13%) of the desired product as a white solid. $^1$HNMR (400 MHz, DMSO-$d_6$) δ 10.58 (s, 1H, D$_2$O exchangeable), 9.13 (d, J=2.5 Hz, 1H), 8.65 (dd, J=2.5 & 8.5 Hz, 1H), 8.14 (d, J=8.5 Hz, 1H), 7.82 (s, 1H), 7.50-7.42 (m, 1H), 7.24 (t, J=8.0 Hz, 2H), 3.45 (s, 3H); ESI-MS (m/z) 467 (MH)+.

Example-55

N-(2-Chloro-6-fluorophenyl)-6-(3-(4-methyl-5-oxo-4,5-dihydro-1,3,4-oxadiazol-2-yl)-5-(trifluoromethyl)-1H-pyrazol-1-yl)nicotinamide

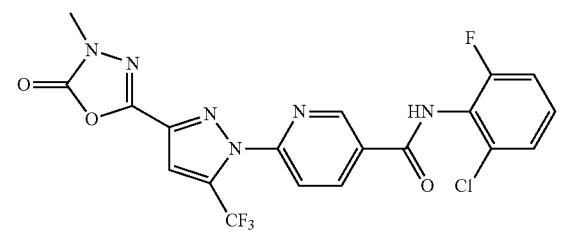 [SMILES: Cn1nc(-c2cc(C(F)(F)F)n(-c3ccc(C(=O)Nc4c(F)cccc4Cl)cn3)n2)oc1=O]

The title compound was prepared by reacting Intermediate-3 with 2-chloro-6-fluoroaniline, by following the similar procedure as described in Example-54. $^1$HNMR (400 MHz, DMSO-$d_6$) δ 10.63 (s, 1H, $D_2O$ exchangeable), 9.13 (d, J=2.5 Hz, 1H), 8.65 (dd, J=2.5 & 8.5 Hz, 1H), 8.15 (d, J=8.5 Hz, 1H), 7.82 (s, 1H), 7.50-7.42 (m, 3H), 3.45 (s, 3H); ESI-MS (m/z) 483 (MH)$^+$.

Biological Assays and Utility:

The CRAC channel modulatory activity of the compounds were thus evaluated by measuring the secretion of IL-2 by antigen stimulated T-cells in vitro. Alternatively, such activity can also be evaluated by assay methods known to one skilled in the art.

In Vitro Assay

Example-56

Inhibition of IL-2 secretion: Jurkat T cells were seeded at a density of 0.5 to 1 million cells per well in RPMI medium. Test compounds from this invention were added to the cells at different concentrations. This was followed by the addition of PHA, a T cell mitogen after 10 minutes. The cells were then incubated for 20 to 24 hours in a $CO_2$ incubator at 37° C. After incubation with the compounds, cells were centrifuged, the supernatant was collected and processed for ELISA to quantitate the amount of IL-2 secreted. A commercial ELISA kit (R&D Systems, Inc. Minneapolis, Minn., USA) was used to estimate the IL-2 concentrations. Amount of IL-2 secreted by cells stimulated with PHA was considered as a 100% maximal signal and the decrease in amount of IL-2 secreted by cells treated with the test compounds was expressed as percent inhibition of the maximal signal. The dose response data was analyzed using 4-parametric sigmoidal dose response (variable slope) curve—fit.

In the above IL-2 assay, compounds of the invention were found to have $IC_{50}$ (nM) values as shown below:

| $IC_{50}$ (nM) | Examples |
|---|---|
| <100 nM | 8, 9, 10, 11. 12, 14, 15, 18, 22, 23, 32, 33, 36, 37, 38, 39, 40, 41, 42, 43, 44, 45, 46, 47, 48 51, 52, 53, 55 |
| 100 nM-1000 nM | 1, 2, 3, 5, 6, 7, 16, 17, 19, 20, 21, 24, 25, 34, 35 26, 27, 28, 29, 30, 49, 50, 54 |
| >1000 nM | 4, 13, 31 |

Thus, compounds of the invention are shown to inhibit IL-2 secretion.

Example-57

SOCE inhibition: Jurkat E6.1 cells were seeded at a density of 1-2×10$^5$ cells per well in calcium-4 dye prepared in calcium free HBSS (Sigma, USA). Test compounds from this invention were added to the cells at different concentrations. This was followed by the addition of thapsigargin (TG), a SERCA inhibitor, to empty the stores of calcium.

Calcium chloride was added to the cells after 10-30 min to induce calcium influx and the fluorescence was measured for 10 min using the FLIPR-Tetra detection system. Fluorescence was also measured using a plate reader at 485 nm excitation and 520 nm emission (Synergy2, Biotek, USA) after 30-90 minutes of calcium addition. Fluorescence observed in cells treated with Thapsigargin and calcium chloride solution was considered 100% maximal signal and the reduced fluorescent signal observed in the presence of test compounds was expressed as percentage inhibition of the maximal signal. The dose response data was analysed using 4-parametric sigmoidal dose response (variable slope) curve—fit.

In the above SOCE inhibition assay, compounds of the present invention showed activity less than <1000 nM against SOCE. Thus, compounds of the invention are shown to have CRAC channel modulation activity by inhibition of SOCE.

Example-58

NFAT Transcriptional Activity: HEK 293 cells were stably co-transfected with a NFAT-FireflyLuciferase and Tk-Renilla Luciferase reporter genes 30,000-80,000 cells were seeded per well. Test compounds from this invention were added to the cells at different concentrations. Thapsigargin (TG) was added after 10 minutes and the cells were incubated for 4-8 h. The NFAT-Firefly luciferase and Tk-Renilla luciferase activity was measured using Dual-Glo reagent (Promega USA). The Renilla luciferase activity was used for protein normalization. Luminescence observed in cells treated with thapsigargin was considered 100% maximal signal and the reduced fluorescent signal observed in the presence of test compounds was expressed as percent inhibition of the maximal signal. The data was analyzed using 4-parametric sigmoidal dose response (variable slope) curve—fit.

In the above NFAT transcriptional activity assay, compounds of the present invention showed activity less than <1000 nM. Thus, compounds of the invention are shown to inhibit NFAT transcription activity.

Thus, the in vitro screening assays showed that the compounds of invention inhibit CRAC channel activity.

As mentioned hereinbefore, the CRAC channel is involved with numerous biological responses through various $Ca^{2+}$ signaling pathways. The compounds of the present invention are therefore useful for the treatment and/or prophylaxis of, although not limited to, inflammatory conditions, cancer, rheumatoid arthritis, allergic disorders, immune disorders, cardiovascular diseases, thrombocytopathies and all related conditions which can be benefitted by the CRAC channel modulatory properties of the compounds described herein.

The compounds of the present invention can be administered to a warm-blooded animal, including human being, for the treatment and/or prophylaxis of one or many diseases or disorders mentioned hereinabove which can be benefitted by the CRAC channel modulatory properties of the compounds described herein. The compounds may be formulated according to the methods known in the art as well as by new methods and may be administered to the body system via gastrointestinal tract as well as via other routes known to a person skilled in the art. Thus, administration of the compounds of the present invention via oral route, parenteral route, inhalation and /or topical applications are within the scope of this application. Any combination of a compound of the present invention with excipients and/or other therapeutic agents known in the art for the said conditions, diseases and/or disorders are also encompassed by the present invention.

All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

We claim:
1. A compound having the Formula (I):

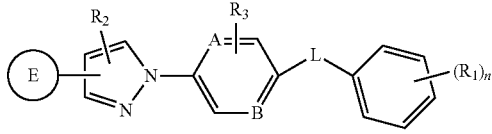

(I)

wherein,
one of A and B is N and the other is $CR_3$;
L is selected from —C(O)$NR_{11}$—, —$NR_{11}$C(O)—, —$CR_aR_bNR_{11}$— and —$NR_{11}CR_aR_b$—;
at each occurrence, $R_a$ and $R_b$ are independently hydrogen, substituted or unsubstituted alkyl or halogen;
ring E is 5 membered non aromatic heterocyclic ring of Formula (a)

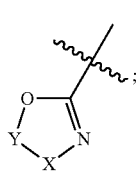

(a)

X is —NR—;
Y is —C(O)—;
R is selected from substituted or unsubstituted alkyl, haloalkyl, substituted or unsubstituted cycloalkyl, and —C(O)$R_8$;
$R_1$, which may be same or different at each occurrence, is independently selected from halogen, cyano, hydroxyl, substituted or unsubstituted alkyl, haloalkyl, substituted or unsubstituted alkoxy, haloalkoxy, substituted or unsubstituted cycloalkyl, substituted or unsubstituted cycloalkoxy, and —C(O)$OR_9$; or any two of adjacent $R_1$ groups together with the phenyl to which they are attached form substituted or unsubstituted naphthalene ring;
$R_2$ is selected from halogen, cyano, nitro, hydroxyl, substituted or unsubstituted alkyl, haloalkyl, substituted or unsubstituted alkoxy, haloalkoxy, substituted or unsubstituted cycloalkyl, substituted or unsubstituted cycloalkoxy, —$NR_6R_7$, —NHC(O)$R_8$, and —C(O)$OR_9$;
$R_3$ is selected from hydrogen, halogen, cyano, hydroxyl, substituted or unsubstituted alkyl, substituted or unsubstituted alkoxy, and substituted or unsubstituted cycloalkyl;
$R_6$ and $R_7$, which may be same or different at each occurrence, are independently selected from hydrogen, substituted or unsubstituted alkyl and substituted or unsubstituted cycloalkyl;
$R_8$ is substituted or unsubstituted alkyl;
$R_9$ is hydrogen or substituted or unsubstituted alkyl;
at each occurrence, $R_{11}$ is independently hydrogen or substituted or unsubstituted alkyl;
n is an integer ranging from 0 to 4, both inclusive; and
where the substituents on alkyl, cycloalkyl, alkoxy, cycloalkoxy, naphthalene ring are independently selected from hydroxy, halogen, carboxyl, cyano, nitro, alkyl, haloalkyl, aryl, cycloalkyl, —C(O)$OR^x$, —C(O)$NR^xR^y$, —$NR^xR^y$, —$NR^xC(O)R^y$, —S(O)$_2NR^xR^y$, —$OR^x$, —$SR^x$, and —S(O)$_2R^x$; wherein each occurrence of $R^x$, $R^y$ and $R^z$ are independently selected from hydrogen, halogen, alkyl, haloalkyl and cycloalkyl;
or a pharmaceutically acceptable salt thereof.

2. The compound of claim 1, having the Formula (II):

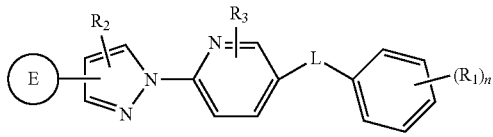

(II)

or a pharmaceutically acceptable salt thereof;
wherein ring E, $R_1$, $R_2$, $R_3$, L and 'n' are as defined in claim-1.

3. The compound of claim 1, having the Formula-(III):

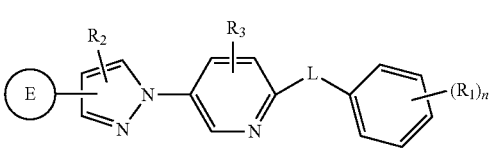

(III)

or a pharmaceutically acceptable salt thereof;
wherein ring E, $R_1$, $R_2$, $R_3$, L and 'n' are as defined in claim-1.

4. The compound of claim 1, wherein ring E is (a)

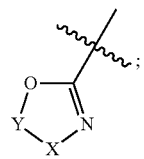

(a)

wherein X and y as defined in claim-1, and or a pharmaceutically acceptable salt thereof.

5. The compound of claim 1, wherein L is selected from —C(O)$NR_{11}$—, —$NR_{11}$C(O)— and —$NR_{11}CR_aR_b$— wherein $R_{11}$, $R_a$ and $R_b$ are independently a hydrogen or alkyl.

6. The compound of claim 1, wherein $R_1$ is same or different and are independently selected from halogen, cyano, hydroxyl, substituted or unsubstituted alkyl, haloalkyl, substituted or unsubstituted alkoxy, haloalkoxy and substituted or unsubstituted cycloalkyl; and 'n' is 0, 1, 2, or 3.

7. The compound of claim 1, wherein $R_2$ is selected from halogen, hydroxyl, cyano, nitro, substituted or unsubstituted alkyl, haloalkyl, substituted or unsubstituted alkoxy, haloalkoxy and substituted or unsubstituted cycloalkyl.

8. The compound of claim 1, wherein $R_3$ is selected from hydrogen, halogen, cyano, hydroxyl, substituted or unsubstituted alkyl, substituted or unsubstituted alkoxy and substituted or unsubstituted cycloalkyl.

9. The compound of claim 1, wherein one of A and B is N and the other is CH; L is —C(O)NH—, —NHC(O)— or $NHCH_2$—; $R_1$ is same or different and are independently selected from halogen, substituted or unsubstituted alkyl, haloalkyl and substituted or unsubstituted cycloalkyl; 'n' is 0, 1, 2, or 3; $R_2$ is halogen, substituted or unsubstituted alkyl, haloalkyl or substituted or unsubstituted cycloalkyl; $R_3$ is selected from hydrogen, halogen or substituted or unsubstituted alkyl; and ring E is

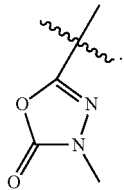

10. A compound which is selected from:
2,6-Difluoro-N-(6-(5-(4-methyl-5-oxo-4,5-dihydro-1,3,4-oxadiazol-2-yl)-3-(trifluoromethyl)-1H-pyrazol-1-yl)pyridin-3-yl)benzamide;
2-Fluoro-6-methyl-N-(6-(5-(4-methyl-5-oxo-4,5-dihydro-1,3,4-oxadiazol-2-yl)-3-(trifluoromethyl)-1H-pyrazol-1-yl)pyridin-3-yl)benzamide;
5-(3-Cyclopropyl-1-(5-((2,6-difluorobenzyl)amino)pyridin-2-yl)-1H-pyrazol-5-yl)-3-methyl-1,3,4-oxadiazol-2(3H)-one;
N-(6-(3-(Difluoromethyl)-5-(4-methyl-5-oxo-4,5-dihydro-1,3,4-oxadiazol-2-yl)-1H-pyrazol-1-yl)pyridin-3-yl)-2,6-difluorobenzamide;
5-(1-(5-((2,6-Difluorobenzyl)amino)pyridin-2-yl)-5-(fluoromethyl)-1H-pyrazol-3-yl)-3-methyl-1,3,4-oxadiazol-2(3H)-one;
2,6-Difluoro-N-(6-(3-(4-methyl-5-oxo-4,5-dihydro-1,3,4-oxadiazol-2-yl)-5-(trifluoromethyl)-1H-pyrazol-1-yl)pyridin-3-yl)benzamide;
2-Chloro-6-fluoro-N-(6-(3-(4-methyl-5-oxo-4,5-dihydro-1,3,4-oxadiazol-2-yl)-5-(trifluoromethyl)-1H-pyrazol-1-yl)pyridin-3-yl)benzamide;
2-Fluoro-6-methyl-N-(6-(3-(4-methyl-5-oxo-4,5-dihydro-1,3,4-oxadiazol-2-yl)-5-(trifluoromethyl)-1H-pyrazol-1-yl)pyridin-3-yl)benzamide;
N-(6-(5-(Difluoromethyl)-3-(4-methyl-5-oxo-4,5-dihydro-1,3,4-oxadiazol-2-yl)-1H-pyrazol-1-yl)pyridin-3-yl)-2,6-difluorobenzamide;
5-(1-(5-((2,6-Difluorobenzyl)amino)pyridin-2-yl)-5-(difluoromethyl)-1H-pyrazol-3-yl)-3-methyl-1,3,4-oxadiazol-2(3H)-one;
5-(1-(5-((2,6-Difluorobenzyl)amino)pyridin-2-yl)-3-(difluoromethyl)-1H-pyrazol-5-yl)-3-methyl-1,3,4-oxadiazol-2(3H)-one;
5-(1-(5-((2,6-Difluorobenzyl)amino)pyridin-2-yl)-5-(trifluoromethyl)-1H-pyrazol-3-yl)-3-methyl-1,3,4-oxadiazol-2(3H)-one;
5-(1-(5-((2-Chloro-6-fluorobenzyl)amino)pyridin-2-yl)-5-(trifluoromethyl)-1H-pyrazol-3-yl)-3-methyl- 1,3,4-oxadiazol-2(3H)-one;
N-(6-(5-Cyclopropyl-3-(4-methyl-5-oxo-4,5-dihydro-1,3,4-oxadiazol-2-yl)- 1H-pyrazol-1-yl)pyridin-3-yl)-2,6-difluorobenzamide;
N-(6-(3-Cyclopropyl-5-(4-methyl-5-oxo-4,5-dihydro-1,3,4-oxadiazol-2-yl)-1H-pyrazol-1-yl)pyridin-3-yl)-2,6-difluorobenzamide;
2,6-Difluoro-N-(6-(5-methyl-3-(4-methyl-5-oxo-4,5-dihydro-1,3,4-oxadiazol-2-yl)-1H-pyrazol-1-yl)pyridin-3-yl)benzamide;
5-(1-(5-((2,6-Difluorobenzyl)amino)pyridin-2-yl)-5-methyl-1H-pyrazol-3-yl)-3-methyl-1,3,4-oxadiazol-2(3H)-one;
2,6-Difluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
2-Chloro-6-fluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
2-Fluoro-6-methyl-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
2-Fluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
2,3-Difluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
2,4,5-Trifluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
2,3,4-Trifluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
2,4-Difluoro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
2,3-Dimethyl-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
2-Chloro-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
2-Methy-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
4-Ethyl-N-(5-(3-(4-methyl-5-oxo-4,5-dihydro-1,3,4-oxadiazol-2-yl)-5-(trifluoromethyl)-1H-pyrazol-1-yl)pyridin-2-yl)benzamide;
N-(5-(3-(4-Methyl-5-oxo-4,5-dihydro-1,3,4-oxadiazol-2-yl)-5-(trifluoromethyl)-1H-pyrazol-1-yl)pyridin-2-yl)-2-naphthamide;
5-(1-(6-((2,6-Difluorobenzyl)amino)pyridin-3-yl)-5-(trifluoromethyl)-1H-pyrazol-3-yl)-3-methyl-1,3,4-oxadiazol-2(3H)-one;
5-(1-(6-((2-Chloro-6-fluorobenzyl)amino)pyridin-3-yl)-5-(trifluoromethyl)-1H-pyrazol-3-yl)-3-methyl-1,3,4-oxadiazol-2(3H)-one;
5-(1-(6-((2-Fluoro-6-methylbenzyl)amino)pyridin-3-yl)-5-(trifluoromethyl)-1H-pyrazol-3-yl)-3-methyl-1,3,4-oxadiazol-2(3H)-one;
N-(2,6-Difluorophenyl)-6-(3-(4-methyl-5-oxo-4,5-dihydro-1,3,4-oxadiazol-2-yl)-5-(trifluoromethyl)-1H-pyrazol-1-yl)nicotinamide and
N-(2-Chloro-6-fluorophenyl)-6-(3-(4-methyl-5-oxo-4,5-dihydro-1,3,4-oxadiazol-2-yl)-5-(trifluoromethyl)-1H-pyrazol-1-yl)nicotinamide
or pharmaceutically acceptable salt thereof.

11. A pharmaceutical composition comprising one or more compounds of Formula (I) according to claim 1 and one or more pharmaceutically acceptable excipients.

* * * * *